(12) United States Patent
Amadio et al.

(10) Patent No.: US 10,098,894 B2
(45) Date of Patent: Oct. 16, 2018

(54) TRANSDERMAL CREAM

(71) Applicant: TherapeuticsMD, Inc., Boca Raton, FL (US)

(72) Inventors: Julia Amadio, Boca Raton, FL (US); Annette Shadiack, Somerset, NJ (US); Peter H. R. Persicaner, Boca Raton, FL (US); Richard Winneker, Penllyn, PA (US); Jason Legassie, Stuart, FL (US); Thorsteinn Thorsteinsson, Boynton Beach, FL (US); Ajay Ghanta, North Palm Beach, FL (US)

(73) Assignee: TherapeuticsMD, Inc., Boca Raton, FL (US)

( * ) Notice: Subject to any disclaimer, the term of this patent is extended or adjusted under 35 U.S.C. 154(b) by 46 days.

(21) Appl. No.: 14/812,179

(22) Filed: Jul. 29, 2015

(65) Prior Publication Data
US 2016/0030449 A1    Feb. 4, 2016

Related U.S. Application Data

(60) Provisional application No. 62/030,540, filed on Jul. 29, 2014, provisional application No. 62/152,674, filed on Apr. 24, 2015.

(51) Int. Cl.
| | |
|---|---|
| *A01N 45/00* | (2006.01) |
| *A61K 31/56* | (2006.01) |
| *A61K 31/57* | (2006.01) |
| *A61K 31/565* | (2006.01) |
| *A61K 9/00* | (2006.01) |
| *A61K 9/06* | (2006.01) |
| *A61K 47/14* | (2017.01) |
| *A61K 47/06* | (2006.01) |

(52) U.S. Cl.
CPC ............ *A61K 31/57* (2013.01); *A61K 9/0014* (2013.01); *A61K 9/06* (2013.01); *A61K 31/565* (2013.01); *A61K 47/06* (2013.01); *A61K 47/14* (2013.01)

(58) Field of Classification Search
CPC ........ A61K 31/27; A61K 31/57; A61K 47/44; A61K 51/082; A61K 9/0014; A61K 9/0048; A61K 9/10; A61K 9/19
USPC ........................................................ 514/171
See application file for complete search history.

(56) References Cited

U.S. PATENT DOCUMENTS

| | | | |
|---|---|---|---|
| 3,921,636 A | 11/1975 | Zaffaroni |
| 3,948,254 A | 4/1976 | Zaffaroni |
| 3,971,367 A | 7/1976 | Zaffaroni |
| 4,196,188 A | 4/1980 | Besins |
| 4,310,510 A | 1/1982 | Sherman |
| 4,372,951 A | 2/1983 | Voiys |
| 4,865,848 A | 9/1989 | Cheng |
| 4,900,734 A | 2/1990 | Maxson |
| 5,064,654 A | 11/1991 | Berner |
| 5,140,021 A | 8/1992 | Maxson |
| 5,164,416 A | 11/1992 | Nagai |
| 5,474,783 A | 12/1995 | Miranda |
| 5,514,673 A | 5/1996 | Heckenmuller |
| 5,543,150 A | 8/1996 | Bologna |
| 5,565,199 A | 10/1996 | Page |
| 5,582,592 A | 12/1996 | Kendrick |
| 5,595,970 A | 1/1997 | Garfield |
| 5,609,617 A | 3/1997 | Shealy |
| 5,620,705 A | 4/1997 | Dong |
| 5,660,839 A | 8/1997 | Allec |
| 5,686,097 A | 11/1997 | Taskovich |
| 5,744,463 A | 4/1998 | Bair |
| 5,747,058 A | 5/1998 | Tipton |
| 5,780,050 A | 7/1998 | Jain |
| 5,811,416 A | 9/1998 | Chwalisz |
| 5,814,329 A | 9/1998 | Shah |
| 5,840,327 A | 11/1998 | Gale |
| 5,843,979 A | 12/1998 | Wille |
| 5,882,676 A | 3/1999 | Lee |
| 5,898,038 A | 4/1999 | Yallampalli |

(Continued)

FOREIGN PATENT DOCUMENTS

| | | |
|---|---|---|
| EP | 279977 A2 | 8/1988 |
| EP | 811381 A1 | 12/1997 |

(Continued)

OTHER PUBLICATIONS

Lopes et al, Pharmaceutical Development and Technology, 2009; 14(5): 524-529.*
Monti et al, International Journal of Pharmaceutics 237 (2002) 209-214.*
Karande et al, Biochimica et Biophysica Acta 1788 (2009) 2362-2373.*
Ah et al, Drug Development and Industrial Pharmacy, vol. 30, No. 6, pp. 557-564, 2004.*

(Continued)

*Primary Examiner* — Jean P Cornet
(74) *Attorney, Agent, or Firm* — Kilpatrick Townsend & Stockton LLP

(57) ABSTRACT

This disclosure relates to transdermal pharmaceutical compositions containing progesterone in combination with one or more solubilizing agents and penetration enhancers, wherein the pharmaceutical compositions are formulated as creams for topical administration. In some embodiments, the transdermal pharmaceutical compositions contain progesterone, a medium-chain oil, and d-limonene. In some embodiments, the transdermal pharmaceutical compositions contain progesterone, a medium-chain oil, a penetration enhancer (e.g., propylene glycol, a fatty acid ester of propylene glycol, a glycol ether), and optionally d-limonene. In certain embodiments, the pharmaceutical compositions further include estradiol. Methods for treating conditions associated with hormone deficiency in a subject are also described.

10 Claims, 10 Drawing Sheets

(56) References Cited

U.S. PATENT DOCUMENTS

| | | |
|---|---|---|
| 5,942,531 A | 8/1999 | Diaz |
| 5,968,919 A | 10/1999 | Samour |
| 5,985,311 A | 11/1999 | Cordes |
| 5,985,861 A | 11/1999 | Levine |
| 6,030,948 A | 2/2000 | Mann |
| 6,056,972 A | 5/2000 | Hermsmeyer |
| 6,077,531 A | 6/2000 | Satin Drouin |
| 6,086,916 A | 7/2000 | Agnus |
| 6,096,338 A | 8/2000 | Lacy |
| 6,124,362 A | 9/2000 | Bradbury |
| 6,139,868 A | 10/2000 | Hoffmann |
| 6,139,873 A | 10/2000 | Hughes |
| 6,165,491 A | 12/2000 | Grasset |
| 6,187,323 B1 | 2/2001 | Aiache |
| 6,225,297 B1 | 5/2001 | Stockemann |
| 6,228,852 B1 | 5/2001 | Shaak |
| 6,242,509 B1 | 6/2001 | Berger |
| 6,267,984 B1 | 7/2001 | Beste |
| 6,277,418 B1 | 8/2001 | Markaverich |
| 6,294,192 B1 | 9/2001 | Patel |
| 6,303,132 B1 | 10/2001 | Nelson |
| 6,420,352 B1 | 7/2002 | Knowles |
| 6,432,438 B1 | 8/2002 | Shukla |
| 6,440,454 B1 | 8/2002 | Santoro |
| 6,444,234 B1 | 9/2002 | Kirby |
| 6,451,339 B2 | 9/2002 | Patel |
| 6,544,553 B1 | 4/2003 | Hsia |
| 6,562,370 B2 | 5/2003 | Luo |
| 6,562,790 B2 | 5/2003 | Chein |
| 6,569,463 B2 | 5/2003 | Patel |
| 6,610,674 B1 | 8/2003 | Schreiber |
| 6,635,274 B1 | 10/2003 | Masiz |
| 6,656,929 B1 | 12/2003 | Agnus |
| 6,682,757 B1 | 1/2004 | Wright |
| 6,708,822 B1 | 3/2004 | Muni |
| 6,720,001 B2 | 4/2004 | Chen |
| 6,743,448 B2 | 6/2004 | Kryger |
| 6,787,152 B2 | 9/2004 | Kirby |
| 6,923,988 B2 | 8/2005 | Patel |
| 6,967,194 B1 | 11/2005 | Matsuo |
| 7,011,846 B2 | 3/2006 | Shojaei |
| 7,030,104 B2 | 4/2006 | Gray |
| 7,094,228 B2 | 8/2006 | Zhang |
| 7,105,573 B2 | 9/2006 | Krajcik |
| 7,163,699 B2 | 1/2007 | Besse |
| 7,267,829 B2 | 9/2007 | Kirby |
| 7,374,779 B2 | 5/2008 | Chen |
| 7,381,427 B2 | 6/2008 | Ancira |
| 7,429,576 B2 | 9/2008 | Labrie |
| 7,572,780 B2 | 8/2009 | Hermsmeyer |
| 7,589,082 B2 | 9/2009 | Savoir |
| 7,799,769 B2 | 9/2010 | White |
| 7,858,607 B2 | 12/2010 | Mamchur |
| 7,879,830 B2 | 2/2011 | Wiley |
| 8,075,917 B2 | 12/2011 | Chung |
| 8,080,553 B2 | 12/2011 | Keith |
| 8,158,613 B2 | 4/2012 | Staniforth |
| 8,163,722 B2 | 4/2012 | Savoir |
| 8,187,615 B2 | 5/2012 | Friedman |
| 8,221,785 B2 | 7/2012 | Chien |
| 8,241,664 B2 | 8/2012 | Dudley |
| 8,268,806 B2 | 9/2012 | Labrie |
| 8,318,898 B2 | 11/2012 | Fasel |
| 8,329,680 B2 | 12/2012 | Evans |
| 8,362,091 B2 | 1/2013 | Tamarkin |
| 8,372,806 B2 | 2/2013 | Böhler |
| 8,449,879 B2 | 5/2013 | Laurent-Applegate |
| 8,454,945 B2 | 6/2013 | Mccook |
| 8,455,468 B2 | 6/2013 | Hoffman |
| 8,476,252 B2 | 7/2013 | Achleitner |
| 8,512,754 B2 | 8/2013 | Needham |
| 8,518,376 B2 | 8/2013 | Tamarkin |
| 8,536,159 B2 | 9/2013 | Li |
| 8,551,508 B2 | 10/2013 | Lee |
| 8,633,178 B2 | 1/2014 | Bernick |
| 8,633,180 B2 | 1/2014 | Li |
| 8,636,982 B2 | 1/2014 | Tamarkin |
| 8,658,628 B2 | 2/2014 | Baucom |
| 8,664,207 B2 | 3/2014 | Li |
| 8,679,552 B2 | 3/2014 | Guthery |
| 8,697,710 B2 | 4/2014 | Li |
| 8,703,105 B2 | 4/2014 | Tamarkin |
| 8,709,385 B2 | 4/2014 | Tamarkin |
| 8,715,735 B2 | 5/2014 | Funke |
| 8,735,381 B2 | 5/2014 | Podolski |
| 8,741,336 B2 | 6/2014 | Dipierro |
| 8,741,373 B2 | 6/2014 | Bromley |
| 8,784,882 B2 | 7/2014 | Mattern |
| 8,846,648 B2 | 9/2014 | Bernick |
| 8,846,649 B2 | 9/2014 | Bernick |
| 8,933,059 B2 | 1/2015 | Bernick |
| 8,987,237 B2 | 3/2015 | Bernick |
| 8,987,238 B2 | 3/2015 | Bernick |
| 8,993,548 B2 | 3/2015 | Bernick |
| 8,993,549 B2 | 3/2015 | Bernick |
| 9,006,222 B2 | 4/2015 | Bernick |
| 9,012,434 B2 | 4/2015 | Bernick |
| 2001/0031747 A1 | 10/2001 | Deziegler |
| 2002/0035070 A1 | 3/2002 | Gardlik |
| 2002/0119174 A1 | 8/2002 | Gardlik |
| 2002/0119198 A1 | 8/2002 | Gao |
| 2002/0173510 A1 | 11/2002 | Levinson |
| 2003/0064097 A1 | 4/2003 | Patel |
| 2003/0077297 A1 | 4/2003 | Chen |
| 2003/0091620 A1 | 5/2003 | Fikstad |
| 2003/0092691 A1 | 5/2003 | Besse |
| 2003/0104048 A1 | 6/2003 | Patel |
| 2003/0124182 A1 | 7/2003 | Shojaei |
| 2003/0175329 A1 | 9/2003 | Azarnoff |
| 2003/0180352 A1 | 9/2003 | Patel |
| 2003/0215496 A1 | 11/2003 | Patel |
| 2003/0235596 A1 | 12/2003 | Gao |
| 2003/0236236 A1 | 12/2003 | Chen |
| 2004/0043043 A1 | 3/2004 | Schlyter |
| 2004/0052824 A1 | 3/2004 | Abou Chacra Vernet |
| 2004/0101557 A1 | 5/2004 | Gibson |
| 2004/0131670 A1 | 7/2004 | Gao |
| 2004/0138103 A1 | 7/2004 | Patt |
| 2004/0147578 A1 | 7/2004 | Calvet |
| 2004/0191207 A1 | 9/2004 | Lipari |
| 2004/0210280 A1 | 10/2004 | Liedtke |
| 2004/0225140 A1 | 11/2004 | Fernandez |
| 2004/0234606 A1 | 11/2004 | Levine |
| 2004/0253319 A1 | 12/2004 | Netke |
| 2005/0020552 A1 | 1/2005 | Aschkenasy |
| 2005/0031651 A1 | 2/2005 | Gervais |
| 2005/0054991 A1 | 3/2005 | Tobyn |
| 2005/0085453 A1 | 4/2005 | Govindarajan |
| 2005/0101579 A1 | 5/2005 | Shippen |
| 2005/0118244 A1 | 6/2005 | Theobald |
| 2005/0182105 A1 | 8/2005 | Nirschl |
| 2005/0187267 A1 | 8/2005 | Hamann |
| 2005/0207990 A1 | 9/2005 | Funke |
| 2005/0214384 A1 | 9/2005 | Juturu |
| 2005/0220825 A1 | 10/2005 | Funke |
| 2005/0239747 A1 | 10/2005 | Yang |
| 2005/0239758 A1 | 10/2005 | Roby |
| 2005/0244522 A1 | 11/2005 | Carrara |
| 2005/0250746 A1 | 11/2005 | Iammatteo |
| 2006/0052341 A1 | 3/2006 | Cornish |
| 2006/0069031 A1 | 3/2006 | Loumaye |
| 2006/0078618 A1 | 4/2006 | Constantinides |
| 2006/0110415 A1 | 5/2006 | Gupta |
| 2006/0134188 A1 | 6/2006 | Podhaisky |
| 2006/0204557 A1 | 9/2006 | Gupta |
| 2006/0240111 A1 | 10/2006 | Fernandez |
| 2006/0247216 A1 | 11/2006 | Haj Yehia |
| 2006/0252049 A1 | 11/2006 | Shuler |
| 2006/0275218 A1 | 12/2006 | Tamarkin |
| 2006/0275360 A1 | 12/2006 | Ahmed |
| 2007/0021360 A1 | 1/2007 | Nyce |
| 2007/0037780 A1 | 2/2007 | Ebert |
| 2007/0167418 A1 | 7/2007 | Ferguson |
| 2007/0196433 A1 | 8/2007 | Ron |

(56) References Cited

U.S. PATENT DOCUMENTS

| | | |
|---|---|---|
| 2007/0264309 A1 | 11/2007 | Chollet |
| 2007/0264345 A1 | 11/2007 | Eros |
| 2007/0264349 A1 | 11/2007 | Lee |
| 2007/0292359 A1 | 12/2007 | Friedman |
| 2007/0292461 A1 | 12/2007 | Tamarkin |
| 2008/0026035 A1 | 1/2008 | Chollet |
| 2008/0039405 A1 | 2/2008 | Langley |
| 2008/0050317 A1 | 2/2008 | Tamarkin |
| 2008/0063607 A1 | 3/2008 | Tamarkin |
| 2008/0069779 A1 | 3/2008 | Tamarkin |
| 2008/0095831 A1 | 4/2008 | Mc Graw |
| 2008/0139392 A1 | 6/2008 | Acosta-Zara |
| 2008/0175905 A1 | 7/2008 | Liu |
| 2008/0175908 A1 | 7/2008 | Liu |
| 2008/0206159 A1 | 8/2008 | Tamarkin |
| 2008/0206161 A1 | 8/2008 | Tamarkin |
| 2008/0227763 A1 | 9/2008 | Lanquetin |
| 2008/0312197 A1 | 12/2008 | Rodriguez |
| 2009/0010968 A1 | 1/2009 | Allart |
| 2009/0017120 A1 | 1/2009 | Trimble |
| 2009/0053294 A1 | 2/2009 | Prendergast |
| 2009/0074859 A1 | 3/2009 | Patel |
| 2009/0081303 A1 | 3/2009 | Savoir |
| 2009/0098069 A1 | 4/2009 | Vacca |
| 2009/0130029 A1 | 5/2009 | Tamarkin |
| 2009/0131385 A1 | 5/2009 | Voskuhl |
| 2009/0137478 A1 | 5/2009 | Bernstein |
| 2009/0175799 A1 | 7/2009 | Tamarkin |
| 2009/0186081 A1 | 7/2009 | Holm |
| 2009/0227550 A1 | 9/2009 | Mattern |
| 2009/0264395 A1 | 10/2009 | Creasy |
| 2009/0285869 A1 | 11/2009 | Trimble |
| 2010/0028360 A1 | 2/2010 | Atwood |
| 2010/0034838 A1 | 2/2010 | Staniforth |
| 2010/0034880 A1 | 2/2010 | Sintov |
| 2010/0055138 A1 | 3/2010 | Margulies |
| 2010/0086501 A1 | 4/2010 | Chang |
| 2010/0136105 A1 | 6/2010 | Chen |
| 2010/0137271 A1 | 6/2010 | Chen |
| 2010/0143420 A1 | 6/2010 | Shenoy |
| 2010/0143481 A1 | 6/2010 | Shenoy |
| 2010/0183723 A1 | 7/2010 | Laurent-Applegate |
| 2010/0184736 A1 | 7/2010 | Coelingh Bennink |
| 2010/0190758 A1 | 7/2010 | Fauser |
| 2010/0204326 A1 | 8/2010 | D'Souza |
| 2010/0221195 A1 | 9/2010 | Tamarkin |
| 2010/0247632 A1 | 9/2010 | Dong |
| 2010/0255085 A1 | 10/2010 | Liu |
| 2010/0273730 A1 | 10/2010 | Hsu |
| 2010/0316724 A1 | 12/2010 | Whitfield |
| 2010/0322884 A1 | 12/2010 | Dipietro |
| 2010/0330168 A1 | 12/2010 | Gicquel |
| 2011/0028439 A1 | 2/2011 | Witt-Enderby |
| 2011/0039814 A1 | 2/2011 | Huatan |
| 2011/0086825 A1 | 4/2011 | Chatroux |
| 2011/0098258 A1 | 4/2011 | Masini-Eteve |
| 2011/0104289 A1 | 5/2011 | Savoir Vilboeuf |
| 2011/0142945 A1 | 6/2011 | Chen |
| 2011/0158920 A1 | 6/2011 | Morley |
| 2011/0217341 A1 | 9/2011 | Sah |
| 2011/0244043 A1 | 10/2011 | Xu |
| 2011/0262373 A1 | 10/2011 | Umbert Millet |
| 2011/0262494 A1 | 10/2011 | Achleitner |
| 2011/0268665 A1 | 11/2011 | Tamarkin |
| 2011/0281832 A1 | 11/2011 | Li |
| 2011/0287094 A1 | 11/2011 | Penhasi |
| 2011/0293720 A1 | 12/2011 | General |
| 2011/0306579 A1 | 12/2011 | Stein |
| 2011/0312927 A1 | 12/2011 | Nachaegari |
| 2011/0312928 A1 | 12/2011 | Nachaegari |
| 2011/0318405 A1 | 12/2011 | Erwin |
| 2012/0021041 A1 | 1/2012 | Rossi |
| 2012/0028910 A1 | 2/2012 | Combal |
| 2012/0046264 A1 | 2/2012 | Simes |
| 2012/0052077 A1 | 3/2012 | Truitt |
| 2012/0058979 A1 | 3/2012 | Keith |
| 2012/0101073 A1 | 4/2012 | Mannion |
| 2012/0128777 A1 | 5/2012 | Keck |
| 2012/0129819 A1 | 5/2012 | Vancaillie |
| 2012/0136013 A1 | 5/2012 | Li |
| 2012/0295911 A1 | 11/2012 | Mannion |
| 2012/0301517 A1 | 11/2012 | Zhang |
| 2012/0302535 A1 | 11/2012 | Caufriez |
| 2012/0322779 A9 | 12/2012 | Voskuhl |
| 2012/0328549 A1 | 12/2012 | Edelson |
| 2013/0011342 A1 | 1/2013 | Tamarkin |
| 2013/0022674 A1 | 1/2013 | Dudley |
| 2013/0023505 A1 | 1/2013 | Garfield |
| 2013/0028850 A1 | 1/2013 | Tamarkin |
| 2013/0029957 A1 | 1/2013 | Giliyar |
| 2013/0045953 A1 | 2/2013 | Sitruk-Ware |
| 2013/0084257 A1 | 4/2013 | Ishida |
| 2013/0085123 A1 | 4/2013 | Li |
| 2013/0116222 A1 | 5/2013 | Arnold |
| 2013/0122051 A1 | 5/2013 | Abidi |
| 2013/0123220 A1 | 5/2013 | Queiroz |
| 2013/0129818 A1* | 5/2013 | Bernick ............. A61K 9/16 424/451 |
| 2013/0164225 A1 | 6/2013 | Tamarkin |
| 2013/0165744 A1 | 6/2013 | Carson |
| 2013/0183254 A1 | 7/2013 | Zhou |
| 2013/0183325 A1 | 7/2013 | Bottoni |
| 2013/0189193 A1 | 7/2013 | Tamarkin |
| 2013/0189368 A1 | 7/2013 | Mosqueira |
| 2013/0224268 A1 | 8/2013 | Alam |
| 2013/0225412 A1 | 8/2013 | Sardari Lodriche |
| 2013/0245570 A1 | 9/2013 | Jackson |
| 2013/0324565 A1 | 12/2013 | Li |
| 2013/0331363 A1 | 12/2013 | Li |
| 2013/0338122 A1 | 12/2013 | Bernick |
| 2013/0338123 A1 | 12/2013 | Bernick |
| 2013/0338124 A1 | 12/2013 | Li |
| 2013/0345187 A1 | 12/2013 | Rodriguez Oquendo |
| 2014/0031323 A1 | 1/2014 | Perez |
| 2014/0079686 A1 | 3/2014 | Barman |
| 2014/0088051 A1 | 3/2014 | Bernick |
| 2014/0088059 A1 | 3/2014 | Perumal |
| 2014/0094440 A1 | 4/2014 | Bernick |
| 2014/0094441 A1 | 4/2014 | Bernick |
| 2014/0099362 A1 | 4/2014 | Bernick |
| 2014/0100204 A1 | 4/2014 | Bernick |
| 2014/0100205 A1 | 4/2014 | Bernick |
| 2014/0100206 A1 | 4/2014 | Bernick |
| 2014/0113889 A1 | 4/2014 | Connor |
| 2014/0194396 A1 | 7/2014 | Li |
| 2014/0206616 A1 | 7/2014 | Ko |
| 2014/0213565 A1 | 7/2014 | Bernick |
| 2014/0329783 A1 | 11/2014 | Bernick |
| 2014/0371182 A1 | 12/2014 | Bernick |
| 2014/0371183 A1 | 12/2014 | Bernick |
| 2014/0371184 A1 | 12/2014 | Bernick |
| 2014/0371185 A1 | 12/2014 | Bernick |
| 2015/0031654 A1 | 1/2015 | Amadio |
| 2015/0045335 A1 | 2/2015 | Bernick |
| 2015/0133421 A1 | 5/2015 | Bernick |

FOREIGN PATENT DOCUMENTS

| | | |
|---|---|---|
| EP | 1094781 B1 | 7/2008 |
| EP | 2191833 A1 | 6/2010 |
| GB | 848881 A | 9/1960 |
| GB | 589946 A | 5/1981 |
| IN | 216026 B | 3/2008 |
| IN | 244217 B | 11/2010 |
| WO | 1990011064 A1 | 10/1990 |
| WO | 1993017686 A1 | 9/1993 |
| WO | 1994022426 A1 | 10/1994 |
| WO | 1996009826 A2 | 4/1996 |
| WO | 1996030000 A1 | 10/1996 |
| WO | 1997043989 A1 | 11/1997 |
| WO | 1998010293 A1 | 3/1998 |
| WO | 1998051280 A1 | 11/1998 |
| WO | 1999022680 A1 | 5/1999 |
| WO | 1999032072 A1 | 7/1999 |

(56) References Cited

FOREIGN PATENT DOCUMENTS

| | | |
|---|---|---|
| WO | 1999039700 A1 | 8/1999 |
| WO | 1999048477 A1 | 9/1999 |
| WO | 99/62497 A1 | 12/1999 |
| WO | 1999063974 A2 | 12/1999 |
| WO | 2000001351 A1 | 1/2000 |
| WO | 2000050007 A1 | 8/2000 |
| WO | 2001037808 A1 | 5/2001 |
| WO | 2001054699 A1 | 8/2001 |
| WO | 2002007700 A2 | 1/2002 |
| WO | 2002011768 A1 | 2/2002 |
| WO | 2002022132 A2 | 3/2002 |
| WO | 2002040008 A2 | 5/2002 |
| WO | 2002041878 A2 | 5/2002 |
| WO | 2002053131 A1 | 7/2002 |
| WO | 2003028667 A2 | 4/2003 |
| WO | 2003068186 A1 | 8/2003 |
| WO | 2003077923 A1 | 9/2003 |
| WO | 2003092588 A2 | 11/2003 |
| WO | 2004014432 A1 | 2/2004 |
| WO | 2004052336 A2 | 6/2004 |
| WO | 2005087194 A1 | 9/2005 |
| WO | 2005087199 A2 | 9/2005 |
| WO | 2005115335 A1 | 12/2005 |
| WO | 2006036899 A2 | 4/2006 |
| WO | 2006053172 A2 | 5/2006 |
| WO | 2006113505 A2 | 10/2006 |
| WO | 2007103294 A2 | 9/2007 |
| WO | 2007120868 A2 | 10/2007 |
| WO | 2007123790 A1 | 11/2007 |
| WO | 2008152444 A2 | 12/2008 |
| WO | 2009002542 A1 | 12/2008 |
| WO | 2009036311 A1 | 3/2009 |
| WO | 2009040818 A1 | 4/2009 |
| WO | 2009098072 A2 | 8/2009 |
| WO | 2009133352 A2 | 11/2009 |
| WO | 2011000210 A1 | 1/2011 |
| WO | 2011073995 A2 | 6/2011 |
| WO | 2011120084 A1 | 10/2011 |
| WO | 2012118563 A2 | 9/2012 |
| WO | 2012127501 A2 | 9/2012 |
| WO | 2012156822 A1 | 11/2012 |
| WO | 2012166909 A1 | 12/2012 |
| WO | 2013011501 A1 | 1/2013 |
| WO | 2013112947 A1 | 8/2013 |
| WO | 2013124415 A1 | 8/2013 |
| WO | 2013127727 A1 | 9/2013 |
| WO | 2013127728 A1 | 9/2013 |
| WO | 2013149258 A2 | 10/2013 |
| WO | 2013158454 A2 | 10/2013 |
| WO | 2013170052 A1 | 11/2013 |
| WO | 2013192248 A1 | 12/2013 |
| WO | 2013192249 A1 | 12/2013 |
| WO | 2013192250 A1 | 12/2013 |
| WO | 2013192251 A1 | 12/2013 |
| WO | 2014009434 A1 | 1/2014 |
| WO | 2014018856 A1 | 1/2014 |
| WO | 2014018932 A2 | 1/2014 |
| WO | 2014052792 A1 | 4/2014 |
| WO | 2014076569 A2 | 5/2014 |
| WO | 2014104784 A1 | 7/2014 |

OTHER PUBLICATIONS

Search Report, International Search Report for PCT/US15/042621, dated Oct. 29, 2015.
Abitec, CapmulMCM, EP, Technical Data Sheet, version 10, 2014, Columbus, OH.
Abitec, CapmulMCM, NF, Technical Data Sheet, version 6, 2014, Columbus, OH.
Abitec, CapmulMCM, Saftey Data Sheet, 2011, Janesville, WI.
Abitec, CapmulMCM, Technical Data Sheet, version 17, 2014, Columbus, OH.
Abitec, CapmulPG8, CAS No. 31565-12-5, version 11, 2006, Columbus, OH.
Acarturk, Fusun, Mucoadhesive Vaginal Drug Delivery System, Recent Patents on Drug Delivery & Formulation, 2009, vol. 3, pp. 193-195.
Araya-Sibija, Andrea M.A., Morphology Study of Progesterone Polymorphs Prepared by Polymer-Induced Heteronucleation (PIHn), Scanning vol. 35 pp. 213-21, 2013, Wiley Period., Inc.
Azeem, Adnan et al., Microemulsions as a Surrogate Carrier for Dermal Drug Delivery, Drug Development and Industrial Pharmacy, May 2000, vol. 35, No. 5, pp. 525-547 (abstract only). http://informahealthcare.com/doi/abs/10.1080/03639040802448646.
Azure Pharma, Inc., ELESTRIN™—Estradiol Gel, Drug Info, http://dailymed.nlm.nih.gov/dailymed/archives/fdaDrugInfo.cfm?archiveid=11885, 26 pages, Aug. 2009.
Bartosova, Transdermal Drug Delivery In Vitro Using Diffusion Cells, Current Medicinal Chemistry, 2012, 19, 4671-4677, Bentham Science Publishers.
BioMed Central, Solubility of Progesterone in Organic Solvents, Online PDF, http://www.biomedcentral.com/content/supplementary/1475-2859-11-106-S2.pdf
Blake et al., Single and multidose pharmacokinetic study of a vaginal micronized progesterone insert (Endometrin) compared with vaginal gel in healthy reproductiveaged female subjects, Fertility and Sterility# vol. 94, No. 4, Sep. 2010, Elsevier.
Burry, Kenneth A, Percutaneous absorption of progesterone in postmenopausal women treated with transdermal estrogen, Am J Obstet Gynecol, vol. 180(6) part 1, pp. 1504-1511, 1999.
Chun et al., Transdermal Delivery of Estradiol and Norethrindrone Acetate: Effect of Vehicles . . . , J. Kor. Pharm. Sci., vol. 35, No. 3, pp. 173-177 (2005).
Cicinelli et al., Direct Transport of Progesterone From Vagina to Uterus, Obstetrics & Gynecology, vol. 95, No. 3, March 2000, pp. 403-406.
Cooper, A, et al., Systemic absorption of progesterone from Progest cream in postmenopausal women, The Lancet, vol. 351, pp. 1255-1256, Research Letters, Apr. 25, 1998.
Drakulic, Branko J, Role of complexes formation between drugs and penetration enhancers in transdermal . . . , Inter. Journal of Pharmaceutics, Elsevier, vol. 363, pp. 40-49, 2009.
Du et al., Percutaneous progesterone delivery via cream or gel application in postmenopausal women: a randomized cross-over study of progesterone levels in serum, whole blood, saliva, and capillary blood, Menopause: The Journal of the North American Menopause Society, 2013, vol. 20, No. 11, pp. 1-7.
Excipients for Pharmaceuticals, Sasol Olefins & Surfactants GMBH, 2010, 28 pages.
FDA, Draft Guidance on Progesterone, Recommended Apr. 2010, Revised Feb. 2011 http://www.fda.gov/downloads/Drugs/GuidanceComplianceRegulatoryInformation/Guidances/UCM209294.pdf.
Gattefosse SAS, Material Safety Data Sheet, Gelot 64, 2012, 8 pages.
GattefosséSAS, Regulatory Data Sheet, Gelot 64, 2012, 6 pages.
GattefosséSAS, Regulatory Data Sheet, Lauroglycol 90, 2012, 5 pages.
Gattefossé, "Excipients for Safe and Effective Topical Delivery, Drug Development and Delivery" Jul./Aug. 2012, http://drug-dev.com/Main/B1ck-Issues/Transdermal-Topical-Subcutaneous-NonInvasive-Deliv-5.aspx#.
Glaser et al, Pilot Study: Absorption and Efficacy of Multiple Hormones Delivered in a Single Cream Applied to the Mucous Membranes of the Labia and Vagina, Gynecol Obstet Invest 2008;66: 111-118.
Herman, Anna et al., "Essential oils and their constituents as skin penetration enhancer for transdermal drug delivery: a review," 2014 Royal Pharmaceutical Society, Journal of Pharmacy and Pharmacology, pp. 1-13.
Idder, Salima, et al., Physicochemical properties of Progesterone, SciFinder, pp. 1-26, Feb. 24, 2014, American Chem. Society & US Natl. Lib. of Med.
Land, Laura M, The influence of water content of triglyceride oils on the solubility of steriods, Pharmaceutical Research, vol. 22(5) May 2005, Springer Science+Business Media.

(56) References Cited

OTHER PUBLICATIONS

Lane, M.E., Skin penetration enhancers, International Journal of Pharmaceutics, 2013, vol. 447, No. 1, pp. 12-21.

Leonetti et al., Transdermal progesterone cream as an alternative progestin in hormone therapy, Alternative Therapies, Nov./Dec. 2005, vol. 11, No. 6, pp. 36-38.

Leonetti, Helene B, et al., Topical progesterone cream has an antiproliferative effect on estrogen-stimulated endometrium, Fertility and Sterility, vol. 79(1), Jan. 2003.

Lewis, John G. et al., Caution on the use of saliva measurements to monitor absorption of progesterone from transdermal creams in postmenopausal women, Maturitas, The European Menopause Journal, vol. 41, pp. 1-6, 2002.

Miao, Wenbin, et al., Chemical Properties of Progesterone, SciFinder, 2014, American Chemical Society & US Natl. Lib. of Med.

Miles et al., Pharmacokinetics and endometrial tissue levels of progesterone after administration bv'Intramuscular and vaginal routes: a comparative study, Fertility and Sterility, vol. 62, No. 3, Sep. 1994, pp. 485-490.

O'Leary, Peter, Salivary, but not serum or urinary levels of progesterone are elevated after topical application of progersterone cream to pre-and post-menopausal women, Clinical Endocrinology, vol. 53 pp. 615-620, Blackwell Science 2000.

Patel et al., Transdermal Drug Delivery System: A Review, www.thepharmajournal.com, vol. 1, No. 4, 2012, pp. 78-87.

Persson, Linda C, et al., Physicochemical Properties of Progesterone Selecte, SciFinder, pp. 1-5, Feb. 24, 2014, American Chem. Society & US Natl. Lib. of Med.

Product Information Sheet, Body Balance Cream, Tahitian Noni International, 2013, 1 page.

Ross et al., Randomized, double-blind, dose-ranging study of the endometrial effects of a vaginal progesterone gel in estrogen-treated postmenopausal women, AnnJ Obstet Gynecol, Oct. 1997, vol. 177, No. 4, pp. 937-941.

Ruan et al., Systemic progesterone therapy—Oral, vaginal, injections and even transdermal? Maturitas 79 (2014) 248-255, Elsevier.

Salole, Eugene G., The physicochemical properties of oestradiol, Journal of Pharmaceutical & Biomedical Analysis, vol. 5, No. 7, pp. 635-648, 1987.

Santen, RJ, Vaginal administration of estradiol: effects of dose, preparation and timing on plasma estradiol levels, Climacteric 2014;17:1-14.

Sarkar, Bisu, et al., Chemical Stability of Progesterone in Compounded Topical Preparations using PLO Transdermal Cream™ and HRT Cream™ B1se . . . , J Steroids Horm Sci, 4:2, 2013.

SciFinder Scholar Progesterone Experimental Properties, SciFinder, pp. 1-9, Feb. 24, 2014, American Chem. Society.

Sharma, H.C., et al., Physical Properties of Progesterone Selected Refer, SciFinder, pp. 1-5, Feb. 24, 2014, American Chem. Society & US Natl. Lib. of Med.

Shufelt et al., Hormone therapy dose, formulation, route delivery, and risk of cardiovascular events in women: findings from the Women's Health Initiative Observational Study, Menopause: The Journal of the North American Menopause Society, vol. 21, No. 3, 2014, pp. 1-7, 2013.

Stanczyk, F.Z. et al., "Percutaneous administration of progesterone: blood levels and endometrial protection," Menopause: The Journal of the North American Menopause Society, 2005, vol. 12, No. 2, pp. 232-237.

Stanczyk, F.Z., "Treatment of postmenopausal women with topical progesterone creams and gels: are they effective?" Climacteric 2014;17 (Suppl 2):8-11.

Stein, Emily A, et al., Progesterone Physical Properties, SciFinder, pp. 1-46, Feb. 24, 2014, American Chem. Society & US Natl. Lib. of Med.

Stephenson et al., "Transdermal progesterone: Effects on Menopausal symptoms and on thrombotic, anticoagulant, and inflammatory factors in postmenopausal women," Int J Pharmaceutical Compounding, vol. 12, No. 4, Jul./Aug. 2008, pp. 295-304.

USP, Monographs: Progesterone, USP29, www.pharmacopeia.cn/v29240/usp29nf24s0_m69870.html, search done: Feb. 25, 2014.

Waddell et al., Distribution and metabolism of topically applied progesterone in a rat model, Journal of Steroid Biochemistry & Molecular Biology 80 (2002) 449-455.

Wren et al., Effect of sequential transdermal progesterone cream on endometrium, bleeding pattern, and plasma progesterone and salivary progesterone levels in postmenopausal women, Climacteric, 2000, 3(3), pp. 155-160. http://dx.doi.org/10.1080/13697130008500109.

Zava, David T. et al., Percutaneous absorption of progesterone, Maturitas 77 (2014) 91-92, Elsevier.

Supplementary European Search Report dated Dec. 6, 2017 in foreign counterpart application No. EP15827543, 1 page.

\* cited by examiner

Mean ± SEM; n=8
* p=0.02 vs. Neg Control

Mean ± SD; n=8
* p=0.02 vs. Neg Control

Plasma

Salivary Gland

Uterus

TRANSDERMAL CREAM

CROSS-REFERENCES TO RELATED APPLICATIONS

This application claims priority to U.S. Provisional Pat. Appl. No. 62/030,540, filed on Jul. 29, 2014, and U.S. Provisional Pat. Appl. No. 62/152,674, filed on Apr. 24, 2015, which applications are incorporated herein by reference in their entirety.

BACKGROUND OF THE INVENTION

Hormone Replacement Therapy (HRT) is a medical treatment that involves the use of one or more of a group of medications designed to increase hormone levels in women who lack adequate hormone production. HRT can mitigate and prevent symptoms caused by diminished circulating estrogen and progesterone hormones in a pre-menopausal, peri-menopausal, menopausal, or post-menopausal subject.

Progesterone (CAS#57-83-0), also known as P4 (pregn-4-ene-3,20-dione), is a $C_{21}$ steroid hormone involved in the female menstrual cycle, pregnancy, and embryogenesis of humans and other species. Progesterone belongs to a class of hormones called progestogens, and is the major naturally occurring, endogenous human progestogen. The use of progesterone and its analogues has many medical applications, both to address acute conditions as well as the long-term decline of natural progesterone levels. Undesirable side effects exist due to irregular, inconsistent, or decreased hormone production in pre-, peri-, menopausal, and post-menopausal females. Progesterone is indicated for use in the prevention of endometrial hyperplasia in non-hysterectomized postmenopausal women who are receiving estrogen tablets. Progesterone is also indicated for use in secondary amenorrhea.

Estradiol (CAS#50-28-2), also known as 17β-estradiol, oestradiol, or E2, is found endogenously in the human body and is the primary female sex hormone. Estradiol contributes to regulation of estrous and menstrual reproduction cycles in females, development of reproductive tissues, and maintenance of bone tissue, among other processes. Estradiol deficiency in female subjects is implicated in conditions such as preterm birth, sleep disturbances, mood changes, vulvo-vaginal atrophy, and osteoporosis.

Existing topical transdermal compositions are formulated such that high dosages of hormones are administered, and they suffer from progesterone's limited absorption and bioavailability. Therefore, new transdermal pharmaceutical compositions for more effective delivery of progesterone and other hormones including estradiol are needed. The invention disclosed herein meets this and other needs.

BRIEF SUMMARY OF THE INVENTION

In one aspect, there is provided a transdermal pharmaceutical composition containing progesterone, a medium-chain oil, and d-limonene, wherein the pharmaceutical composition is formulated as a cream for topical administration. In certain embodiments, the pharmaceutical composition further includes estradiol.

In another aspect, there is provided a transdermal pharmaceutical composition comprising progesterone, a solubilizing agent containing a medium-chain oil, and a penetration enhancer, wherein the pharmaceutical composition is formulated as a cream for topical administration. In certain embodiments, the pharmaceutical composition further includes estradiol. In some embodiments, the pharmaceutical composition further includes d-limonene. In a related aspect, there is provided a transdermal pharmaceutical composition containing progesterone, a medium-chain oil, and one or more members selected from the group consisting of propylene glycol; a fatty acid ester of propylene glycol; and a glycol ether; wherein the pharmaceutical composition is formulated as a cream for topical administration. In some such some embodiments, the composition contains progesterone, a medium-chain oil, propylene glycol monolaurate, diethylene glycol monoethyl ether, and propylene glycol. In some such embodiments, the composition further comprises d-limonene.

In another aspect, there are provided methods for treating a condition associated with a hormone deficiency, such as progesterone deficiency or estradiol deficiency, in a subject. Such method include administering to the subject a transdermal pharmaceutical formulation as described herein.

DETAILED DESCRIPTION OF THE INVENTION

I. Introduction

Figure 1:
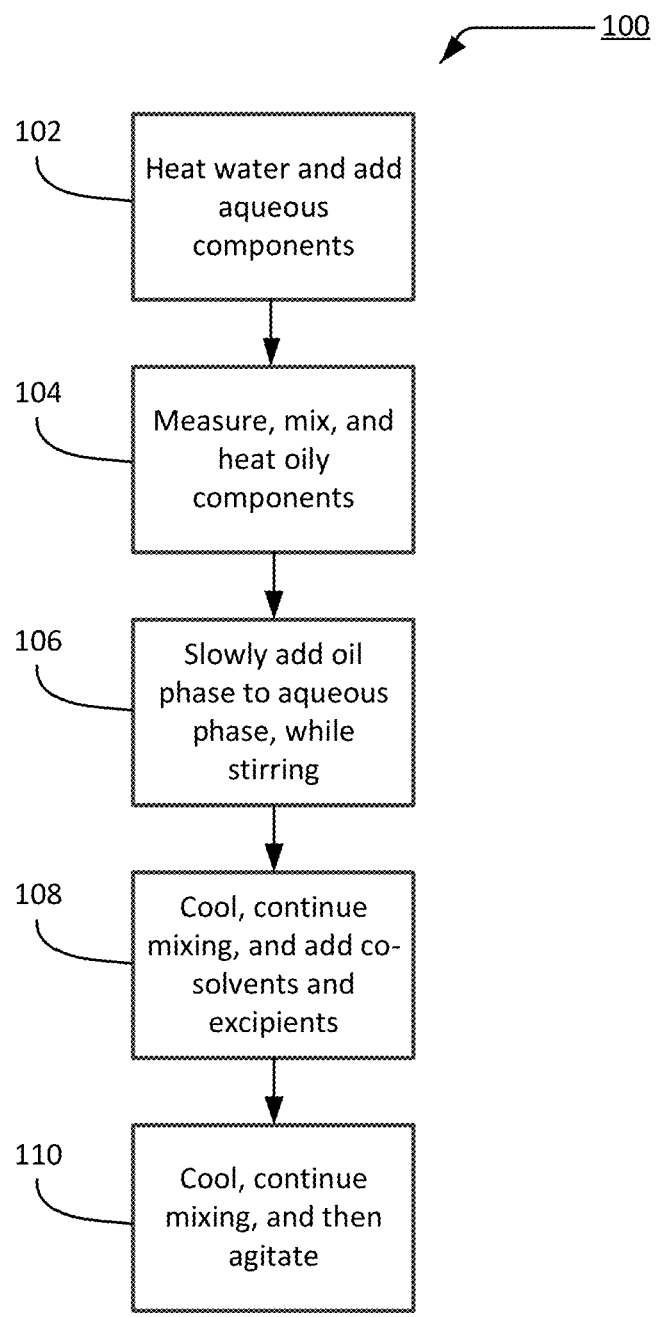
FIG. 1 shows a process for making the transdermal pharmaceutical formulations disclosed herein.

Provided herein are transdermal pharmaceutical cream compositions comprising solubilized or partially solubilized progesterone which are absorbed transdermally following application of the creams to the skin. The compositions can be absorbed and have their therapeutic effect locally, e.g., through skin or vaginal tissue and surrounding areas. Generally, the pharmaceutical compositions disclosed herein are useful in progesterone-deficient female subjects. The compositions can also be used in conjunction with treatment of estrogen deficiency. The creams disclosed herein exhibit excellent progesterone solubility and high progesterone flux in in vitro penetration models (Franz diffusion cell). The creams can minimize side effects associated with high doses, and provide increased bioavailability of progesterone applied topically to skin and other tissues. Surprisingly, the compositions described herein can be used to administer progesterone with lower levels of progesterone metabolism as compared to other modes of administration (e.g., via subcutaneous administration).

II. Definitions

As used herein, the term "pharmaceutical composition" refers to a mixture of an active pharmaceutical ingredient and at least one pharmaceutically acceptable excipient. The pharmaceutical compositions disclosed herein contain progesterone, optionally in combination with estradiol, as active pharmaceutical ingredients.

As used herein, the term "progesterone" refers to pregn-4-ene-3,20-dione. Progesterone is also interchangeably called P4 and is found endogenously in the human body. As used herein, progesterone refers to the bio-identical or body-identical form of progesterone found in the human body having the structure:

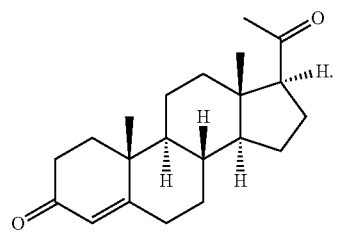

As used herein, the term "estradiol" refers to (17β)-estra-1,3,5(10)-triene-3,17-diol. Estradiol is also interchangeably called 17β-estradiol, oestradiol, or E2, and is found endogenously in the human body. As used herein, estradiol refers to the bio-identical or body-identical form of estradiol found in the human body having the structure:

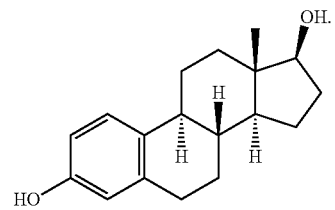

For the purposes of this disclosure, the anhydrous form or the hemihydrate form of estradiol can be substituted for one another by accounting for the water or lack of water according to well-known and understood techniques.

As used herein, the term "solubilizing agent" refers to an agent or combination of agents that solubilize or partially solubilize progesterone or estradiol. For example and without limitation, suitable solubilizing agents comprise medium-chain oils. Other solvents and co-solvents that solubilize or dissolve one or more active pharmaceutical ingredients, such as progesterone or estradiol, to a desirable extent can be also be included as part of the solubilizing agent. Solubilizing agents suitable for use in the formulations disclosed herein can contain pharmaceutical grade solubilizing agents (e.g., pharmaceutical grade medium-chain oils). It will be understood by those of skill in the art that other excipients or components can be added to or mixed with the solubilizing agent(s) to enhance the properties or performance of the solubilizing agent(s) or resulting formulation. Examples of such excipients include, but are not limited to, surfactants, emulsifiers, thickeners, colorants, etc.

As used herein, the term "medium-chain" refers to the aliphatic chain length of fatty acid containing molecules. "Medium-chain" specifically refers to fatty acids, fatty acid esters, or fatty acid derivatives that contain fatty acid aliphatic tails or carbon chains having between 6 (C6) and 14 (C14) carbon atoms.

The terms "medium-chain fatty acid" and "medium-chain fatty acid derivative" refer to fatty acids or fatty acid derivatives with aliphatic tails (i.e., carbon chains) having 6 to 14 carbons, including the ranges disclosed herein. Fatty acids consist of an unbranched aliphatic carbon chain, with at least one terminal carbon atom present in a carboxylic acid functional group. Fatty acid derivatives include, for example, fatty acid esters and fatty acid containing molecules, including, without limitation, mono-, di-, and triglycerides that include components derived from fatty acids, as well as fatty acid esters of ethylene glycol and propylene glycol. It will be understood by those of skill in the art that when more than one fatty acid ester is present in the backbone, such as a glycerol backbone, a propylene glycol backbone, a polyethylene glycol backbone, etc., the fatty acid esters may be the same or different. For instance, in a triglyceride, all three of the fatty acid esters can be the same, or two of the fatty acid esters can be the same and one can be different, or all three of the fatty acid esters can be different. In a diglyceride, the two fatty acid esters can either be the same or different. Regardless of whether the fatty acid esters are the same or different, substantially or predominantly all of the fatty acid esters will be medium chains. Those of skill will appreciate that the aliphatic tails can be saturated or unsaturated (having one or more double bonds between carbon atoms). In some embodiments, the aliphatic tails are saturated (i.e., having no double bonds between carbon atoms); examples include, without limitation, caproic acid, caprylic acid, capric acid, lauric acid, myristic acid, and derivatives thereof. Medium-chain fatty acids or medium-chain fatty acid derivatives include those with aliphatic carbon chains having 6-14 carbon atoms, including those that are C6-C14, C6-C12, C8-C14, C8-C12, C6-C10, C8-C10, or others.

As used herein, the term "oil" refers to any pharmaceutically acceptable oil, other than peanut oil, that can suspend or solubilize any suitable amount of progesterone or estradiol, starting material, or precursor, including micronized progesterone or estradiol as described herein.

As used herein, the term "medium-chain oil" refers to an oil wherein the composition of the fatty acid fraction of the oil is substantially medium-chain (i.e., C6 to C14) fatty acids, i.e., the composition profile of fatty acids in the oil is substantially medium-chain. The fatty acids in the fatty fraction of the oil can be present as free fatty acids or fatty acid esters. As used herein, "substantially" means that between 20% and 100% (inclusive of the upper and lower limits) of the fatty acid fraction of the oil is made up of medium-chain fatty acids, i.e., fatty acids with aliphatic carbon chains having 6 to 14 carbon atoms. In some embodiments, about 25%, about 30%, about 35%, about 40%, about 45%, about 50%, about 55%, about 60%, about 65%, about 70%, about 75%, about 80%, about 85%, about 90%, or about 95% of the fatty acid fraction of the oil is made up of medium-chain fatty acids. As used herein, "predominantly" means that greater than or equal to 50% of the fatty acid fraction of the oil is made up of medium-chain fatty acids, i.e., fatty acids with aliphatic carbon chains having 6 to 14 carbon atoms. Those of skill in the art that will readily appreciate that the terms "alkyl content" or "alkyl distribution" can be used in place of the term "fatty acid fraction" in characterizing a given oil, and these terms are used interchangeably herein. As such, medium-chain oils suitable for use in the formulations disclosed herein include medium-chain oils wherein the fatty acid fraction of the oil is substantially (or predominantly) medium-chain fatty acids, or medium-chain oils wherein the alkyl content or alkyl distribution of the oil is substantially (or predominantly) medium-chain alkyls (C6-C14 alkyls). It will be understood by those of skill in the art that the medium-chain oils suitable for use in the formulations disclosed herein are pharmaceutical grade. Examples of medium-chain oils include, for example and without limitation, medium-chain fatty acids, medium-chain fatty acid esters of glycerol (e.g., for example, mono-, di-, and triglycerides), medium-chain fatty acid esters of propylene glycol, medium-chain fatty acid derivatives of polyethylene glycol, and combinations thereof. It will be understood by those of skill in the art that the medium-chain oils used in the formulations disclosed herein can be a mixture of more than one medium-chain oil. Any mixture of medium-chain oils can be used provided that between 20% and 100% (inclusive of the upper and lower limits) of the fatty acid fraction of the mixture of medium-chain oils is made up of medium-chain fatty acids, i.e., fatty acids with aliphatic carbon chains having 6 to 14 carbon atoms. By way of example and without limitation, the medium-chain oil can be a mixture of MIGLYOL 812 (caprylic/capric triglycerides) and MIGLYOL 840 (propylene glycol dicaprylate/dicaprate), a mixture of CAPMUL MCM (caprylic/capric triglycerides) and MIGLYOL 812 (caprylic/capric triglycerides), a mixture of MIGLYOL 812, MIGLYOL 840 and Capmul MCM, etc.

As used herein, the term "medium-chain triglyceride" refers to a compound having a glycerol (i.e., propane-1,2,3-triol) backbone wherein each glycerol hydroxyl group is esterified with a medium-chain fatty acid as described herein. Examples of medium-chain triglycerides include, but are not limited to, caproic triglyceride, caprylic triglyceride, capric triglyceride, and lauric triglyceride. Medium-chain triglycerides can be mixed triglycerides having two or three different medium-chain fatty acid esters in the glycerol backbone.

As used herein, the term "d-limonene" refers to (4R)-1-methyl-4-(1-methylethenyl)-cyclohexene, which is also known by synonyms including (+)-4-isopropenyl-1-methyl-cyclohexe and (+)-p-mentha-1,8-diene.

As used herein, the term "diethylene glycol monoethyl ether" refers to 2-(2-ethoxyethoxy)ethanol, which is also known by synonyms including TRANSCUTOL®, CARBITOL™, and 3,6-dioxa-1-octanol, and pharmaceutically acceptable salts thereof.

As used herein, the term "propylene glycol monolaurate" refers to the monoester of dodecanoic acid with 1,2-propane diol, which is also known by synonyms including 1,2-propanediol monolaurate, propylene glycol monododecanoate, EMALEX PGML, RIKEMAL PL 100, and LAUROGLYCOL™ 90.

As used herein, the term "stearate" refers to stearic acid, i.e., octadecanoic acid, and esters thereof. Stearates include, but are not limited to, glycerol monostearate, sodium 1-methyl 9-(sulfooxy)stearate, pentaerythritol monostearate, PEG-10 stearate, PEG-14 stearate, PEG-40 stearate, PEG-2 stearate, PEG-3 stearate, PEG-4 stearate, PEG-150 stearate, PEG-6 stearate, PEG-8 stearate, PEG-8 stearate, PEG-75 stearate, PEG-75 distearate, PEG-3 distearate, PEG-6 distearate, PEG-8 distearate, PEG-2 distearate, PEG-4 distearate, PEG-12 distearate, PEG-20 distearate, PEG-32 distearate, and the like, as well as pharmaceutically acceptable salts thereof. A "stearate mixture" contains two or more of any of the stearates referred to herein. Examples of commercially available stearate mixtures include GELOT™ 64.

As used herein, the term "cetyl alcohol" refers to 1-hexadecanol, which is also known by synonyms including palmitoyl alcohol and n-hexadecyl alcohol. Cetyl alcohol derivatives include ethylene glycol and poly(ethylene glycol) ethers of cetyl alcohol including, but not limited to ceteth-2, ceteth-4, ceteth-20, ceteth-8-phosphate, PEG-13 cetyl ether carboxylic acid, and the like, as well as pharmaceutical salts thereof. A "cetyl alcohol mixture" contains cetyl alcohol and one or more cetyl alcohol derivatives as described herein. Alternatively, a cetyl alcohol mixture contains two or more cetyl alcohol derivatives as described herein. A "cetyl alcohol mixture" can also contain derivatives of stearyl alcohol (i.e., 1-octadecanol), such as an ethylene glycol or poly(ethylene glycol) ether of stearyl alcohol (e.g., steareth-3, steareth-20, and the like). Examples of commercially available cetyl alcohol mixtures include EMULCIRE™ 61.

As used herein, the term "carbomer" refers to refers to a crosslinked or non-crosslinked poly(acrylic acid) polymer or co-polymer. Examples of carbomers include, but are not limited to, CARBOPOL products such as CARBOPOL® 934, CARBOPOL® 940, CARBOPOL® 941, CARBOPOL® 980, CARBOPOL® 981, CARBOPOL® 1342, and CARBOPOL® 1382.

As used herein, the term "lecithin" refers to any lipid extract obtained from plant or animal tissue. Lecithin preparations can be obtained, for example, from soybeans, chicken eggs, and other sources. Lecithin typically contains numerous components including phospholipids, glycolipids, sphingolipids, and neutral lipids. Phosphatidylcholines (e.g., distearoyl-sn-phosphatidylcholine) typically make up the majority of most lecithin preparations. Lecithins can be chemically modified, such as via hydrogenation.

As used herein, the term "propylene glycol" refers to 1,2-propanediol, which is also known by synonyms including isopropylene glycol and methylethyl glycol.

As used herein, the term "methyl paraben" refers to 4-hydroxybenzoic acid methyl ester, which is also known by synonyms including methaben, methyl butex, and methyl p-hydroxybenzoate.

As used herein, the term "propyl paraben" refers to 4-hydroxybenzoic acid propyl ester, which is also known by synonyms including protaben, propyl butex, and propyl p-hydroxybenzoate.

As used herein the term, the term "citric acid" refers to 2-hydroxy-1,2,3-propanetricarboxylic acid and pharmaceutically acceptable salts or hydrates thereof. One of skill in the art will appreciate that other pharmaceutically acceptable acids can be used in place of citric acid in the compositions disclosed herein.

As used herein, the term "sodium phosphate" refers to a salt containing a sodium cation (i.e., $Na^+$) and a phosphate anion (i.e., $PO_4^{3-}$). A number of sodium phosphate salts and hydrates can be used in the compositions disclosed herein, including monosodium phosphate (dihydrate), disodium phosphate (anhydrous), and the like. One of skill in the art will appreciate that other pharmaceutically acceptable bases can be used in place of sodium phosphate in the compositions disclosed herein.

As used herein, the term "topical administration" refers to administration of a composition disclosed herein by contacting the skin or other tissue of a subject with the composition. Topical administration of the composition can also include removing the composition from the skin or tissue.

As used herein, the term "transdermal pharmaceutical composition" refers to a composition containing an active pharmaceutical ingredient that is delivered through the skin or other tissue of a subject upon topical administration.

As used herein, the terms "treatment" and "treating" refer to full or partial treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of symptoms. The treatment or amelioration of symptoms can be based on any objective or subjective parameter; including, e.g., the result of a physical examination.

As used herein, the term "cream" refers to a soft, semisolid, pharmaceutically and cosmetically acceptable preparation intended for external application to skin or other tissues. Creams typically include an aqueous base formulated as a water-in-oil emulsion or as an oil-in-water emulsion.

As used herein, the term "subject" refers to animals such as mammals, including, but not limited to, primates (humans and non-humans), cows, sheep, goats, horses, dogs, cats, rabbits, rats, mice, and the like. In various embodiments, the subject is a human, such as a woman with a uterus.

As used herein, the term "hormone deficiency" refers to a low level of one or more hormones in a subject. Normal hormone levels will vary from subject to subject and can be determined via known methods. Low hormone levels may or may not be associated with symptoms including, but not limited to, fatigue, irregular bleeding, lowered libido, and depression. Conditions associated with hormone deficiency include endometrial hyperplasia; endometriosis; secondary amenorrhea; preterm birth when the subject has a shortened cervix; menopause-related symptoms including, for example, vasomotor symptoms (e.g., hot flashes and night sweats); in relation to treatment of hypoestrogenism related symptoms including, for example and without limitation, vasomotor symptoms, sleep disturbances, mood changes, and vulvo-vaginal atrophy; and osteoporosis and other non-menopausal disease states or conditions treated with supplemental progesterone or estrogen.

As used herein, the terms "micronized progesterone" and "micronized estradiol" refer to crystalline progesterone or estradiol with an average particle size below 1 mm (e.g., below 500 μm or below 100 μm). In some embodiments, the micronized estradiol or micronized progesterone have an X50 particle size value below about 15 microns (μm) or having an X90 particle size value below about 25 microns. In some embodiments, the micronized progesterone or estradiol has an X90 particle size of less than 5 microns. The term "X50" means that one-half (50%) of the particles in a sample are smaller in diameter than a given number. For example, micronized progesterone having an X50 of 5 microns means that, for a given sample of micronized progesterone, one-half of the particles have a diameter of less than 5 microns. Similarly, the term "X90" means that ninety percent (90%) of the particles in a sample are smaller in diameter than a given number.

The term "about," as used herein to modify a numerical value, indicates a close range surrounding that explicit value. If "X" were the value, "about X" would indicate a value from 0.9X to 1.1X or a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X."

As used herein, the term "or" shall be understood to be defined as a logical disjunction (i.e., and/or) and shall not indicate an exclusive disjunction unless expressly indicated as such with the terms "either," "unless," "alternatively," and words of similar effect.

III. Transdermal Pharmaceutical Compositions

The pharmaceutical compositions disclosed herein contain progesterone in combination with substances that solubilize or partially solubilize the progesterone and promote its transdermal absorption. The compositions can further include estradiol combined with the progesterone. In some embodiments, there is provided a transdermal pharmaceutical composition comprising progesterone, a solubilizing agent containing a medium-chain oil, and a penetration enhancer, wherein the pharmaceutical composition is formulated as a cream for topical administration. In related embodiments, there is provided a transdermal pharmaceutical composition containing progesterone, a medium-chain oil, and one or more members selected from the group consisting of propylene glycol; a fatty acid ester of propylene glycol; and a glycol ether; wherein the pharmaceutical composition is formulated as a cream for topical administration. In some embodiments, the composition further includes a terpene. In some embodiments, the terpene is d-limonene.

In a related aspect, there is provided a transdermal pharmaceutical composition containing progesterone, a medium-chain oil, and a terpene penetration enhancer, wherein the pharmaceutical composition is formulated as a cream for topical administration. Various embodiments provide a transdermal pharmaceutical composition containing progesterone, a medium-chain oil, and d-limonene, wherein the pharmaceutical composition is formulated as a cream for topical administration.

The transdermal pharmaceutical compositions disclosed herein can contain any amount of progesterone suitable for treating a hormone deficiency. In certain embodiments, the transdermal pharmaceutical compositions contain from about 1.5% (w/w) to about 3.5% (w/w) progesterone, based on the total weight of a given composition. The compositions can contain, for example, from about 1.8% (w/w) to about 3.2% (w/w), or from about 2.1% (w/w) to about 2.9% (w/w), or from about 2.4% (w/w) to about 2.7% (w/w), or from about 1.5% (w/w) to about 2% (w/w), or from about 2% (w/w) to about 2.5% (w/w), or from about 2.5% (w/w) to about 3% (w/w), or from about 3% (w/w) to about 3.5% (w/w) progesterone. The compositions can contain about 1.5, 1.6, 1.7, 1.8, 1.9, 2.0, 2.1, 2.2, 2.3, 2.4, 2.5, 2.6, 2.7, 2.8, 2.9, or 3.0% (w/w) progesterone. In some embodiments, the transdermal pharmaceutical composition includes progesterone in an amount ranging from about 1.5% (w/w) to about 3.5% (w/w). In some embodiments, the transdermal pharmaceutical composition includes progesterone in an amount ranging from about 2% (w/w) to about 3% (w/w). Compositions disclosed herein can also contain progesterone in concentrations below 1.5% (w/w) and above 3% (w/w). In some embodiments, the compositions contain progesterone in an amount sufficient to provide a daily dose of progesterone ranging from about 0.1 mg to about 200 mg.

The transdermal pharmaceutical compositions disclosed herein can contain any amount of estradiol suitable for treating a hormone deficiency. In certain embodiments, the transdermal pharmaceutical compositions contain from about 0.001% (w/w) to about 0.5% (w/w) estradiol, based on the total weight of a given composition. In related embodiments, the transdermal pharmaceutical compositions contain about 0.005% (w/w) estradiol, or about 0.05% (w/w) estradiol, based on the total weight of a given composition. The compositions can contain, for example, from about 0.001% (w/w) to about 0.002% (w/w) estradiol, or from about 0.002% (w/w) to about 0.005% (w/w) estradiol, or from about 0.005% (w/w) to about 0.01% (w/w) estradiol, or from about 0.01% (w/w) to about 0.02% (w/w) estradiol, or from about 0.02% (w/w) to about 0.05% (w/w) estradiol, or from about 0.05% (w/w) to about 0.1% (w/w) estradiol, or from about 0.1% (w/w) to about 0.2% (w/w) estradiol, or from about 0.2% (w/w) to about 0.5% (w/w) estradiol, or from about 0.001% (w/w) to about 0.5% (w/w) estradiol, or from about 0.002% (w/w) to about 0.2% (w/w) estradiol, or from about 0.005% (w/w) to about 0.1% (w/w) estradiol, or from about 0.01% (w/w) to about 0.05% (w/w) estradiol, based on the total weight of the composition. In some embodiments, the compositions contain estradiol in an amount sufficient to provide a daily dose of estradiol ranging from about 0.5 mg to about 1.0 mg.

Pharmaceutical compositions disclosed herein can include solubilized progesterone or partially solubilized progesterone, wherein the progesterone or a portion thereof is solubilized or dissolved. In some embodiments, the progesterone is "partially solubilized" with a portion of the progesterone being solubilized or dissolved in the composition and a portion of the progesterone being suspended (i.e., a portion remains micronized) in the composition. Partially solubilized progesterone can include progesterone that is about 1% solubilized, about 5% solubilized, about 10% solubilized, about 15% solubilized, about 20% solubilized, about 25% solubilized, about 30% solubilized, about 35% solubilized, about 40% solubilized, about 45% solubilized, about 50% solubilized, about 55% solubilized, about 60% solubilized, about 65% solubilized, about 70% solubilized, about 75% solubilized, about 80% solubilized, about 85% solubilized, about 90% solubilized, or about 95% solubilized. In some embodiments, the progesterone is "fully solubilized" with all or about all of the progesterone being solubilized or dissolved. Fully solubilized progesterone can include progesterone that is about 96% solubilized, about 97% solubilized, about 98% solubilized, about 99% solubilized, or about 100% solubilized.

Compositions disclosed herein can include solubilized estradiol wherein the estradiol or a portion thereof is solubilized or dissolved. Solubilized estradiol can include estradiol that is about 1% solubilized, about 5% solubilized, about 10% solubilized, about 15% solubilized, about 20% solubilized, about 25% solubilized, about 30% solubilized, about 35% solubilized, about 40% solubilized, about 45% solubilized, about 50% solubilized, about 55% solubilized, about 60% solubilized, about 65% solubilized, about 70% solubilized, about 75% solubilized, about 80% solubilized, about 85% solubilized, about 90% solubilized, or about 95% solubilized. In some embodiments, the estradiol is "fully solubilized" with all or about all of the estradiol being solubilized or dissolved. Fully solubilized estradiol can include estradiol that is about 96% solubilized, about 97% solubilized, about 98% solubilized, about 99% solubilized or about 100% solubilized.

In some embodiments, one or both of the progesterone and estradiol are solubilized as described above. In some embodiments, either the estradiol, the progesterone, or both are fully solubilized as described above.

In various embodiments, progesterone and estradiol compositions disclosed herein are prepared via blending with a solubilizing agent. In certain embodiments, the solubilizing agent contains a pharmaceutically acceptable oil. In some embodiments, the solubilizing agent comprises a medium-chain oil. In some embodiments, the solubilizing agent contains a medium-chain oil made up substantially of C6-C14 medium-chains, e.g., at least 20%, at least 30%, at least 40%, at least 50%, at least 60%, at least 70%, at least 80%, or at least 90% of the fatty acid esters present in the oil are C6-C14. In some embodiments, the solubilizing agent contains a medium-chain oil made up substantially of C6-C12 medium-chain fatty acid esters, e.g., at least 20%, at least 30%, at least 40%, at least 50%, at least 60%, at least 70%, at least 80%, or at least 90% of the chains present in the oil are C6-C12. In some embodiments, the oil comprises at least one medium-chain mono-, di-, or triglyceride, or derivatives thereof, or combinations thereof. In some embodiments, the medium-chain oil comprises at least one medium-chain fatty acid propylene glycol monoester or diester; or at least one medium-chain fatty acid polyethylene glycol ester; or at least one medium-chain fatty acid glyceride monoester, diester, or triester. Fatty acid esters of the glycerol, propylene glycol, or polyethylene glycol can include, but are not limited to, esters of caproic acid (C6), enanthic acid (C7), caprylic acid (C8), pelargonic acid (C9), capric acid (C10), undecylic acid (C11), lauric acid (C12), tridecylic acid (C13), or myristic acid (C14), as well as combinations thereof. In some embodiments, the C6-C14 oils are unsaturated. In some embodiments, the solubilizing agent does not contain peanut oil.

In some embodiments, the solubilizing agent comprises a medium-chain oil having one or more mono-, di-, or triglycerides or combinations thereof. Exemplary glycerides include MIGLYOLs®, which are caprylic/capric triglycerides (SASOL Germany GMBH, Hamburg). MIGLYOLs include MIGLYOL 810 (caprylic/capric triglyceride), MIGLYOL 812 (caprylic/capric triglyceride), MIGLYOL 816 (caprylic/capric triglyceride), and MIGLYOL 829 (caprylic/capric/succinic triglyceride). The solubilizing agent can also comprise other caprylic/capric triglycerides, including, for example: caproic/caprylic/capric/lauric triglycerides; caprylic/capric/linoleic triglycerides; and caprylic/capric/succinic triglycerides. Exemplary caprylic/capric mono-, di-, or triglycerides include, but are not limited to, CAPMUL MCM, CAPMUL MCM C10, CAPMUL MCM C8, CAPMUL MCM C8 EP, and CAPMUL 708 G (the CAPMUL® brands are owned by ABITEC, Columbus, Ohio). Other mono-, di-, and triglycerides of fractionated vegetable fatty acids, and combinations or derivatives thereof can be used in the compositions disclosed herein. For example, the solubilizing agent can be 1,2,3-propanetriol (glycerol, glycerin, glycerine) esters of saturated coconut and palm kernel oil and derivatives thereof.

In some embodiments, commercially available fatty acid glycerol and glycol esters are prepared from natural oils and therefore may comprise components in addition to the fatty acid esters that predominantly comprise and characterize the solubilizing agent. Such other components may be, e.g., other fatty acid mono-, di-, and triglycerides, fatty acid mono- and diester ethylene or propylene glycols, free glycerols or glycols, or free fatty acids. For example, the Technical Data Sheet by ABITEC for CAPMUL MCM C8 describes CAPMUL MCM C8 as being composed of mono- and diglycerides of medium-chain fatty acids (mainly caprylic) and describes the alkyl content as ≤1% C6, ≥95% C8, ≤5% C10, and ≤1.5% C12 and higher. By way of further example, MIGLYOL 812 is described as a caprylic/capric triglyceride having a fatty acid composition with 65-80% caprylic (C8) acid and 20-35% capric (C10) acid. However, it can also contain small amounts of other fatty acids, e.g., a maximum of about 2% of caproic (C6) acid and lauric (C12) acid, and a maximum of about 1% myristic (C14) acid.

Any suitable amount of medium-chain oil can be used in the compositions disclosed herein. In general, the transdermal pharmaceutical compositions contain from about 10% (w/w) to about 30% (w/w). The compositions can contain, for example, from about 14% (w/w) to about 26% (w/w) medium-chain oil, or from about 18% (w/w) to about 22% (w/w) medium-chain oil, or from about 10% (w/w) to about 25% (w/w) medium-chain oil, or from about 10% (w/w) to about 20% (w/w) medium-chain oil, or from about 10% (w/w) to about 15% (w/w) medium-chain oil, or from about 15% (w/w) to about 20% (w/w) medium-chain oil, or from about 20% (w/w) to about 25% (w/w) medium-chain oil, or from about 25% (w/w) to about 30% (w/w) medium-chain oil. The compositions can contain about 10, 11, 12, 13, 14, 15, 16, 17, 18, 19, 20, 21, 22, 23, 24, 25, 26, 27, 28, 29 or 30% (w/w) medium-chain oil. In some embodiments, the transdermal pharmaceutical composition includes a medium-chain oil in an amount ranging from about 10% (w/w) to about 30% (w/w). In some embodiments, the transdermal pharmaceutical composition includes a medium-chain oil in an amount ranging from about 15% (w/w) to about 25% (w/w).

In some embodiments, the medium-chain oil includes a mixture of medium-chain triglycerides. In some embodiments, the mixture of medium-chain oils contains caprylic/capric triglycerides. Examples of mixtures of medium-chain triglycerides include MIGLYOL 812, MIGLYOL 840, etc.

In addition to a solubilizing agent, the compositions disclosed herein generally contain one or more penetration enhancers which promote the transdermal delivery of hormones through the skin. Examples of suitable penetration enhancers include, but are not limited to: alkyl methyl sulfoxides (such as dimethyl sulfoxide, decylmethyl sulfoxide, tetradecylmethyl sulfoxide, and the like); pyrrolidones (such as 2-pyrrolidone, N-methyl-2-pyrrolidone, N-(2-hydroxyethyl)-pyrrolidone, and the like); laurocapram; acetone; dimethyl acetamide; dimethyl formamide; tetrahydrofurfuryl alcohol; clofibric acid amides; hexamethylene lauramide; urea; N,N-diethyl-m-toluamide; propylene glycol; fatty acid esters of propylene glycol; fatty acid esters of polyethylene glycol; and glycol ethers.

Exemplary fatty acid esters of propylene and polyethylene glycol include, but are not limited to, propylene glycol monocaprylate (e.g., CAPMUL PG-8 or CAPMUL PG-8 NF); propylene glycol monocaprate (e.g., CAPMUL PG-10); propylene glycol monolaurate (e.g., CAPMUL PG-12 EP/NF, LAUROGLYCOL 90); propylene glycol dicaprylate; propylene glycol dicaprate; propylene glycol dicaprylate/dicaprate (e.g., MIGLYOL 840); and propylene glycol dilaurate (e.g., CAPMUL PG-2L EP/NF). Exemplary glycol ethers include, but are not limited to, 2-isopropoxyethanol, ethylene glycol monobutyl ether, and diethylene glycol monoethers (e.g., butoxydiglycol; dipropylene glycol methyl ether; diethylene glycol monoethyl ether, also referred to as 2-(2-ethoxyethoxy)ethanol and TRANSCUTOL®, GATTEFOSSÉ SAS, Saint-Priest, France; and the like).

In certain embodiments, the compositions disclosed herein contain a terpene or terpene derivative. Terpenes can improve the solubility of the progesterone and estradiol, preventing formation of crystals in the compositions. The terpenes can also act as penetration enhancers to promote the transdermal delivery of hormones through the skin. Terpenes are hydrocarbon compounds—often of biological origin—having carbon skeletons derived from isoprene (i.e., $CH_2=C(CH)_3CH=CH_2$). Carbon atoms in the terpene backbone can bear oxygen substituents such as hydroxyl, oxo, and carboxy groups. Terpenes include, but are not limited to, $C_5$ hemiterpenes, $C_{10}$ monoterpenes, $C_{15}$ sesquiterpenes, and $C_{20}$ diterpenes. Examples of specific terpenes include myrcene, ocimene, linalool, nerol, geraniol, citronellol, limonene, terpinene, phellandrene, cymene, ascardiole, pulegone, bisabolol, camphor, and pinene. In certain embodiments, the terpene is d-limonene (i.e., (4R)-1-methyl-4-(1-methylethenyl)-cyclohexene).

Propylene glycol, fatty acid esters of propylene glycol, glycol ethers, and combinations thereof can enhance penetration of progesterone and estradiol for delivery to targeted tissues in a subject. In some embodiments, the compositions disclosed herein contain progesterone, a medium-chain oil, and propylene glycol. In some embodiments, the composition contains progesterone, a medium-chain oil, propylene glycol, and a fatty acid ester of propylene glycol. In some embodiments, the composition contains progesterone, a medium-chain oil, and a fatty acid ester of propylene glycol. In some embodiments, the composition contains progesterone, a medium-chain oil, a fatty acid ester of propylene glycol, and a glycol ether. In some embodiments, the composition contains progesterone, a medium-chain oil, and a glycol ether. In some embodiments, the composition contains progesterone, a medium-chain oil, propylene glycol, a fatty acid ester of propylene glycol, and a glycol ether. In such embodiments, the compositions can also contain additional components including, but not limited to, a cetyl alcohol mixture, a stearate mixture, a carbomer, and lecithin. In some such embodiments, the compositions can also include a terpene such as d-limonene.

In some embodiments, propylene glycol, propylene glycol monolaurate, diethylene glycol monoethyl ether, and combinations thereof are used as penetration enhancers in the compositions disclosed herein. In some embodiments, the composition contains progesterone, a medium-chain oil, and propylene glycol. In some embodiments, the composition contains progesterone, a medium-chain oil, propylene glycol, and propylene glycol monolaurate. In some embodiments, the composition contains progesterone, a medium-chain oil, propylene glycol, and diethylene glycol monoethyl ether. In some embodiments, the composition contains progesterone, a medium-chain oil, and propylene glycol monolaurate. In some embodiments, the composition contains progesterone, a medium-chain oil, propylene glycol monolaurate, and diethylene glycol monoethyl ether. In some embodiments, composition contains progesterone, a medium-chain oil, and diethylene glycol monoethyl ether. In some embodiments, the composition contains progesterone, a medium-chain oil, propylene glycol, propylene glycol monolaurate, and diethylene glycol monoethyl ether. In some such embodiments, the compositions can also include a terpene such as d-limonene.

Any suitable amount of propylene glycol can be included in the transdermal compositions. For example, the compositions can contain from about 1% (w/w) to about 10% (w/w) propylene glycol, or from about 2% (w/w) to about 9% (w/w) propylene glycol, or from about 3% (w/w) to about 8% (w/w) propylene glycol, or from about 4% (w/w) to about 7% (w/w) propylene glycol, or from about 5% (w/w) to about 6% (w/w) propylene glycol. The compositions can contain from about 1% (w/w) to about 5% (w/w) propylene glycol, or from about 2% (w/w) to about 5% (w/w) propylene glycol, or from about 3% (w/w) to about 4% (w/w) propylene glycol. The compositions can contain about 1, 2, 3, 4, 5, 6, 7, 8, 9, or about 10% (w/w) propylene glycol.

Any suitable amount of a fatty acid ester of propylene glycol can be included in the transdermal compositions. For example, the compositions can contain from about 1% (w/w) to about 10% (w/w) fatty acid ester of propylene glycol, or from about 2% (w/w) to about 9% (w/w) fatty acid ester of propylene glycol, or from about 3% (w/w) to about 8% (w/w) fatty acid ester of propylene glycol, or from about 4% (w/w) to about 7% (w/w) fatty acid ester of propylene glycol, or from about 5% (w/w) to about 6% (w/w) fatty acid ester of propylene glycol. The compositions can contain from about 2% (w/w) to about 7% (w/w) fatty acid ester of propylene glycol, or from about 3% (w/w) to about 6% (w/w) fatty acid ester of propylene glycol. The compositions can contain about 1, 2, 3, 4, 5, 6, 7, 8, 9, or about 10% (w/w) fatty acid ester of propylene glycol. In some such embodiments, the fatty acid ester of propylene glycol is propylene glycol monolaurate.

Any suitable amount of glycol ether can be included in the transdermal compositions. For example, the compositions can contain from about 1% (w/w) to about 10% (w/w) glycol ether, or from about 1% (w/w) to about 5% (w/w) glycol ether, or from about 2% (w/w) to about 4% (w/w) glycol ether. The compositions can contain about 1, 2, 3, 4, 5, 6, 7, 8, 9, or about 10% (w/w) glycol ether. In some such embodiments, the glycol ether is diethylene glycol monoethyl ether.

The transdermal pharmaceutical compositions disclosed herein can contain any suitable amount of a terpene, such as d-limonene. In general, the compositions contain from about 1% (w/w) to about 12% (w/w) d-limonene. The compositions can contain, for example, from about 2% (w/w) to about 10% (w/w) d-limonene, or from about 1% (w/w) to about 4% (w/w) d-limonene, or from about 4% (w/w) to about 8% (w/w) d-limonene, or from about 8% (w/w) to about 12% (w/w) d-limonene, or from about 1% (w/w) to about 5% (w/w) d-limonene, or from about 5% (w/w) to about 10% (w/w) d-limonene. The compositions can contain from about 2% (w/w) to about 8% (w/w) d-limonene, or from about 3% (w/w) to about 7% (w/w) d-limonene, or from about 4% (w/w) to about 6% (w/w) d-limonene. The compositions can contain about 1, 1.5, 2, 2.5, 3, 3.5, 4, 4.5, 5, 5.5, 6, 6.5, 7, 7.5, 8, 8.5, 9, 9.5, 10, 10.5, 11, 11.5, or 12% (w/w) d-limonene. In some embodiments, the transdermal pharmaceutical composition includes d-limonene in an amount ranging from about 1% (w/w) to about 12% (w/w). In some embodiments, the transdermal pharmaceutical composition includes d-limonene in an amount ranging from about 1.5% (w/w) to about 10% (w/w).

In some embodiments, the transdermal pharmaceutical composition includes progesterone in an amount ranging from about 1.5% (w/w) to about 3.5% (w/w); and a medium-chain oil in an amount ranging from about 10% (w/w) to about 30% (w/w). In some embodiments, the transdermal pharmaceutical composition includes progesterone in an amount ranging from about 1.5% (w/w) to about 3.5% (w/w); a medium-chain oil in an amount ranging from about 10% (w/w) to about 30% (w/w); and d-limonene in an amount ranging from about 1% (w/w) to about 12% (w/w).

In some embodiments, the transdermal pharmaceutical composition includes progesterone in an amount ranging from about 2% (w/w) to about 3% (w/w); and a medium-chain oil in an amount ranging from about 15% (w/w) to about 25% (w/w). In some embodiments, the transdermal pharmaceutical composition includes progesterone in an amount ranging from about 2% (w/w) to about 3% (w/w); a medium-chain oil in an amount ranging from about 15% (w/w) to about 25% (w/w); and d-limonene in an amount ranging from about 1.5% (w/w) to about 10% (w/w).

In some embodiments, the transdermal pharmaceutical composition includes progesterone in an amount of about 2.5% (w/w) and a medium-chain oil in an amount of about 15% (w/w). In some embodiments, the transdermal pharmaceutical composition includes progesterone in an amount of about 2.5% (w/w); a medium-chain oil in an amount of about 15% (w/w); and d-limonene in an amount of about 5% (w/w).

In some embodiments, the transdermal pharmaceutical composition further includes estradiol. In some embodiments, the transdermal pharmaceutical composition includes estradiol in an amount ranging from about 0.001% (w/w) to about 0.5% (w/w). In some embodiments, the transdermal pharmaceutical composition includes estradiol in an amount ranging from about 0.01% (w/w) to about 0.1% (w/w). In some embodiments, the transdermal pharmaceutical composition includes estradiol in an amount of about 0.005% (w/w). In some embodiments, the transdermal pharmaceutical composition includes estradiol in an amount of about 0.05% (w/w).

The compositions disclosed herein can further contain any of the excipients used in known transdermal hormone compositions, including but not limited to those described in U.S. Pat. Nos. 5,453,279; 6,056,972; 6,238,284; and 7,404,965; each of which is incorporated herein by reference in its entirety. In some embodiments, the compositions can also contain additional components including, but not limited to, a cetyl alcohol mixture, a stearate mixture, a carbomer, and lecithin. The compositions can also contain additional components and excipients including, but not limited to, non-ionic or ionic surfactants, emulsifiers, colorants, preservatives, antioxidants, etc. as described herein.

In some embodiments, the pharmaceutical composition further comprises one or more non-ionic or ionic surfactants. In some embodiments, the non-ionic surfactant is selected from one or more of glycerol and polyethylene glycol esters of medium-chain fatty acids or long chain fatty acids, for example, lauroyl macrogol-32 glycerides or lauroyl polyoxyl-32 glycerides, commercially available as GELUCIRE®, including, for example, GELUCIRE® 39/01 (glycerol esters of saturated C12-C18 fatty acids); GELUCIRE® 43/01 (hard fat NF/JPE); GELUCIRE® 44/14 (lauroyl macrogol-32 glycerides EP, lauroyl polyoxyl-32 glycerides NF, lauroyl polyoxylglycerides (USA FDA IIG)); and GELUCIRE® 50/13 (stearoyl macrogol-32 glycerides EP, stearoyl polyoxyl-32 glycerides NF, stearoyl polyoxylglycerides (USA FDA IIG)).

In some embodiments, non-ionic surfactants include, for example and without limitation: one or more of oleic acid, linoleic acid, palmitic acid, and stearic acid. In some embodiments, non-ionic surfactants comprise polyethylene sorbitol esters, including polysorbate 80, which is commercially available under the trademark TWEEN® 80 (Sigma Aldrich, St. Louis, Mo.). Polysorbate 80 comprises approximately 60%-70% oleic acid with the remainder comprising primarily linoleic acids, palmitic acids, and stearic acids.

In some embodiments, non-ionic surfactants include PEG-6 palmitostearate and ethylene glycol palmitostearate, which are available commercially as TEFOSE® 63 (GATTEFOSSÉ SAS, Saint-Priest, France) which can be used with, for example, CAPMUL MCM having ratios of MCM to TEFOSE® 63 of, for example, 8:2 or 9:1. Other exemplary solubilizing agents/non-ionic surfactants combinations include, without limitation: MIGLYOL 812:GELUCIRE® 50/13 or MIGLYOL 812:TEFOSE® 63.

A non-ionic or ionic surfactant may be used at concentrations greater than about 0.01%, for example at a concentration of about 0.01%-30.0%, about 0.1% to 10.0%, or about 1% to 10.0%, from 10% to 30%. In some embodiments, the pharmaceutical composition comprises about 10.0% surfactant by weight. In some embodiments, the pharmaceutical composition comprises about 15.0% surfactant by weight. In some embodiments, the pharmaceutical composition comprises about 0.1% to about 5.0% surfactant by weight, e.g., about 1.0 wt %. In some embodiments, the pharmaceutical composition comprises about 5.0% to about 15.0% surfactant by weight. In some embodiments, the pharmaceutical composition comprises about 10.0% to about 20.0% surfactant by weight. In some embodiments, the pharmaceutical composition comprises less than 30.0%, less than 29.0%, less than 28.0%, less than 27.0%, less than 26.0%, less than 25.0%, less than 24.0%, less than 23.0%, less than 22.0%, less than 21.0%, less than 20.0%, less than 19.0%, less than 18.0%, less than 17.0%, less than 16.0%, less than 15.0%, less than 14.0%, less than 13.0%, less than 12.0%, less than 11.0%, less than 10.0%, less than 9.0%, less than 8.0%, less than 7.0%, less than 6.0%, less than 5.0%, less than 4.0%, less than 3.0%, less than 2.0%, or less than 1.0% surfactant by weight.

Surfactants as described above can serve as emulsifiers in the compositions disclosed herein. Suitable emulsifiers include, but are not limited to, sorbitan esters (also referred to as Span™), polyoxyethylene sorbitan esters (also referred to as polysorbates; Tween™), and glyceryl esters. Examples of sorbitan esters include, but are not limited to, sorbitan monooleate, sorbitan monostearate, sorbitan monolaurate, sorbitan trioleate, and sorbitan tristearate. Examples of polyoxyethylene sorbitan esters include polyethylene glycol (PEG) sorbitan esters such as PEG-(5)-sorbitan monooleate, PEG-(4)-sorbitan monostearate, PEG-(4)-sorbitan monolaurate, PEG-sorbitan trioleate, and PEG-sorbitan tristearate. Examples of glyceryl esters include glyceryl monostearate, glyceryl monolaurate, and glyceryl tristearate.

Other emulsifiers that can be used in the present invention include lecithin, cholesterol, phosphatidylglycerols, alkyl alcohols, poloxamers (also referred to as Pluronic™/Synperonic™), poloxamin (also referred to as Tetronic™), sodium laurylsulfate, sodium cetylstearylsulfate, and potassium oleate.

In some embodiments, the pharmaceutical composition further comprises one more other excipients, such as—but not limited to—colorants, scents, preservatives, antioxidants, texture modifiers, viscosity (rheology) modifiers, or buffers. The choice of excipients will, to a large extent, depend on factors such as the effect of the excipients on solubility and stability of the components in the cream formulation. Colorants, for example, can be used in an amount ranging from about 0.1% to about 2% by weight. Preservatives, for example, can be used in an amount ranging from about 0.002% to about 0.05% by weight, such as from about 0.005% to about 0.05% by weight or from about 0.002% to about 0.02% by weight. Preservatives can include, but are not limited to, methyl and propyl paraben in a ratio of about 10:1. Those of skill in the art will know how to select particular excipients and quantities thereof based on factors including the amount of the hormones in a particular composition and the intended mode of administration.

In some embodiments, the pharmaceutical composition further comprises one or more phenolic aldehyde(s). Phenolic aldehydes used herein include, but are not limited to, vanillin (4-hydroxy-3-methoxybenzaldehyde), methylvanillin, and ethylvanillin (3-ethoxy-4-hydroxybenzaldehyde, bourbonal).

In some embodiments, the pharmaceutical composition further comprises one or more antioxidants. Examples of suitable antioxidants include, but are not limited to, butylated hydroxytoluene (BHT), butylated hydroxyanisole, tert-butyl hydroquinone, propyl gallate, octyl gallate, dodecyl gallate, ascorbic acid, ascorbyl palmitate, erythorbic acid, 4-hexylresorcinol, α-tocopherol, β-tocopherol, γ-tocopherol, δ-tocopherol, and mixtures thereof. In some embodiments, the antioxidant is BHT. Inclusion of BHT can prevent oxidation of d-limonene during storage and use of the compositions.

In some embodiments, the pharmaceutical composition further comprises one or more gelling agents. Suitable gelling agents include, but are not limited to, cellulose derivatives, polyacrylic acid derivatives, and gums. Examples of cellulose derivatives include methylcellulose, ethylcellulose, hydroxyethyl cellulose, and carboxymethyl cellulose. Examples of polyacrylic acid derivatives include polyacrylic acid, polymethylacrylate, and polyethylacrylate. Examples of polyacrylic acid derivatives further include crosslinked polyacrylates (e.g., CARBOPOL 980® NF Polymer, LUBRIZOL, Wickliffe, Ohio). Examples of gums include agar, alginic acid, glucomannan, arabic gum, sodium alginate, and tragacanth. Gelling agents can be used to raise the viscosity of a pharmaceutical composition to ensure that the composition is cosmetically elegant and has suitable flow characteristics for its intended use.

In certain embodiments, a buffer system is added to achieve or maintain a desired pH in the pharmaceutical composition. Buffer systems are well known to persons of ordinary skill in the art, and any buffer system suitable for pharmaceutical products and appropriate for the given pharmaceutical composition can be used. In embodiments, the buffer system can be a combination of citric acid and dibasic sodium phosphate. Typically, purified water is added to bring the pharmaceutical composition to the final weight.

Generally, the solubilizing agents, penetration enhancers, surfactants, and excipients used in the pharmaceutical compositions described herein are non-toxic, pharmaceutically acceptable, compatible with each other, and maintain stability of the pharmaceutical composition and the various components with respect to each other. Additionally, the combination of various components that comprise the pharmaceutical compositions will result in the desired therapeutic effect when administered to a subject.

Accordingly, in some embodiments the transdermal pharmaceutical composition includes: progesterone in an amount of about 2.5% (w/w); a medium-chain oil in an amount of about 15% (w/w), the medium-chain oil comprising medium-chain triglycerides (e.g., caprylic triglyceride and capric triglyceride); d-limonene in an amount of about 5% (w/w); diethylene glycol monoethyl ether in an amount of about 3% (w/w); propylene glycol monolaurate in an amount of about 5% (w/w); a stearate mixture in an amount of about 7% (w/w), the stearate mixture comprising glycerol monostearate and PEG-75 stearate; a cetyl alcohol mixture in an amount of about 3.5% (w/w), the cetyl alcohol mixture comprising cetyl alcohol, ceteth-20, and steareth-20; a carbomer in an amount of about 0.2% (w/w); lecithin in an amount of about 3.% (w/w); propylene glycol in an amount of about 4.% (w/w); methyl paraben in an amount of about 0.2% (w/w); propyl paraben in an amount of about 0.02% (w/w); citric acid in an amount of about 0.5% (w/w); sodium phosphate in an amount of about 0.8% (w/w); and purified water in an amount of about 50.3% (w/w). In some embodiments, the transdermal pharmaceutical composition further comprises butylated hydroxytoluene in a mount of about 0.1% (w/w). In certain embodiments, the transdermal pharmaceutical composition further includes estradiol in an amount of about 0.05% (w/w). In certain embodiments, the transdermal pharmaceutical composition further includes estradiol in an amount of about 0.005% (w/w). In certain embodiments, the transdermal pharmaceutical composition further includes estradiol in an amount of about 0.06% (w/w). One of skill in the art will appreciate that when further components such as butylated hydroxytoluene and estradiol are added to a composition, the amount of water in the composition can be adjusted to maintain the same relative % w/w.

In some embodiments, the transdermal pharmaceutical composition includes: progesterone in an amount of about 2.5% (w/w); a medium-chain oil in an amount of about 15% (w/w), the medium-chain comprising a medium-chain triglyceride (such as caprylic/capric triglyceride); diethylene glycol monoethyl ether in an amount of about 3% (w/w); propylene glycol monolaurate in an amount of about 5% (w/w); a stearate mixture in an amount of about 7% (w/w), the stearate mixture comprising glycerol monostearate and PEG-75 stearate; a cetyl alcohol mixture in an amount of about 3.5% (w/w), the cetyl alcohol mixture comprising cetyl alcohol, ceteth-20, and steareth-20; a carbomer in an amount of about 0.2% (w/w); lecithin in an amount of about 3% (w/w); propylene glycol in an amount of about 4% (w/w); methyl paraben in an amount of about 0.2% (w/w); propyl paraben in an amount of about 0.02% (w/w); citric acid in an amount of about 0.5% (w/w); sodium phosphate in an amount of about 0.8% (w/w); and purified water in an amount of about 55.3% (w/w). In some such embodiments, the composition further includes estradiol in an amount of about 0.05% (w/w). In some such embodiments, the composition further includes estradiol in an amount of about 0.005% (w/w). In some such embodiments, the composition further includes estradiol in an amount of about 0.06% (w/w).

In some embodiments, the transdermal pharmaceutical composition includes: progesterone in an amount of about 2.5% (w/w); a medium-chain oil in an amount of about 15% (w/w), the medium-chain comprising a medium-chain triglyceride (such as caprylic/capric triglyceride); diethylene glycol monoethyl ether in an amount of about 3% (w/w); propylene glycol monolaurate in an amount of about 5% (w/w); butylated hydroxytoluene in an amount of about 0.1% (w/w); a stearate mixture in an amount of about 7% (w/w), the stearate mixture comprising glycerol monostearate and PEG-75 stearate; a cetyl alcohol mixture in an amount of about 3.5% (w/w), the cetyl alcohol mixture comprising cetyl alcohol, ceteth-20, and steareth-20; a carbomer in an amount of about 0.2% (w/w); lecithin in an amount of about 3% (w/w); propylene glycol in an amount of about 4% (w/w); methyl paraben in an amount of about 0.2% (w/w); propyl paraben in an amount of about 0.02% (w/w); citric acid in an amount of about 0.5% (w/w); sodium phosphate in an amount of about 0.8% (w/w); and purified water in an amount of about 55.2% (w/w).

Compositions according to the invention include, but are not limited to, Compositions I-IV as set forth in Table 1A and compositions A-J as set forth in Table 1B.

TABLE IA

Exemplary Hormone Compositions

| Component | Composition I % (w/w) | II % (w/w) | III % (w/w) | IV % (w/w) |
|---|---|---|---|---|
| Progesterone Micronized, USP | 2.5 | 2.5 | 2.5 | 2.5 |
| Micronized Estradiol Hemihydrate, USP | | | 0.005 | 0.005 |
| Medium Chain Triglycerides, NF (MIGLYOL 812) | 15 | 15 | 14.9 | 14.9 |
| d-Limonene | 5 | | 5 | |
| Diethylene Glycol Mono Ethyl Ether EP/NF(TRANSCUTOL P) | 3 | 3 | 3 | 3 |
| Propylene Glycol Monolaurate (Type II) EP/NF, (LAUROGLYCOL 90) | 5 | 5 | 5.4 | 5.4 |
| Mixture of Glycerol monostearate EP/NF and PEG-75 stearate NF/JPE, (GELOT 64) | 7 | 7 | 7 | 7 |
| Mixture of Cetyl Alcohol EP/NF and Ethoxylated Fatty Alcohols (Ceteth-20, Steareth-20) EP/NF, (EMULCIRE 61 WL 2659) | 3.5 | 3.5 | 3.5 | 3.5 |
| CARBOPOL 980 NF Polymer | 0.2 | 0.2 | 0.2 | 0.2 |
| Liquid Soy Lecithin | 3 | 0.3 | 3 | 3 |
| Propylene Glycol, USP | 4 | 4 | 4 | 4 |
| Methyl Paraben, NF | 0.2 | 0.2 | 0.2 | 0.2 |
| Propyl Paraben, NF, EP, BP, JP | 0.02 | 0.02 | 0.02 | 0.02 |
| Citric Acid Monohydrate, Granular, USP | 0.47 | 0.53 | 0.47 | 0.53 |
| Dibasic Sodium Phosphate, Dried, USP | 0.82 | 0.92 | 0.82 | 0.92 |
| Purified Water, USP | QS | QS | QS | QS |
| Total | 100 | 100 | 100 | 100 |

TABLE 1B

Exemplary Hormone Compositions

| Component | Composition A % w/w | B % w/w | C % w/w | D % w/w | E % w/w | F % w/w |
|---|---|---|---|---|---|---|
| Progesterone Micronized USP | 2.5 | 2.5 | 2.5 | 2.5 | | |
| Micronized Estradiol Hemihydrate, USP | | 0.005 | 0.005 | | 0.005 | 0.005 |
| Medium Chain Triglycerides, NF (MIGLYOL 812) | 15 | 15 | 15 | 15 | 15 | 15 |
| d-Limonene (High Purity Terpenes, 99) | 5 | | 5 | | 5 | |
| Diethylene Glycol Mono Ethyl Ether EP/NF (TRANSCUTOL P) | 3 | 3 | 3 | 3 | 3 | 3 |
| Propylene Glycol Monolaurate (Type II) EP/NF (LAUROGLYCOL 90) | 5 | 5 | 5 | 5 | 5 | 5 |
| Butylated Hydroxytoluene, Granular, NF | 0.1 | 0.1 | 0.1 | 0.1 | 0.1 | 0.1 |
| Mixture of Glycerol monostearate EP/NF and PEG-75 stearate NF/JPE (GELOT 64) | 7 | 7 | 7 | 7 | 7 | 7 |
| Mixture of Cetyl Alcohol EP/NF and Ethoxylated Fatty Alcohols (Ceteth-20, Steareth-20) EP/NF (EMULCIRE 61 WL 2659) | 3.5 | 3.5 | 3.5 | 3.5 | 3.5 | 3.5 |
| CARBOPOL 980 NF Polymer | 0.2 | 0.2 | 0.2 | 0.2 | 0.2 | 0.2 |
| Liquid Soy Lecithin | 3 | 3 | 3 | 3 | 3 | 3 |
| Propylene Glycol, USP | 4 | 4 | 4 | 4 | 4 | 4 |
| Methylparaben, NF | 0.2 | 0.2 | 0.2 | 0.2 | 0.2 | 0.2 |
| Propylparaben, NF, EP, BP | 0.02 | 0.02 | 0.02 | 0.02 | 0.02 | 0.02 |

TABLE 1B-continued

| Exemplary Hormone Compositions | | | | | | |
|---|---|---|---|---|---|---|
| Citric Acid Monohydrate, Granular, USP | 0.47 | 0.47 | 0.47 | 0.47 | 0.47 | 0.47 |
| Dibasic Sodium Phosphate, Dried, USP | 0.82 | 0.82 | 0.82 | 0.82 | 0.82 | 0.82 |
| Purified Water, USP | 50.19 | 55.19 | 50.19 | 55.19 | 52.69 | 57.69 |
| TOTAL | 100 | 100 | 100 | 100 | 100 | 100 |

| | Composition | | | |
|---|---|---|---|---|
| | G | H | I | J |
| Component | % w/w | % w/w | % w/w | % w/w |
| Progesterone Micronized USP | 2.5 | 2.5 | | |
| Micronized Estradiol Hemihydrate, USP | 0.05 | 0.05 | 0.05 | 0.05 |
| Medium Chain Triglycerides, NF (MIGLYOL 812) | 15 | 15 | 15 | 15 |
| d-Limonene (High Purity Terpenes, 99) | 5 | | 5 | |
| Diethylene Glycol Mono Ethyl Ether EP/NF (TRANSCUTOL P) | 3 | 3 | 3 | 3 |
| Propylene Glycol Monolaurate (Type II) EP/NF (LAUROGLYCOL 90) | 5 | 5 | 5 | 5 |
| Butylated Hydroxytoluene, Granular, NF | 0.1 | 0.1 | 0.1 | 0.1 |
| Mixture of Glycerol monostearate EP/NF and PEG-75 stearate NF/JPE (GELOT 64) | 7 | 7 | 7 | 7 |
| Mixture of Cetyl Alcohol EP/NF and Ethoxylated Fatty Alcohols (Ceteth-20, Steareth-20) EP/NF (EMULCIRE 61 WL 2659) | 3.5 | 3.5 | 3.5 | 3.5 |
| CARBOPOL 980 NF Polymer | 0.2 | 0.2 | 0.2 | 0.2 |
| Liquid Soy Lecithin | 3 | 3 | 3 | 3 |
| Propylene Glycol, USP | 4 | 4 | 4 | 4 |
| Methylparaben, NF | 0.2 | 0.2 | 0.2 | 0.2 |
| Propylparaben, NF, EP, BP | 0.02 | 0.02 | 0.02 | 0.02 |
| Citric Acid Monohydrate, Granular, USP | 0.47 | 0.47 | 0.47 | 0.47 |
| Dibasic Sodium Phosphate, Dried, USP | 0.82 | 0.82 | 0.82 | 0.82 |
| Purified Water, USP | 50.145 | 55.145 | 52.645 | 57.645 |
| TOTAL | 100 | 100 | 100 | 100 |

The transdermal pharmaceutical cream compositions disclosed herein provide for higher hormone solubility and improved bioavailability as compared to existing commercial cream compositions. In certain embodiments, progesterone and estradiol are substantially or fully solubilized, resulting in efficient delivery through the skin or other tissues such as mucosal (e.g., vaginal) tissue. In certain embodiments, the hormones can be administered over a larger surface area than other known formulations. Because higher solubility and improved bioavailability are achieved, lower dose administrations are also achieved. With lower dose administrations the overall safety is improved by reducing the side effects resulting from high dosages of administered progesterone. In addition, the cream compositions are soothing to irritated skin or vaginal tissue, are easily applied, have a pleasing glossy appearance, and exhibit minimal emulsion separation during storage or upon application.

A general method 100 to prepare pharmaceutical cream compositions of this disclosure is outlined in FIG. 1, and comprises processes 102-110, below.

Process 102 comprises heating appropriate amount of water to about 65° C.-75° C. According to embodiments, water comprises 0.1 M citric acid and 0.2 M $Na_2HPO_4$ solution. Components making up the aqueous phase (i.e., components with aqueous solubility; e.g., carbomer) are added to the water and mixed until completely dispersed and uniform.

Process 104 comprises measuring or weighing out into an appropriate container the oil phase components (e.g., MIGLYOL 812, CREMOPHOR® A6 and A25, Cetyl alcohol). Components are heated to about 65° C.-75° C. In some embodiments, within process 104 the progesterone, estradiol, or combination thereof is added and mixed until dissolved (or in some embodiments partially suspended and partially solubilized)

Once both oil and aqueous phases attain the desired temperature, process 106 comprises removing both phases from the heat source. Then, the oil phase is slowly added to the aqueous phase while stirring at about 1200 RPM. Stirring is continued until the temperature of the pharmaceutical cream composition is ≤40° C.

Process 108 comprises waiting until the pharmaceutical cream composition temperature is ≤40° C., and then adding further components (e.g., TRANSCUTOL®, d-limonene, LAUROGLYCOL® 90, etc.) to the composition. Mixing is continued until the temperature of pharmaceutical cream composition is ≤25° C.

Process 110 comprises agitating the pharmaceutical cream composition using an appropriate agitator known in the art for an adequate amount of time, for example 2-5 minutes.

Because a composition may contain additional or fewer excipients as compared to another composition of this disclosure, the general method of manufacture below varies according to the different excipients, surfactants, or ingredients contained in the respective pharmaceutical cream composition. Finished formulations can be packaged for use in a number of convenient containers, such as tubes, single-use sachets, metered-dose pumps, and the like.

Figure 2:
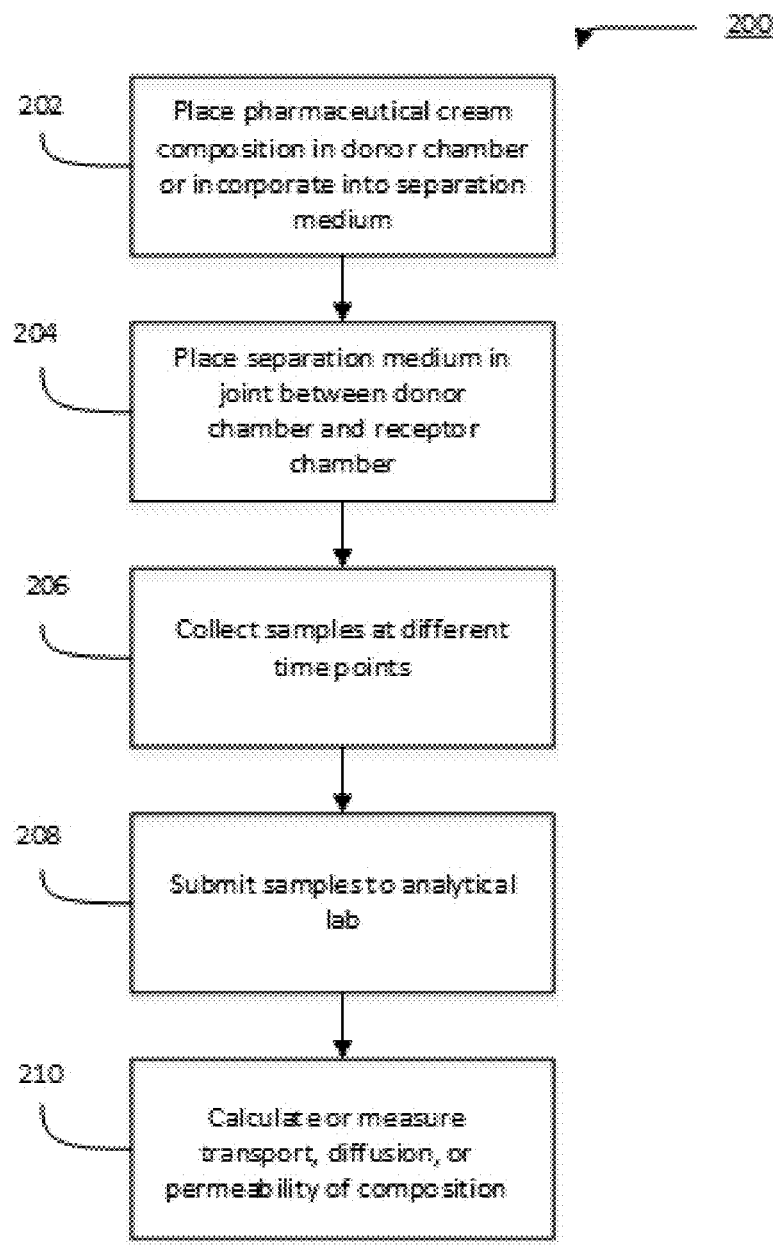
FIG. 2 shows a process for testing the transdermal pharmaceutical formulations disclosed herein.

A method 200 for determining the hormone transport properties of the compositions described herein is outlined in FIG. 2. A Franz diffusion cell is employed according to method 200. A Franz diffusion cell generally consists of a donor chamber and a receptor chamber, which are connected by a joint. Process 202 comprises placing an appropriate amount of a composition in the donor chamber, or on—or incorporated into—a medium separating the donor chamber and the receptor chamber (e.g., 0.7 g of progesterone cream). The receptor phase is maintained at an appropriate temperature (e.g., 37° C.), the volume of the receptor chamber is 5.0 mL, and the sample volume is 2.0 mL. The receptor phase typically contains an aqueous solution with optional additives such as 5% sodium lauryl sulfate (SLS).

Process 204 comprises placing the separation medium in the joint between the receptor chamber and donor chamber. The separation medium can be, for example, a 0.45 µm cellulose acetate membrane or suitable human cadaver skin.

Process 206 comprises collecting samples at different time points. Samples are typically collected at 0.5, 1, 2, 4, and 8 hours. Samples can be collected according to the following procedure. First, the receptor chamber is filled with the receptor fluid, and a membrane is placed between the donor and receptor chambers. Next, the donor chamber is loaded with the appropriate amount of progesterone cream (e.g. 0.7 g). The samples are then collected and replaced with fresh volume of sample solution (e.g. 2.0 mL) at each sampling. If the samples are not analyzed immediately, they are stored in a refrigerator until analysis is conducted.

Process 208 comprises submitting the samples to an analytical lab for high performance liquid chromatography (HPLC) analysis. Process 210 comprises calculating or measuring the transport, diffusion, or permeability. The calculated or measured transport, diffusion, or permeability can be compared to transport, diffusion, or permeability of existing commercial cream products measured or calculated according to a similar process.

IV. Methods for Treating Hormone Deficiency

In related aspects, there are provided methods for treating a condition associated with hormone deficiency in a subject. The methods include administering to the subject any of the pharmaceutical formulations described herein.

In some embodiments, the pharmaceutical compositions disclosed herein are useful in treating conditions in subjects caused, at least in part, by a hormone deficiency, particularly for women with a uterus. For example, in some embodiments, the pharmaceutical compositions disclosed herein are useful for the treatment of one or more of the following conditions: endometrial hyperplasia; endometriosis; secondary amenorrhea; preterm birth, when the subject has a shortened cervix; menopause-related symptoms including, for example, vasomotor symptoms; in relation to treatment of hypoestrogenism related symptoms including, for example and without limitation, hot flashes and night sweats (vasomotor symptoms), sleep disturbances, mood changes and vulvar and vaginal atrophy; and osteoporosis, and other non-menopausal disease states or conditions treated with supplemental progesterone or estrogen. Thus, in some embodiments, this disclosure provides methods of treating such a condition by administering to the subject a composition comprising progesterone (or progesterone and estradiol) as described herein in a dosage suitable for the treatment of the given condition.

In some embodiments, the condition is associated with progesterone deficiency in the subject. In some embodiments, the condition is associated with estradiol deficiency in the subject. In some embodiments, the condition is selected from endometrial hyperplasia, endometriosis, secondary amenorrhea, hot flashes, night sweats, sleep disturbances, mood changes, vulvo-vaginal atrophy, and osteoporosis.

In some embodiments, the progesterone compositions disclosed herein can be used to counteract effects of estradiol in subjects receiving estradiol therapy.

As disclosed herein, any suitable amount of progesterone or estradiol, or a composition containing progesterone or estradiol, can be used in the methods disclosed herein, depending on the condition being treated. When used to treat or to protect against endometrial hyperplasia associated with co-administration of estradiol, progesterone is generally administered to a subject in an amount ranging from about 0.1 mg to 200 mg per day. In some embodiments, progesterone is administered to a subject in an amount ranging from about 0.1 mg to 100 mg per day. For example, progesterone can be administered in an amount from about 0.1 to about 1 mg per day, or from about 1 to about 10 mg per day, or from about 10 to about 100 mg per day, or from about 100 to about 200 mg per day. Progesterone can be administered in an amount from about 0.1 to about 50 mg per day, or from about 0.5 to about 25 mg per day. Progesterone can be administered in an amount of about 0.1, 0.5, 1, 2, 3, 4, 5, 6, 7, 8, 9, 10, 15, 20, 25, 30, 35, 40, 45, or 50 mg per day. Other conditions, for example secondary amenorrhea, will be dosed proportionally higher as would be known to a person of ordinary skill in the art. For example, oral doses of progesterone for secondary amenorrhea are often dosed at 150%-200% more than the dosage used to prevent endometrial hyperplasia (200 mg of progesterone dosed daily for endometrial protection versus 400 mg of progesterone for secondary amenorrhea).

In general, estradiol is administered to a subject in an amount ranging from about 0.01 mg to 10 mg per day. For example, estradiol can be administered in an amount from about 0.01 to about 0.1 mg per day, or from about 0.1 to about 1 mg per day, or from about 1 to about 10 mg per day. Estradiol can be administered in an amount from about 0.01 to about 10 mg per day, or from about 0.1 to about 9 mg per day, or from about 0.25 to about 7.5 mg per day, or from about 0.5 to about 5.5 mg per day, or from about 1 to about 3 mg per day, or from about 1.5 to about 2.5 mg per day. Estradiol can be administered in an amount of about 0.01, 0.05, 0.1, 0.125, 0.15, 0.20, 0.25, 0.30, 0.35, 0.375, 0.40, 0.45, 0.50, 0.55, 0.60, 0.625, 0.65, 0.70, 0.75, 0.80, 0.85, 0.90, 0.95 1.00, 1.125, 1.25, 1.375, 1.50, 1.625, 1.75, or 2.00 mg per day.

Compositions disclosed herein can be administered as one or more doses per day. In some embodiments, a composition described herein is administered once per day in the methods disclosed herein. Compositions disclosed herein can be administered by applying the compositions to the stomach, the legs, the inner thighs, or another suitable area of the body.

The pharmaceutical compositions disclosed herein can be formulated to provide desirable pharmacokinetic parameters in a subject (e.g., a female subject) to whom the composition is administered. In some embodiments, a pharmaceutical composition as described herein produces desirable pharmacokinetic parameters for progesterone in the subject. In some embodiments, a pharmaceutical composition as described herein produces desirable pharmacokinetic parameters for estradiol in the subject. In some embodiments, a pharmaceutical composition as described herein produces desirable pharmacokinetic parameters for one or more metabolites of progesterone or estradiol in the subject, for example estrone, total estrone, allopregnanolone, or allopregnanolone sulfate.

Following the administration of a composition comprising progesterone and estradiol to a subject, the concentration and metabolism of progesterone or estradiol can be measured in a sample (e.g., a blood sample, a blood plasma sample, a capillary fluid sample, or a saliva sample) from the subject. The pharmaceutical compositions disclosed herein can be characterized for one or more pharmacokinetic parameters of progesterone, estradiol, or a metabolite thereof following administration of the composition to a subject or to a population of subjects. These pharmacokinetic parameters include AUC, $C_{max}$, and $t_{max}$. AUC is a determination of the area under the curve (AUC) plotting the sample concentration of drug along the ordinate (Y-axis) against time along the abscissa (X-axis). AUCs are well understood, frequently used tools in the pharmaceutical arts and have been extensively described. $C_{max}$ is well understood in the art as an abbreviation for the maximum drug concentration in a sample (such as a saliva sample) from a subject. $t_{max}$ is well understood in the art as an abbreviation for the time to maximum drug concentration in a sample (such as a saliva sample) of a subject.

In some embodiments, one or more pharmacokinetic parameters, e.g., AUC, $C_{max}$, or $t_{max}$, is measured for estradiol. In some embodiments, one or more pharmacokinetic parameters, e.g., AUC, $C_{max}$, or $t_{max}$, is measured for progesterone. In some embodiments, one or more pharmacokinetic parameters, e.g., AUC, $C_{max}$, or $t_{max}$, is measured for estrone. In some embodiments, one or more pharmacokinetic parameters, e.g., AUC, $C_{max}$, or $t_{max}$, is measured for total estrone. In some embodiments, one or more pharmacokinetic parameters, e.g., AUC, $C_{max}$, or $t_{max}$, is measured for allopregnanolone.

Any of a variety of methods can be used for measuring the levels of progesterone, estradiol, estrone, total estrone, allopregnanolone, or allopregnanolone sulfate in a sample, including immunoassays, mass spectrometry (MS), HPLC with ultraviolet fluorescent detection, liquid chromatography in conjunction with mass spectrometry (LC-MS), tandem mass spectrometry (MS/MS), and liquid chromatography-tandem mass spectrometry (LC-MS/MS). In some embodiments, the levels of progesterone, estradiol, estrone, or total estrone are measured using a validated LC-MS/MS method. Methods of measuring hormone levels are well described in the literature.

The levels of progesterone, estradiol, estrone, total estrone, allopregnanolone, or allopregnanolone sulfate can be measured in many biological samples, e.g., a tissue or fluid such as blood, serum, plasma, capillary fluid, saliva, or urine. In some embodiments, the levels of progesterone, estradiol, estrone, total estrone, allopregnanolone, or allopregnanolone sulfate are measured about 0.0, 0.10, 0.20, 0.05, 0.30, 0.35, 0.40, 0.45, 0.5, 1, 2, 3, 4, 5, 6, 7, 8, 9, 10, 12, 15, 18, 21, 24, 27, 30, 33, 36, 39, 42, 45, or 48 hours after dosing, or any other appropriate time period that is common or useful in determining the levels of each of the hormones. Generally, assays to determine the levels of progesterone, estradiol, estrone, total estrone, allopregnanolone, or allopregnanolone sulfate are measured one or more times every 5, 10, 15, 20, 30, 60, 120, 360, 480, 720, or 1440 minutes after administration, or combinations thereof (e.g., the first measurements are taken every 15 minutes for the first hour, followed by every 120 minutes thereafter). In some embodiments, the levels of progesterone, estradiol, estrone, total estrone, allopregnanolone, or allopregnanolone sulfate are measured about 48 hours after dosing. In embodiments, the timing of such measurements are designed to accurately measure $C_{max}$, $t_{max}$, or AUC. Timing can be adjusted based on the given circumstances (i.e., one formulation may cause a more rapid $C_{max}$, in which case the initial times would be clustered closer together, closer to time zero, or both to ensure accurate measurement of $C_{max}$, $t_{max}$, and AUC). The timing of assays may differ depending on the type of biological sample; $C_{max}$, $t_{max}$, or AUC may occur at different time points depending on the type of biological sample is assayed.

V. Examples

Example 1. Progesterone Solubility Study

Solubility of progesterone was determined on a visual basis by adding progesterone incrementally to a certain quantity of solvent at room temperature until a supersaturated solution was formed. Results of the study are summarized in Table 2.

TABLE 2

Solubility of progesterone in different solvent systems.

| *Solubility was determined by HPLC. | *Solubility was determined by HPLC. |
|---|---|
| Propylene Glycol | 10.5 |
| d-Limonene | 204.0 |
| TRANSCUTOL | 60.3 |
| MIGLYOL 812 | 25.0 |
| MIGLYOL 812 + TRANSCUTOL(90:10) | 50.5 |
| MIGLYOL 812 + TRANSCUTOL (92.5:7.5) | 40.2 |
| MIGLYOL 812 + TRANSCUTOL (95:5) | 40.5 |
| MIGLYOL 812 + d-Limonene (95:5) | 29.9 |
| d-Limonene + TRANSCUTOL (33:67) | 51.6 |
| d-Limonene + TRANSCUTOL (40:60) | 101.8 |
| d-Limonene + TRANSCUTOL (50:50) | 100.3 |
| d-Limonene + TRANSCUTOL (25:75) | 95.6 |
| MIGLYOL 840 | 41.7 |
| MIGLYOL 829 | 41.3 |
| Oleic Acid | 62.2 |
| GLYCEROX 767 | 22.2 |
| MIGLYOL 812 + Vitamin E TPGS (91:9) | 45.2 |
| MIGLYOL 812 + D-L α Tocopherol Care (95:5) | 20.1 |

TABLE 2-continued

Solubility of progesterone in different solvent systems.

| *Solubility was determined by HPLC. | *Solubility was determined by HPLC. |
|---|---|
| MIGLYOL 812 + D-L α Tocopherol Care (85:15) | 38.2 |
| 5% SLS | 6.6 |
| Oleyl Alcohol | 41.2 |
| LAUROGLYCOL 90 | 90.2 |
| LAUROGLYCOL FCC | 60 |
| LABRAFAC PG | 41 |
| MIGLYOL 812 + LAUROGLYCOL 90 (50:50) | 58.9 |
| MIGLYOL 812 + LAUROGLYCOL 90 (25:75) | 47.0 |
| MIGLYOL 812 + LABRAFAC PG (50:50) | 25.7 |
| CAPRYOL 90* | 111.5 |
| Dimethyl Isosorbide | 92 |
| CAPRYOL PGMC | 82 |
| Absolute Alcohol | 57 |

*Solubility was determined by HPLC.

Example 2. Placebo Cream Formulations

A buffered aqueous solution containing 0.1M citric acid and 0.2M $Na_2HPO_4$ having a target pH of 5.4-5.6 was prepared and heated to 70° C. If carbomer was included in a composition, the carbomer was added to the aqueous solution and mixed until completely dissolved and a uniform solution was obtained. Oil components (e.g., MIGLYOL 812, CREMOPHOR A6, CREMOPHOR A25, cetyl alcohol, additional emulsifiers) were weighed and heated to 70° C. When the oil and aqueous phases attained the desired temperature, they were removed from the heat and the oil phase was slowly added to the aqueous phase while stirring at 600-1200 RPM using a Caframo BDC 2002 lab mixer. Stirring was continued until the temperature of the mixture was 40° C. or lower. When the desired temperature was reached, solvents and other components (e.g., propylene glycol, TRANSCUTOL, d-limonene, and additional excipients) were added to the cream and mixing was continued until the temperature of the cream was 25° C. or lower. The cream was homogenized using an IKA homogenizer for 2-5 minutes. Placebo compositions were prepared as set forth in Tables 3-5.

TABLE 3

Placebo Cream Compositions

| Ingredient | Placebo Cream 2-1 % | Placebo Cream 2-2 % |
|---|---|---|
| MIGLYOL ® 812 | 30.0 | 30.0 |
| d-Limonene | 1.5 | 1.5 |
| TRANSCUTOL ® | 3.0 | 3.0 |
| CREMOPHOR A6 | 3.0 | 3.0 |
| CREMOPHOR A25 | 3.0 | 3.0 |
| Cetyl Alcohol | 4.5 | 5.5 |
| Propylene Glycol | 5.0 | 3.0 |
| Carbomer | — | 0.5 |
| Water* | 50.0 | 50.5 |

*Water = 0.1M Citric Acid & 0.2M $Na_2HPO_4$ solutions to provide a target pH of 5.4-5.6

TABLE 4

Placebo Cream Compositions

| Ingredient | 2-3 % (w/w) | 2-4 % (w/w) | 2-5 % (w/w) | 2-6 % (w/w) | 2-7 % (w/w) | 2-8 % (w/w) |
|---|---|---|---|---|---|---|
| MIGLYOL 812 | 30.0 | 30.0 | 15.0 | 15.0 | 15.0 | 15.0 |
| d-Limonene | 1.5 | 1.5 | 5.0 | 5.0 | 5.0 | 5.0 |
| TRANSCUTOL | 3.0 | 3.0 | 3.0 | 3.0 | 3.0 | 3.0 |
| CREMOPHOR A6 | 3.0 | 3.0 | 3.0 | — | — | — |
| CREMOPHOR A25 | 3.0 | 3.0 | 3.0 | — | — | — |
| Cetyl Alcohol | 4.5 | 5.5 | 6.2 | — | — | — |
| GELOT 64 | — | — | — | 12.0 | 12.0 | 12.0 |
| EMULCIRE 61 | — | — | — | 3.0 | 5.0 | 5.0 |
| Propylene Glycol | 5.0 | 3.0 | — | 4.0 | 4.0 | 4.0 |
| LAUROGLYCOL | — | — | 5.0 | 5.0 | 5.0 | 5.0 |
| Carbomer | — | 0.5 | 0.02 | — | 0.1 | 0.01 |
| Iso Stearyl Alcohol | — | — | 3.0 | — | — | — |
| Ethyl Vanillin | — | — | 0.05 | — | — | — |
| Methyl Paraben | — | — | — | 0.2 | 0.2 | 0.2 |
| Propyl Paraben | — | — | — | 0.02 | 0.02 | 0.02 |
| Water* | 50.0 | 50.5 | 56.73 | 52.78 | 50.68 | 50.77 |

*Water = 0.1M Citric Acid & 0.2M $Na_2HPO_4$ solutions to provide a target pH of 5.4-5.6

TABLE 5

Placebo Cream Compositions

| Ingredient | 2-9 % (w/w) | 2-10 % (w/w) | 2-11 % (w/w) | 2-12 % (w/w) | 2-13 % (w/w) | 2-14 % (w/w) |
|---|---|---|---|---|---|---|
| MIGLYOL 812 | 15.0 | 15.0 | 15.0 | 15.0 | 15.0 | 15.0 |
| d-Limonene | 5.0 | 5.0 | 5.0 | 5.0 | 5.0 | 5.0 |
| TRANSCUTOL | 3.0 | 3.0 | 3.0 | 3.0 | 3.0 | 3.0 |
| CITHROL DPHS | — | 2.0 | 2.0 | — | — | — |

TABLE 5-continued

| | Placebo Cream Compositions | | | | | |
|---|---|---|---|---|---|---|
| Ingredient | 2-9 % (w/w) | 2-10 % (w/w) | 2-11 % (w/w) | 2-12 % (w/w) | 2-13 % (w/w) | 2-14 % (w/w) |
| Glyceryl Stearate | — | — | — | — | 5.0 | 5.0 |
| PEG 100 Stearate | — | 5.0 | 6.0 | — | 5.0 | 5.0 |
| Cetyl Alcohol | 9.0 | 7.0 | 8.0 | — | 6.0 | 3.0 |
| KOLLIPHOR RH40 | — | — | — | 2.0 | — | — |
| GELOT 64 | — | — | — | 8.0 | — | — |
| EMULCIRE 61 | — | — | — | 4.0 | — | — |
| Polysorbate 80 | 8.0 | — | — | — | — | — |
| Lecithin | 2.0 | — | — | — | — | — |
| Propylene Glycol | 4.0 | 4.0 | 4.0 | 4.0 | 4.0 | 4.0 |
| LAUROGLYCOL | 5.0 | 5.0 | 5.0 | 5.0 | 5.0 | 5.0 |
| Carbomer | 0.1 | NA | 0.1 | 0.1 | 0.02 | 0.1 |
| Methyl Paraben | 0.2 | 0.2 | 0.2 | 0.2 | 0.2 | 0.2 |
| Propyl Paraben | 0.02 | 0.02 | 0.02 | 0.02 | 0.02 | 0.02 |
| Water* | 48.68 | 53.78 | 51.68 | 53.68 | 51.76 | 54.68 |

Water* = 0.1M Citric Acid & 0.2M Na$_2$HPO$_4$ solutions to provide a target pH of 5.4-5.6

Example 3. Progesterone Cream Compositions

Progesterone cream compositions were formulated as described in Example 2, with micronized progesterone included in the oily phase. Creams were formulated with the components set forth in Table 6.

TABLE 6

| | Progesterone Cream Compositions. | | | |
|---|---|---|---|---|
| Ingredient | 3-1 % (w/w) | 3-2 % (w/w) | 3-3 % (w/w) | 3-4 % (w/w) |
| Progesterone | 2.0 | 3.0 | 3.0 | 2 |
| MIGLYOL 840 | 25.0 | — | — | — |
| MIGLYOL 812 | — | 25.0 | 15.0 | 25 |
| d-Limonene | 1.5 | 1.5 | 2.0 | 1.5 |
| TRANSCUTOL | 3.5 | 3.0 | 3.0 | 3 |
| Oleic Acid | 3.0 | — | — | — |
| CREMOPHOR A6 | 3.0 | 3.0 | 3.0 | 3 |
| CREMOPHOR A25 | 3.0 | 3.0 | 3.0 | 3 |
| Cetyl Alcohol | 5.5 | 6.8 | 6.5 | 6.2 |
| Propylene Glycol | 3.3 | 3.0 | 4.0 | 3 |
| Carbomer | 0.2 | 0.2 | 0.1 | 0.1 |
| Isostearyl Alcohol | — | — | 3.0 | 3 |
| Ethyl Vanillin | — | 0.1 | 0.1 | 0.1 |
| Water* | 50.0 | 51.4 | 57.3 | 50.1 |

Water* = 0.1M Citric Acid & 0.2M Na$_2$HPO$_4$ solutions to provide a target pH of 5.4-5.6

Composition 3-1 exhibited an undesirable feel upon application to skin. Particle formation, including progesterone particle formation, was observed for compositions 3-1, 3-2, and 3-3. Composition 3-4 was obtained as a uniform cream, with no visible progesterone particles observed.

Additional progesterone creams were formulated with the components set forth in Table 7.

TABLE 7

| | Progesterone Cream Compositions | | | | | |
|---|---|---|---|---|---|---|
| Ingredient | 3-5 % (w/w) | 3-6 % (w/w) | 3-7 % (w/w) | 3-8 % (w/w) | 3-9 % (w/w) | 3-10 % (w/w) |
| Progesterone | 2.5 | 3.0 | 2.5 | 2.5 | 2.5 | 2.5 |
| MIGLYOL 812 | 15.0 | 15.0 | 15.0 | 15.0 | 15.0 | 15.0 |
| d-Limonene | 5.0 | 10.0 | 7.5 | 5.0 | 5.0 | 5.0 |
| TRANSCUTOL | 3.0 | 3.0 | 3.0 | 3.0 | 3.0 | 3.0 |
| CREMOPHOR A6 | 3.0 | 3.0 | 3.0 | 3.0 | — | — |
| CREMOPHOR A25 | 3.0 | 3.0 | 3.0 | 3.0 | — | — |
| GELOT 64 | — | — | — | — | 4.0 | 4.0 |
| EMULCIRE 61 | — | — | — | — | 4.0 | 4.0 |
| CAPRYOL 90 | — | — | — | 5.0 | — | — |
| Cetyl Alcohol | 6.2 | 6.2 | 6.2 | 6.2 | 4.2 | 3.2 |
| LAUROGLYCOL | 5.0 | 5.0 | 5.0 | — | 5.0 | 5.0 |
| Carbomer | 0.02 | 0.02 | 0.02 | 0.02 | 0.02 | — |
| Iso Stearyl Alcohol | 3.0 | 3.0 | 3.0 | 3.0 | 3.0 | 3.0 |
| Ethyl Vanillin | 0.05 | — | — | — | — | — |
| Methyl Paraben | — | 0.1 | 0.1 | 0.2 | 0.2 | 0.2 |
| Propyl Paraben | — | 0.01 | 0.01 | 0.02 | 0.02 | 0.02 |
| Water* | 54.23 | 48.67 | 51.67 | 54.06 | 54.06 | 55.08 |

Water* = 0.1M Citric Acid & 0.2M Na$_2$HPO$_4$ solutions to provide a target pH of 5.4-5.6

Compositions 3-5, 3-6, 3-7, and 3-8 were obtained as uniform white creams. Compositions 3-5, 3-6, and 3-8 exhibited some instability, separating after storage for 24 hours at 40° C. Composition 3-7 exhibited instability after storage for 2 days at 45° C. Viscous creams were obtained for compositions 3-9 and 3-10; carbomer concentrations were reduced for subsequent formulations.

Additional progesterone creams were formulated with the components set forth in Table 8.

Composition 3-11 exhibited desirable viscosity; progesterone granules were observed upon addition of progesterone. Composition 3-12, 3-13, 3-14, and 3-15 exhibited instability. Physical instability was observed for composition 3-12 after storage for 13 days, and physical instability was observed for composition 3-14 after storage at 45° C. for 2 days. Formulation of composition 3-13 did not result in a stable emulsion. Formulation 3-16 was obtained as a uniform white cream.

TABLE 8

Progesterone Cream Compositions.

| Ingredient | 3-11 % (w/w) | 3-12 % (w/w) | 3-13 % (w/w) | 3-14 % (w/w) | 3-15 % (w/w) | 3-16 % (w/w) |
| --- | --- | --- | --- | --- | --- | --- |
| Progesterone | 2.5 | 2.5 | 2.5 | 2.5 | 2.5 | 2.5 |
| MIGLYOL 812 | 15.0 | 15.0 | 15.0 | 15.0 | 15.0 | 15.0 |
| d-Limonene | 5.0 | 5.0 | 5.0 | 5.0 | 5.0 | 5.0 |
| TRANSCUTOL | 3.0 | 3.0 | 3.0 | 3.0 | 3.0 | 3.0 |
| CREMOPHOR A6 | — | — | — | — | — | 3.0 |
| CREMOPHOR A25 | — | — | — | — | — | 3.0 |
| GELOT 64 | 4.0 | 4.0 | — | 8.0 | 12.0 | — |
| EMULCIRE 61 | 4.0 | 4.0 | 3.0 | 3.0 | 5.0 | — |
| APIFIL | — | — | 5.0 | — | — | — |
| CAPRYOL 90 | — | — | — | — | — | — |
| Cetyl Alcohol | — | — | — | — | — | 6.2 |
| LAUROGLYCOL | 5.0 | 5.0 | 5.0 | 5.0 | 5.0 | — |
| Carbomer | — | — | — | — | — | 0.02 |
| Isostearyl Alcohol | 3.0 | 3.0 | 3.0 | — | — | 3.0 |
| Propylene Glycol | 3.0 | 3.0 | 3.0 | 5.0 | 4.0 | 3.0 |
| Ethyl Vanillin | — | — | — | — | — | 0.05 |
| Methyl Paraben | 0.2 | 0.2 | 0.2 | 0.2 | 0.2 | — |
| Propyl Paraben | 0.02 | 0.02 | 0.02 | 0.02 | 0.02 | — |
| Water* | 55.28 | 55.28 | 55.28 | 53.28 | 48.28 | 56.23 |

Water* = 0.1M Citric Acid & 0.2M Na$_2$HPO$_4$ solutions to provide a target pH of 5.4-5.6

Additional progesterone creams were formulated with the components set forth in Table 9.

Thin, less viscous creams were obtained for compositions 3-17 and 3-18. Thick, viscous uniform creams were obtained for compositions 3-19 and 3-20. Composition 3-19 began to separate after storage at 40° C. for 16 hours, while Composition 3-20 began to separate after storage at 40° C. for 18 hours. Formulations 3-21, 3-22, and 3-23 were obtained as uniform off-white to light yellow creams, which were stable upon storage at 40° C.

TABLE 9

Progesterone Cream Compositions.

| Ingredient | 3-17 % (w/w) | 3-18 % (w/w) | 3-19 % (w/w) | 3-20 % (w/w) | 3-21 % (w/w) | 3-22 % (w/w) | 3-23 % (w/w) |
| --- | --- | --- | --- | --- | --- | --- | --- |
| Progesterone | 2.5 | 2.5 | 2.5 | 2.5 | 2.5 | 2.5 | 2.5 |
| MIGLYOL 812 | 15.0 | 15.0 | 15.0 | 15.0 | 15.0 | 15.0 | 15.0 |
| d-Limonene | — | 5.0 | 5.0 | 5.0 | 5.0 | 5.0 | — |
| TRANSCUTOL | 3.0 | — | 3.0 | 3.0 | 3.0 | 3.0 | 3.0 |
| CREMOPHOR A6 | 3.0 | 3.0 | — | 3.0 | — | — | — |
| CREMOPHOR A25 | 3.0 | 3.0 | — | 3.0 | — | — | — |
| GELOT 64 | — | — | — | — | 7.0 | 7.0 | 7.0 |
| EMULCIRE 61 | — | — | — | — | 3.5 | 3.5 | 3.5 |
| Glyceryl Stearate | — | — | 5.0 | — | — | — | — |
| PEG 100 Stearate | — | — | 5.0 | — | — | — | — |
| Lecithin | — | — | — | 3.0 | 3.0 | 3.0 | 3.0 |
| Cetyl Alcohol | 6.2 | 6.2 | 6.0 | 6.2 | — | — | — |
| LAUROGLYCOL | 5.0 | 5.0 | 5.0 | 5.0 | 5.0 | 5.0 | 5.0 |
| Carbomer | 0.02 | 0.02 | 0.02 | 0.02 | 0.1 | 0.2 | 0.2 |
| Isostearyl Alcohol | 3.0 | 3.0 | — | 3.0 | — | — | — |
| Propylene Glycol | 3.0 | 3.0 | 4.0 | — | 4.0 | 4.0 | 4.0 |
| Ethyl Vanillin | 0.05 | 0.05 | — | 0.05 | — | — | — |
| Methyl Paraben | — | — | 0.2 | — | 0.2 | 0.2 | 0.2 |

TABLE 9-continued

Progesterone Cream Compositions.

| Ingredient | 3-17 % (w/w) | 3-18 % (w/w) | 3-19 % (w/w) | 3-20 % (w/w) | 3-21 % (w/w) | 3-22 % (w/w) | 3-23 % (w/w) |
|---|---|---|---|---|---|---|---|
| Propyl Paraben | — | — | 0.02 | — | 0.02 | 0.02 | 0.02 |
| Water* | 56.23 | 54.23 | 49.26 | 51.3 | 51.68 | 51.58 | 56.58 |

Water* = 0.1M Citric Acid & 0.2M Na$_2$HPO$_4$ solutions to provide a target pH of 5.4-5.6

Additional progesterone creams were formulated with the components set forth in Table 10.

Compositions 3-24 and 3-25 were obtained as uniform creams. The viscosity of composition 3-25 was very low; higher concentrations of carbomer were used to obtain desirable viscosity. Application of composition 3-26 resulted in an undesirable feeling on the skin, and crystals were observed in the composition after storage for one month at room temperature. Compositions 3-28 and 3-29 did not exhibit a glossy appearance and contained visible particles of progesterone. Composition 3-30 exhibited a glossy appearance and contained visible particles of progesterone.

TABLE 10

Progesterone Cream Compositions.

| Ingredient | 3-24 % (w/w) | 3-25 % (w/w) | 3-26 % (w/w) | 3-27 % (w/w) | 3-28 % (w/w) | 3-29 % (w/w) | 3-30 % (w/w) |
|---|---|---|---|---|---|---|---|
| Progesterone | 2.0 | 2.5 | 2.0 | 2.0 | 5.0 | 3.0 | 3.0 |
| MIGLYOL 840 | — | — | — | 25.0 | — | — | — |
| MIGLYOL 812 | 25.0 | 15.0 | 15.0 | — | 28.0 | 25.0 | 15.0 |
| d-Limonene | 1.5 | 5.0 | 5.0 | 1.5 | 2.0 | 1.5 | 2.0 |
| TRANSCUTOL | 3.0 | 3.0 | 3.0 | 3.5 | 2.0 | 3.0 | 3.0 |
| CREMOPHOR A6 | 3.0 | 3.0 | 1.5 | 3.0 | 2.0 | 3.0 | 3.0 |
| CREMOPHOR A25 | 3.0 | 3.0 | 4.5 | 3.0 | 2.0 | 3.0 | 3.0 |
| Cetyl Alcohol | 6.2 | 6.2 | 6.2 | 5.5 | 5.5 | 6.8 | 6.5 |
| LAUROGLYCOL 90 | — | 5.0 | 5.0 | — | 3.0 | 3.0 | 4.0 |
| Propylene Glycol | 3.0 | — | 4.0 | 3.3 | 0.3 | 0.2 | 0.1 |
| Carbomer | 0.1 | 0.02 | 0.01 | 0.2 | 50.15 | 51 | 57.3 |
| Water | 50.1 | 54.23* | 50.2* | 50.0 | 3.0 | 3.0 | 4.0 |
| Oleic acid | — | — | — | 3.0 | — | — | — |
| Ethyl Vanilla | 0.1 | 0.05 | 0.05 | 0.05 | 0.1 | 0.1 | 0.05 |
| Isostearyl alcohol | 3.0 | 3.0 | 3.0 | — | — | 3.0 | — |

Water* = 0.1M Citric Acid & 0.2M Na$_2$HPO$_4$ solutions to provide a target pH of 5.4-5.6

Example 4. Franz Diffusion Cell Studies

Penetration of progesterone using creams with different penetration enhancer concentrations was studied. Measured flux values for the compositions are summarized in Table 11.

TABLE 11

Summary of flux of cream formulations with different concentrations of penetration enhancers.

| Composition | Flux ($\mu g \cdot cm^{-2} \cdot hr^{-1}$) |
|---|---|
| 3-17 | 44.462 |
| 3-18 | 64.929 |
| 3-16 | 77.645 |
| 3-5 | 83.747 |

Figure 3:
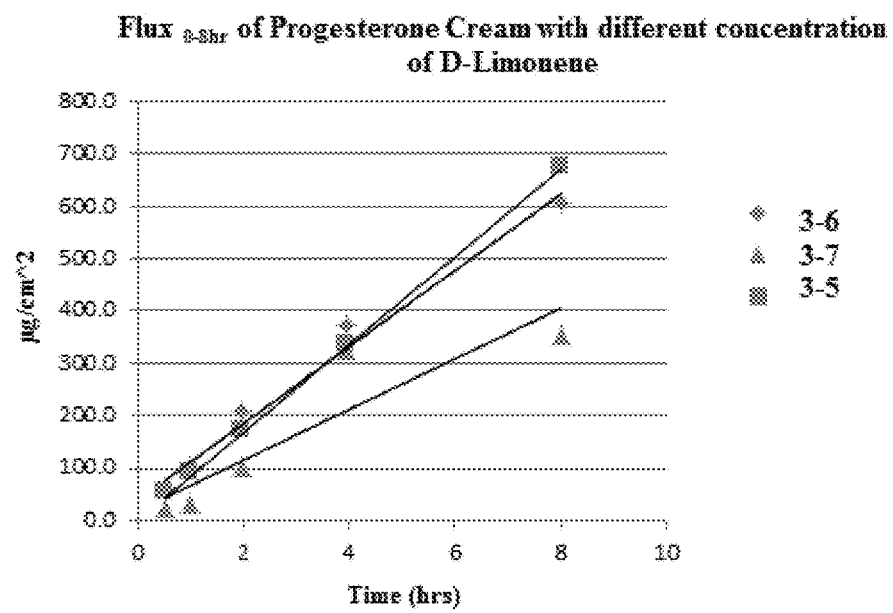
FIG. 3 shows Franz diffusion cell flux data for progesterone compositions having different concentrations of d-limonene.

Flux of progesterone creams with different concentration of d-limonene was studied. Experimental data is shown in FIG. 3, and the measured flux values are summarized in Table 12.

TABLE 12

Summary of flux of cream formulations with different concentrations of d-limonene

| Composition | Flux ($\mu g \cdot cm^{-2} \cdot hr^{-1}$) | % d-Limonene (w/w) |
|---|---|---|
| 3-6 | 33.938 | 10 |
| 3-7 | 48.224 | 7.5 |
| 3-5 | 83.745 | 5 |

Figure 4:
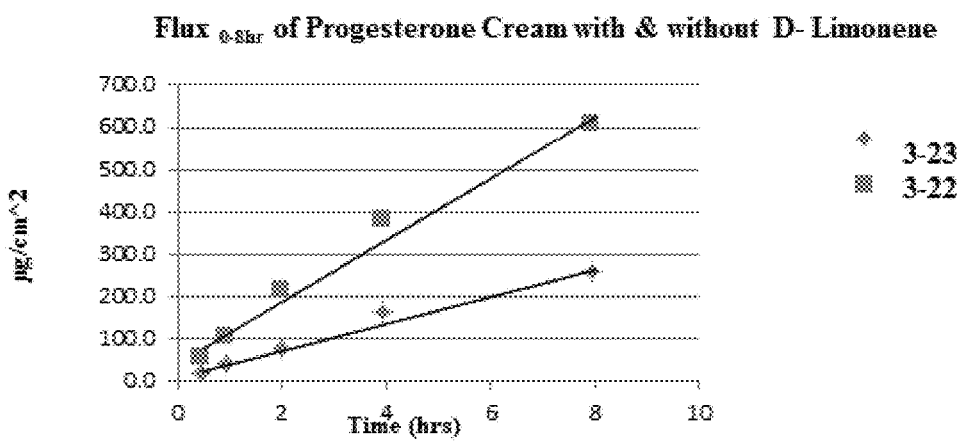
FIG. 4 shows Franz diffusion cell flux data for progesterone compositions with and without d-limonene.

Penetration of progesterone was studied using cream formulations with and without d-limonene. Data for the experiment are shown in FIG. 4 and summarized in Table 13A. The use of d-limonene resulted in a more than 100% increase in progesterone flux compared to the composition without d-limonene.

TABLE 13A

Comparison of flux of cream formulations with & without d-limonene at 0.2% Carbomer

| Composition | % d-Limonene (w/w) | Flux ($\mu g \cdot cm-2 \cdot hr-1$) |
|---|---|---|
| 3-23 | 0 | 32.065 |
| 3-22 | 5 | 72.762 |

Flux properties for the new compositions as assessed by Franz cell diffusion studies were compared with a compounded cream containing 1.6% (w/w) progesterone. The results of the comparison are summarized in Table 13B, showing that compositions of the invention exhibited marked increases in flux with respect to the comparative example.

TABLE 13B

Franz Diffusion Testing of Progesterone Cream Formulations

| Composition | Flux (µg · cm-2 · hr-1) |
|---|---|
| Comparative Example | 68.493 |
| 3-5 | 83.745 |
| 3-14 | 85.015 |

Example 5. Progesterone 2.5%/Estradiol 0.005% Cream Formulation

A composition containing progesterone and estradiol was formulated according to Table 14. An off white to light yellow cream was obtained. No visible particles of estradiol were observed. A grit-free smooth cream was formed.

TABLE 14

Progesterone 2.5%/Estradiol 0.005%
Cream Formulation and Observations

| Ingredient | Composition 5-1 % |
|---|---|
| Progesterone | 2.5 |
| Estradiol | 0.005 |
| MIGLYOL 812 | 15.0 |
| d-Limonene | 5.0 |
| TRANSCUTOL | 3.0 |
| GELOT | 7.5 |
| EMULCIRE | 3.5 |
| Lecithin | 3.0 |
| LAUROGLYCOL 90 | 5.0 |
| Propylene Glycol | 4.0 |
| Methyl Paraben | 0.2 |
| Propyl Paraben | 0.02 |
| Carbomer | 0.2 |
| Water* | 51.075 |

Water* = 0.1M Citric Acid & 0.2M Na$_2$HPO$_4$ solutions to provide a target pH of 5.4-5.6

The progesterone/estradiol cream was studied during storage under three sets of different conditions: (1) 25° C.; (2) 40° C./75% RH; (3) 2-8° C. Results of the stability study are summarized in Table 15.

TABLE 15

Stability Testing of Progesterone 2.5% Estradiol 0.005% Cream 5-1
Progesterone 2.5% (w/w)
Estradiol 0.005% (w/w)

| Stability Testing | Observation | P mg/g | % LC | E mg/g | % LC | Gritty* | Microscopy |
|---|---|---|---|---|---|---|---|
| Initial | Stable/No Separation | 23.7 | 94.8 | 0.044 | 88.0 | Absent | No crystals |
| 7 Days 25° C. | Stable/No Separation | 24.0 | 96.0 | 0.046 | 92.0 | Absent | No crystals |
| 7 Days 40° C./75% RH | Stable/No Separation | 24.2 | 96.8 | 0.045 | 90.0 | Absent | No crystals |
| 7 Days 2-8° C. | Stable/No Separation | 24.0 | 96.0 | 0.045 | 90.0 | Absent | No crystals |

P= Progesterone & E= Estradiol
*Analysis was conducted after 14 days and 30 days. No grittiness or crystals found after 30 days.

Example 6. Scale Up of Progesterone 2.5% & Progesterone 2.5%/Estradiol 0.005% Cream Larger batches of progesterone creams and progesterone/estradiol creams were formulated according to Tables 16-19.

TABLE 16

Composition I. Progesterone 2.5% Cream Formulation

| Ingredients | % w/w | Qty./Batch |
|---|---|---|
| Progesterone Micronized, USP | 2.5 | 25.0 g |
| Medium Chain Triglycerides, NF (MIGLYOL 812) | 15.0 | 150.0 g |
| D-Limonene | 5.0 | 50.0 g |
| Diethylene Glycol Mono Ethyl Ether EP/NF, (TRANSCUTOL P) | 3.0 | 30.0 g |
| Propylene Glycol Monolaurate (Type II) EP/NF, (LAUROGLYCOL 90) | 5.0 | 50.0 g |
| Mixture of Glycerol monostearate EP/NF and PEG-75 stearate NF/JPE, (GELOT 64) | 7.0 | 70.0 g |
| Mixture of Cetyl Alcohol EP/NF and Ethoxylated Fatty Alcohols (Ceteth-20, Steareth-20) EP/NF, (EMULCIRE 61 WL 2659) | 3.5 | 35.0 g |
| CARBOPOL 980 NF Polymer | 0.2 | 2.0 g |
| Liquid Soy Lecithin | 3.0 | 30.0 g |
| Propylene Glycol, USP | 4.0 | 40.0 g |
| Methyl Paraben, NF | 0.2 | 2.0 g |
| Propyl Paraben, NF, EP, BP, JP | 0.02 | 0.2 g |
| Citric Acid Monohydrate, Granular, USP | 0.47 | 4.70 g |
| Dibasic Sodium Phosphate, Dried, USP | 0.82 | 8.20 g |
| Purified Water, USP | QS | 502.90 |
| TOTAL | 100 | 1000.0 g |

TABLE 17

Composition II. Progesterone 2.5% Cream Formulation

| Ingredients | % w/w | Qty./Batch |
|---|---|---|
| Progesterone Micronized, USP | 2.5 | 25.0 g |
| Medium Chain Triglycerides, NF (MIGLYOL 812) | 15.0 | 150.0 g |
| Diethylene Glycol Mono Ethyl Ether EP/NF, (TRANSCUTOL P) | 3.0 | 30.0 g |
| Propylene Glycol Monolaurate (Type II) EP/NF, (LAUROGLYCOL 90) | 5.0 | 50.0 g |

TABLE 17-continued

Composition II. Progesterone 2.5% Cream Formulation

| Ingredients | % w/w | Qty./Batch |
|---|---|---|
| Mixture of Glycerol monostearate EP/NF and PEG-75 stearate NF/JPE, (GELOT 64) | 7.0 | 70.0 g |
| Mixture of Cetyl Alcohol EP/NF and Ethoxylated Fatty Alcohols (Ceteth-20, Steareth-20) EP/NF, (EMULCIRE 61 WL 2659) | 3.5 | 35.0 g |
| CARBOPOL 980 NF Polymer | 0.2 | 2.0 g |
| Liquid Soy Lecithin | 3.0 | 30.0 g |
| Propylene Glycol, USP | 4.0 | 40.0 g |
| Methyl Paraben, NF | 0.2 | 2.0 g |
| Propyl Paraben, NF, EP, BP, JP | 0.02 | 0.2 g |
| Citric Acid Monohydrate, Granular, USP | 0.53 | 5.30 g |
| Dibasic Sodium Phosphate, Dried, USP | 0.92 | 9.20 g |
| Purified Water, USP | QS | 551.30 |
| TOTAL | 100 | 1000.0 g |

TABLE 18

Composition III. Progesterone 2.5%/Estradiol 0.005% Cream Formulation

| Ingredients | % w/w | Qty./Batch |
|---|---|---|
| Progesterone 2.5% Cream (Composition I) | 99.595 | 497.975 g |
| Micronized Estradiol Hemihydrate, USP | 0.005 | 0.025 g |
| TRANSCUTOL P [1] | 0.4 | 2.0 g |
| TOTAL | 100 | 500.00 g |

[1] TRANSCUTOL P is used to solubilize Estradiol Hemihydrate.

TABLE 19

Composition IV. Progesterone 2.5%/Estradiol 0.005% Cream Formulation

| Ingredients | % w/w | Qty./Batch |
|---|---|---|
| Progesterone 2.5% Cream (Composition II) | 99.595 | 497.975 g |
| Micronized Estradiol Hemihydrate, USP | 0.005 | 0.025 g |
| TRANSCUTOL P [1] | 0.4 | 2.0 g |
| TOTAL | 100 | 500.00 g |

[1] TRANSCUTOL P is used to solubilize Estradiol Hemihydrate.

Stability testing was performed on cream formulations stored for four weeks at 25° C. and at 40° C./75%. Samples were tested after 2 weeks and 4 weeks to determine the amount of progesterone in the cream and to observe any separation that may have occurred. Results are shown in Table 20.

TABLE 20

Stability testing of progesterone compositions

| Stability Testing | 3-22 2.5% (w/w) Progesterone | | | 3-23 2.5% (w/w) Progesterone | | |
|---|---|---|---|---|---|---|
| | Observation | mg/g | % LC | Observation | mg/g | % LC |
| Initial | Stable/No Separation | 26.3 | 105.2 | Stable/No Separation | 25.4 | 101.6 |
| 15 Days 25° C. | Stable/No Separation | 27.6 | 110.4 | Stable/No Separation | 26.1 | 104.4 |
| 15 Days 40° C./75% RH | Stable/No Separation | 27.5 | 110.0 | Stable/No Separation | 25.4 | 101.6 |
| 30 Days 25° C. | Stable/No Separation | 28.4 | 113.6 | Stable/No Separation | 24.3 | 97.2 |
| 30 Days 40° C./75% RH | Stable/No Separation | 27.0 | 108.0 | Stable/No Separation | 23.8 | 95.2 |

Example 7. Microscopic Characterization of Progesterone Compositions

Figure 7A:
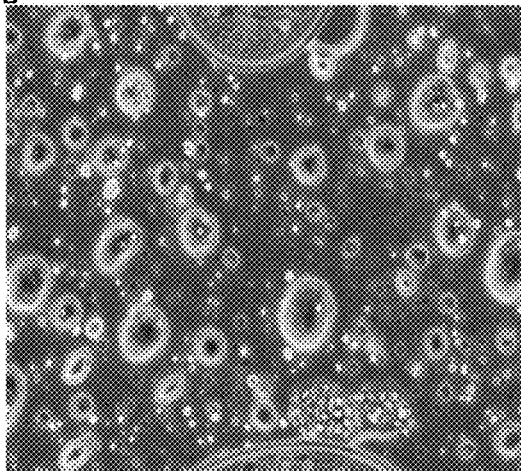
FIG. 7A shows a compounded cream viewed with a birefringence microscope using non-polarized light (10×40).
Figure 7B:
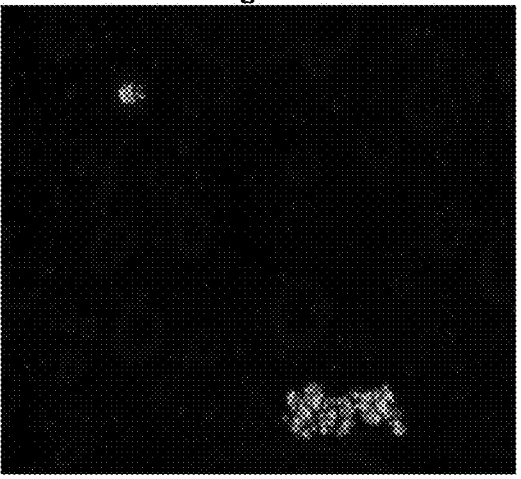
FIG. 7B shows a compounded cream viewed with a birefringence microscope using polarized light (10×40).
Figure 7C:
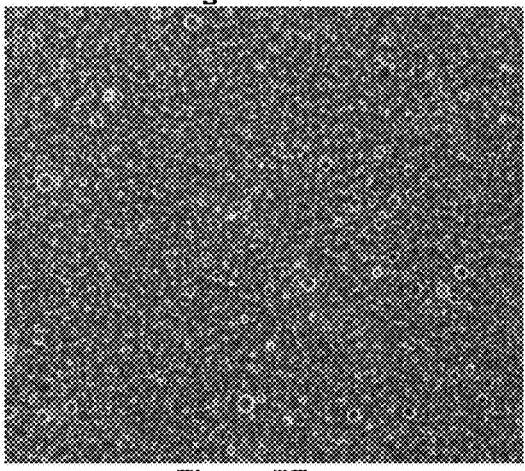
FIG. 7C shows Composition I as described herein viewed with a birefringence microscope using non-polarized light (10×40).
Figure 7D:
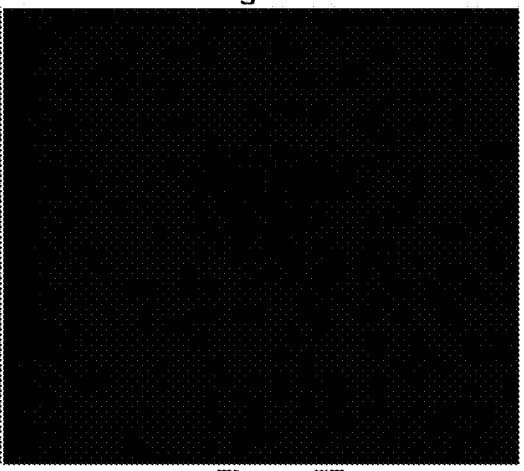
FIG. 7D shows Composition I as described herein viewed with a birefringence microscope using polarized light (10×40).
Figure 7E:
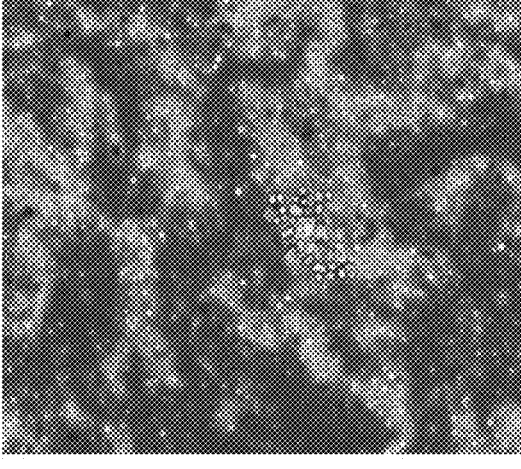
FIG. 7E shows Composition II as described herein viewed with a birefringence microscope using non-polarized light (10×40).
Figure 7F:
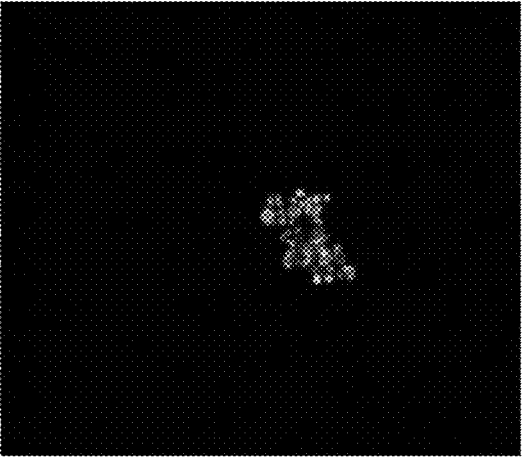
FIG. 7F shows Composition II as described herein viewed with a birefringence microscope using polarized light (10×40).

Cream formulations as described above were examined using a birefringence microscope to determine the presence or absence of progesterone crystals. Formulations as described above were also compared to a compounded progesterone cream. Crystals were observed in the compounded progesterone cream (FIG. 7A and FIG. 7B), as well as in Composition II (Progesterone Cream 2.5% without d-limonene; Table 17; FIG. 7E and FIG. 7F). More crystals were observed in the compounded progesterone cream compared to Composition II. No crystals were observed in Composition I (Progesterone Cream 2.5% with d-limonene; Table 16; FIG. 7C and FIG. 7D). Formulations with fully solubilized progesterone (i.e., without progesterone crystals) are desirable because hormone bioavailability may increase as a function of hormone solubility.

Crystals from Composition II were isolated and examined using infrared (IR) microspectroscopy. The IR data confirmed that the birefringent crystals in FIGS. 7E and 7F consisted of progesterone. There were no other chemical components in the crystals observed by IR spectroscopy.

Example 8. Measurement of Hormone Levels in Human Subjects after Application of Transdermal Progesterone/Estradiol Compositions Seven male subjects were administered 1 gram of a composition having the formulation set forth in Table 18. Subjects received 25 mg of progesterone and 50 µg of estradiol. Hormone levels were tested in blood serum, saliva, and fingertip capillary fluid at 1, 2, and 8 hours after administration. Testing was conducted using known methods. The change in hormone levels over each subject's baseline level, measured prior to cream administration, was determined for each time point.

Figure 5A:
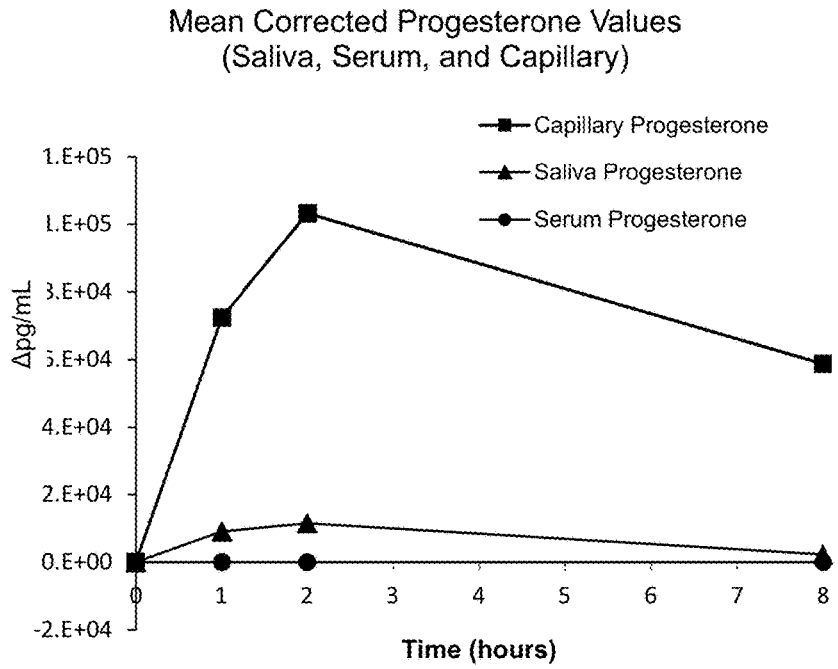
FIG. 5A shows the change in progesterone levels following administration of an exemplary progesterone/estradiol cream in human subjects. Changes over baseline progesterone levels as determined from fingertip capillary fluid, saliva, and serum samples are shown.
Figure 5B:
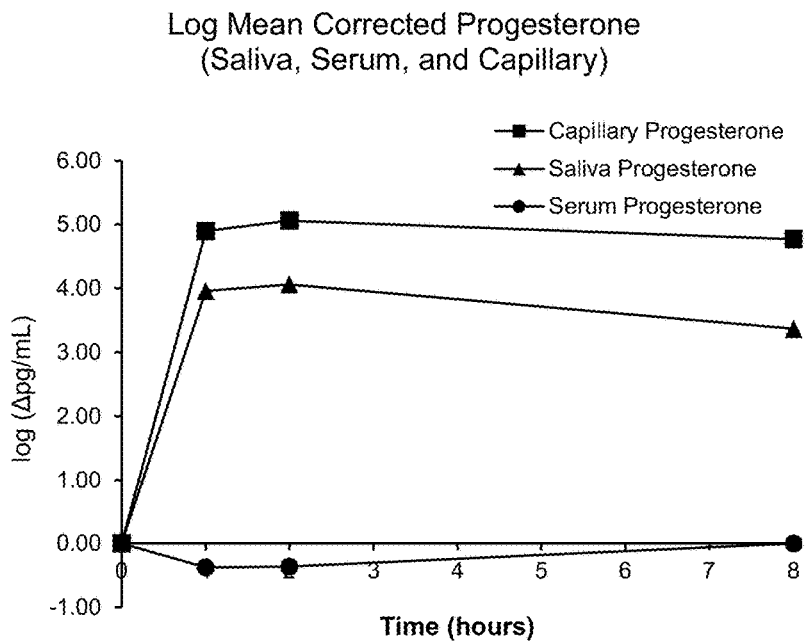
FIG. 5B shows the data plotted on a log scale.
Figure 6A:
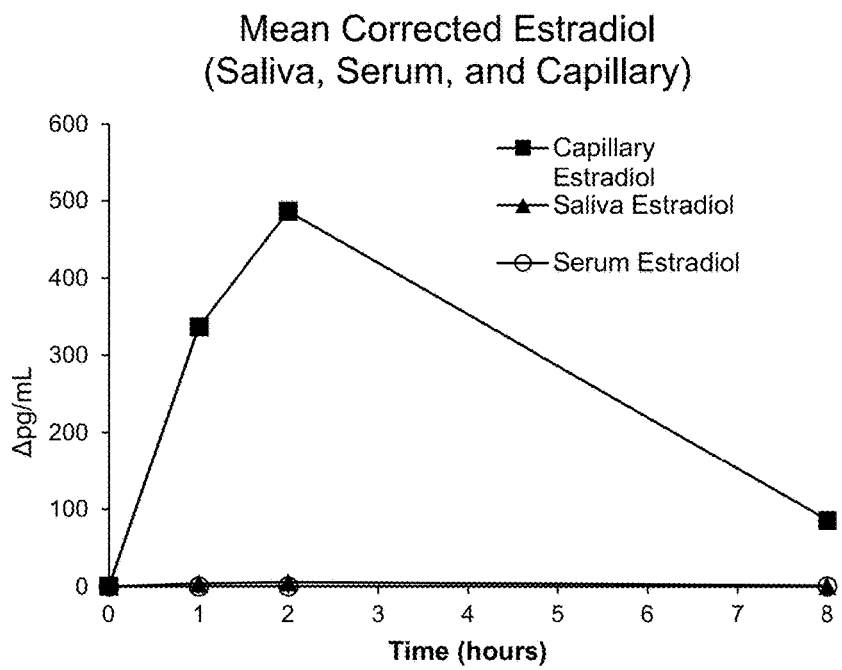
FIG. 6A shows the change in estradiol levels following administration of an exemplary progesterone/estradiol cream in human subjects. Changes over baseline estradiol levels as determined from fingertip capillary fluid, saliva, and serum samples are shown.
Figure 6B:
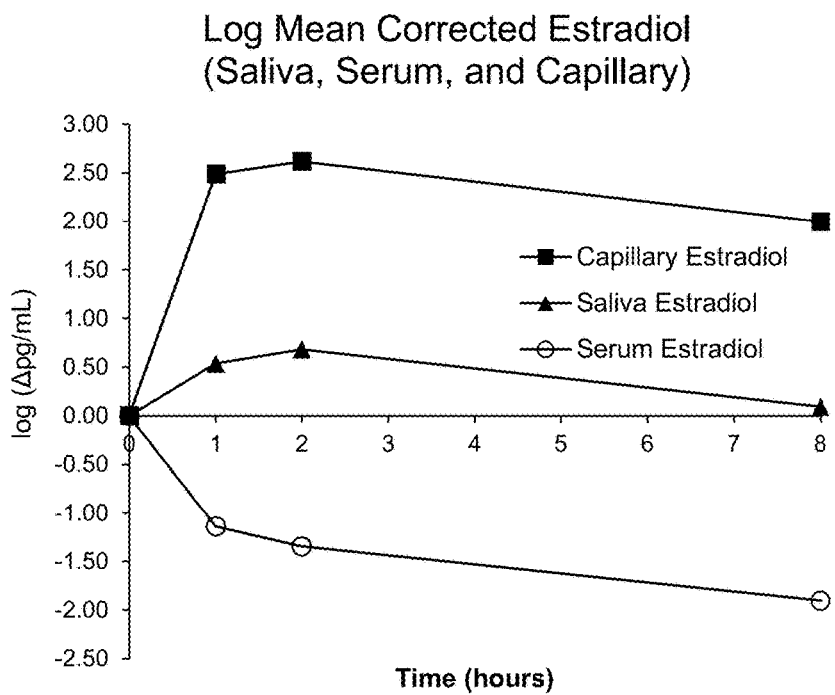
FIG. 6B shows the data plotted on a log scale.

Changes in progesterone levels in serum, saliva, and capillary fluid are plotted in FIG. 5, and changes in estradiol levels in serum, saliva, and capillary fluid are plotted in FIG. 6. No significant changes in hormone levels were seen in the serum samples following administration. However, large increases in progesterone concentration above baseline were observed for capillary fluid and saliva samples as shown in FIG. 5. Increases in estradiol concentration above baseline were also observed for capillary fluid and saliva samples as shown in FIG. 6. The high flux exhibited by the cream formulations and the large increases in hormone levels upon application of the creams indicate that the transdermal pharmaceutical compositions disclosed herein are uniquely suited for treatment of hormone deficiency and associated conditions.

Example 9. Measurement of Hormone Levels in Human Subjects after Application of Transdermal Progesterone/Estradiol Compositions Further testing was conducted to compare compositions with d-limonene (Composition III; Table 18) and without d-limonene (Composition IV; Table 19). Saliva samples were obtained at $t_0$ and then 1 g of either cream was administered to the upper arm of each of five subjects. Saliva samples were collected at 2, 4, 6, and 8 hours and analyzed for progesterone content. Results are summarized in Table 21, demonstrating that compositions with and without d-limonene provided for the efficient delivery of progesterone.

TABLE 21

Progesterone saliva concentration AUC values for individual subjects (ng*hr/mL).

| | Subject | | | | |
|---|---|---|---|---|---|
| | 1 | 2 | 3 | 4 | 5 |
| | AUC (ng · hr/mL) | | | | |
| Composition III | 116,704 | 11,902 | 5,232 | 212,693 | 898,402 |
| Composition IV. | 61,377 | 14,958 | 2,871 | 50,943 | 166,897 |

Example 10. Transdermal Progesterone Opposes the Effects of Estradiol on the Reproductive Tract of the Female Rat This example demonstrates that transdermally delivered progesterone can block the growth-related estrogenic effects on the endometrium and vagina in ovariectomized rats. When topically applied using a formulation as described herein, progesterone successfully penetrated the skin of rats in a model of estradiol-induced endometrium proliferation to an extent that resulted in clinically relevant cellular changes on reproductive organs and reversed the endometrial proliferation induced by estradiol. The topical formulation used is set forth in Table 16.

Thirty-two 8-week-old, female, Crl:CD® rats underwent ovariectomy 2 weeks prior to the start of the study. Rats were randomly assigned to 4 groups of 8 rats each. Three of the groups received 3 μg/kg/day estradiol, subcutaneously (SC), for 8 days as well as a placebo cream, 10 mg/kg/day progesterone, SC, or 3.125 mg/day progesterone transdermally beginning on Day 4. The fourth group received saline, SC for 8 days and placebo cream beginning on Day 4. Two hours after the final dose on Day 8, the rats were humanely euthanized, uterine weights were measured, and the vagina and distal portions of the uterine horns were fixed and processed for histology and computer-aided morphometry. Study parameters are outlined in Table 22.

TABLE 22

Treatment schedule for in vivo study of topical progesterone formulations.

| | | | | | | Number of Animals | |
|---|---|---|---|---|---|---|---|
| Group | Treatment | Route | Treatment Day | Dose Level | Dose Volume | Initial F | Terminal F |
| 1 | 17-β-Estradiol vehicle | SC | 1-8 | 0 | 5 (mL/kg) | 8 | 8 |
| | Transdermal Progesterone vehicle | Dermal | 4-8 | 0 | 125 μL/day | 8 | 8 |
| 2 | 17-β-Estradiol | SC | 1-8 | 3 μg/kg | 5 (mL/kg) | 8 | 8 |
| | Transdermal Progesterone vehicle | Dermal | 4-8 | 0 | 125 μL/day | 8 | 8 |
| 3 | 17-β-Estradiol | SC | 1-8 | 3 μg/kg | 5 (mL/kg) | 8 | 8 |
| | Progesterone | SC | 4-8 | 10 mg/kg | 5 (mL/kg) | 8 | 8 |
| 4 | 17-β-Estradiol | SC | 1-8 | 3 μg/kg | 5 (mL/kg) | 8 | 8 |
| | Transdermal Progesterone | Dermal | 4-8 | 3.125 mg | 125 μL/day | 8 | 8 |

As expected with this model, ovariectomy without hormone replacement resulted in significant atrophy of the uterus while unopposed estradiol treatment leads to hypertrophy as demonstrated by organ weight measurements and histology.

Figure 8A:
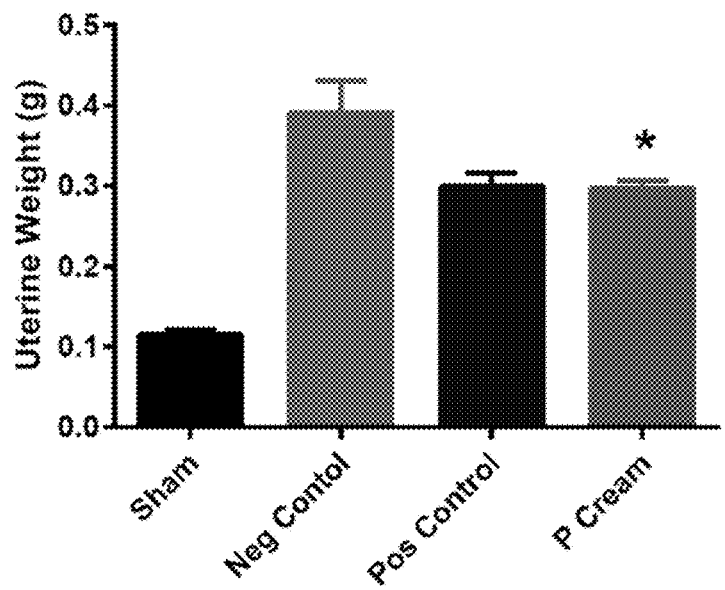
FIG. 8A shows uterine weights (after ovariectomy; mean±standard error) of rats treated with estradiol or estradiol/progesterone.
Figure 8B:
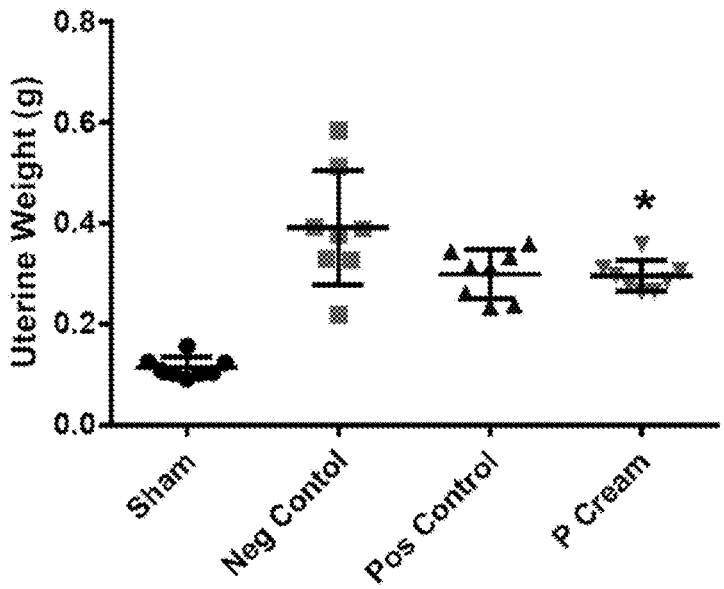
FIG. 8B shows uterine weights (after ovariectomy; mean±standard deviation) of rats treated with estradiol or estradiol/progesterone.
Figure 9:
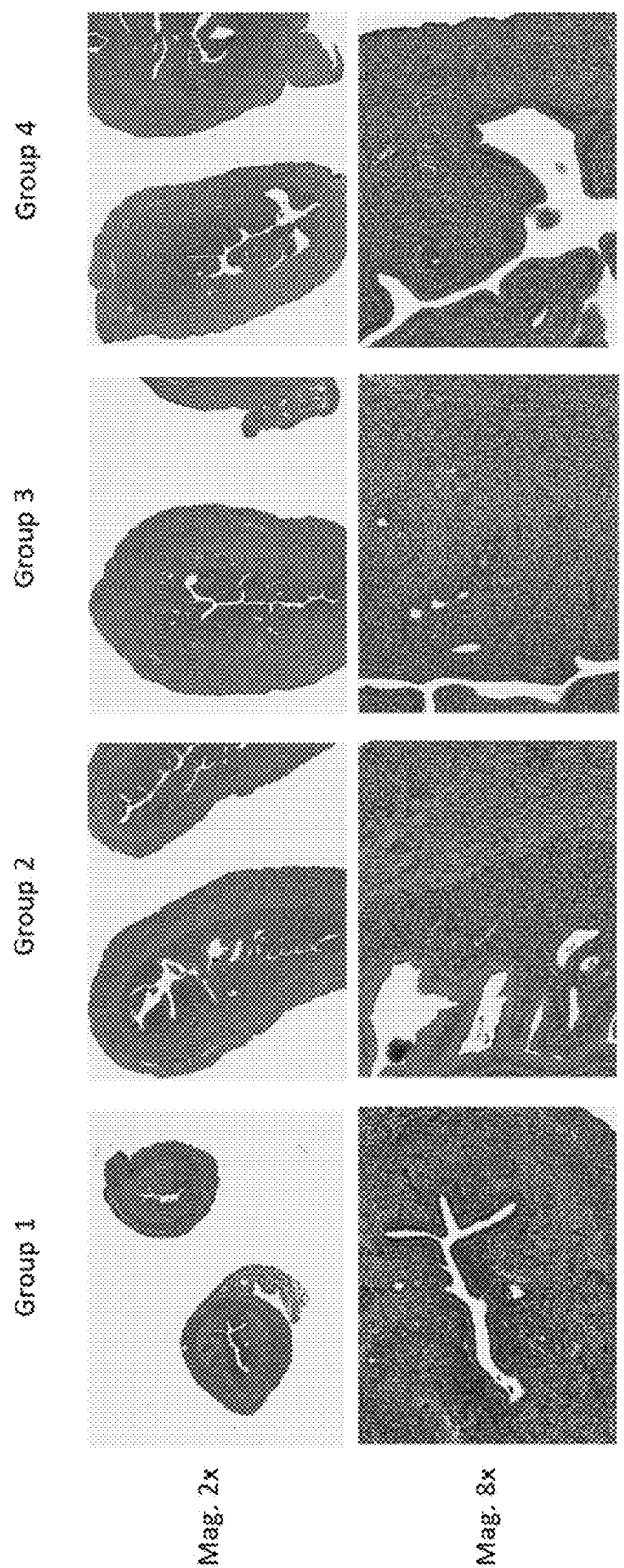
FIG. 9 shows uterine histologic specimens collected from rats treated with estradiol or estradiol/progesterone after ovariectomy; specimens stained with hematoxylin and eosin.
Figure 10:
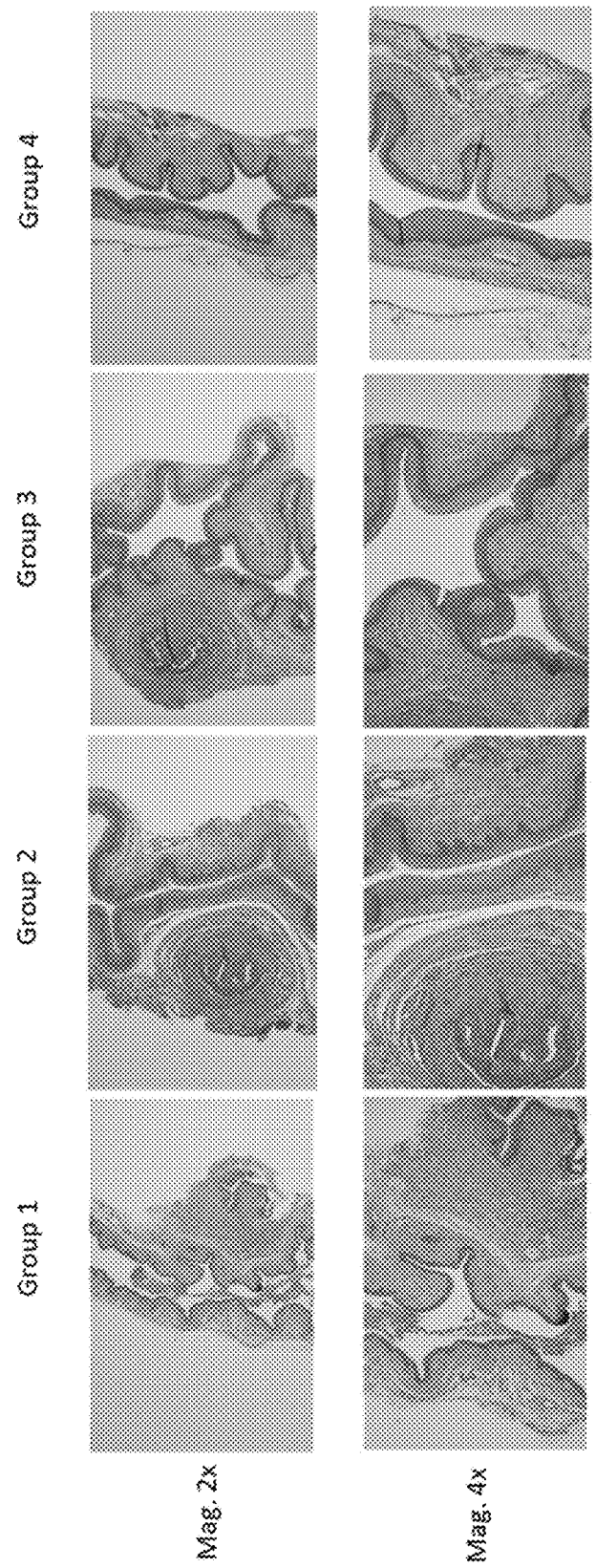
FIG. 10 shows vaginal histologic specimens collected from ovariectomized rats treated with estradiol/topical progesterone compared to rats treated with estradiol/subcutaneous progesterone and control groups; specimens stained with hematoxylin and eosin.

A pronounced reduction in uterine weight was observed in both groups receiving progesterone when compared to the estradiol-only treatment group (FIG. 8). The histological images of the uterus (FIG. 9) were consistent with the changes in uterine weights, and the overall size of the vaginal histology images (FIG. 10) were also consistent with the treatments. In addition, several estrogen-specific cellular aspects seen in the uterus (e.g., columnar luminal epithelium, eosinophilic endometrium) and vagina (e.g., keratinized epithelium, rete pegs) were not detected in group receiving progesterone SC or transdermally. See, Table 23.

TABLE 23

Histomorphometric data from rats treated with topical and subcutaneous progesterone.

| Endpoint | 0 µg/kg (SC Vehicle)/0 mg/kg (Dermal Prog) | | 3 µg/kg (SC EST)/ 0 mg/kg (Dermal Prog) | | 3 µg/kg (SC Est)/10 mg/kg (SC Prog) | | 3 µg/kg (SC Est)/3.125 mg/kg (Dermal Prog) | |
|---|---|---|---|---|---|---|---|---|
| | LSMean | LSM s.e. | LSMean | LSM s.e. | LSMean | LSM s.e. | LSMean | LSM s.e. |
| Endometrial Thickness (µm) | 236 | 20 | 418$^b$ | 20 | 436$^b$ | 31.1 | 407$^b$ | 13.5 |
| Luminal Epithelial Cell Height (µm) | 13.8 | 0.753 | 47.8$^b$ | 1.29 | 31.9$^{b,d}$ | 1.2 | 34.3$^{b,d}$ | 1.69 |
| Endometrial Gland Size (µm$^2$) | 1930 | 343 | 4540$^b$ | 343 | 4390$^b$ | 343 | 4150$^b$ | 343 |
| Endometrial Gland Density (cells/mm$^2$) | 22.0 | 1.65 | 7.09$^b$ | 0.456 | 10.3$^{b,d}$ | 0.572 | 13.3$^{b,d,f}$ | 0.694 |
| Number of Mitotic Figures | 57.7 | 6.75 | 921$^b$ | 98.2 | 595$^{b,d}$ | 63.5 | 728$^b$ | 77.7 |

LSMean—Least squares mean;
LSM s.e.—Least squares mean standard error
$^b$Significantly different from 0 µg/kg (SC Vehicle)/0 mg/kg (Dermal Prog); (p < 0.01)
$^d$Significantly different from 3 µg/kg (SC EST)/0 mg/kg (Dermal Prog); (p < 0.01)
$^f$Significantly different from 3 µg/kg (SC Est)/10 mg/kg (SC Prog); (p < 0.01)

Dosing with progesterone, both SC and transdermally, resulted in a significant reduction of luminal epithelial cell thickness compared to unopposed estradiol. A significant increase in endometrial gland density was observed for both progesterone-dosed groups compared to unopposed estradiol and additionally with transdermal as compared to SC progesterone. These data not only demonstrate that the cream formulations are able to penetrate the skin, but also that they are delivered to the target tissue and exhibit the desired biological effect.

Example 11. Exposure, Tissue Distribution, and Metabolite Profile of Transdermal Progesterone in an Animal Model Plasma, uterus, and salivary gland levels of progesterone, allopregnanolone (ALLO), and ALLO-sulfate in the rat were compared following transdermal and subcutaneous delivery of progesterone. The results of the study demonstrated that topical delivery of progesterone lead to similar hormone levels in the uterus as subcutaneous delivery with lower plasma levels of progesterone and a lower rate of metabolism to ALLO and ALLO-sulfate.

Thirty-two 8-week-old, female, Crl:CD® rats underwent ovariectomy 2 weeks prior to study start. Rats were randomly assigned to 4 groups of 8 rats each and treated according to the schedule summarized in Table 22. Three of the groups received 3 µg/kg/day 17β-estradiol, subcutaneously (SC), for 8 days as well as a placebo cream, 10 mg/kg/day (~2.5 mg/rat/day) progesterone, SC, or 3.13 mg/rat/day progesterone transdermally beginning on Day 4. The transdermal formulation is set forth in Table 16. An additional group received vehicle, SC, for 8 days and placebo cream beginning on Day 4.

Two hours after the final dose on Day 8, the rats were humanely euthanized and plasma, salivary glands, and medial portions of the uterine horns were frozen or reserved for bioanalysis. Plasma and tissue homogenates were analyzed for progesterone, ALLO, and ALLO-sulfate using LC-MS/MS.

Figure 11A:
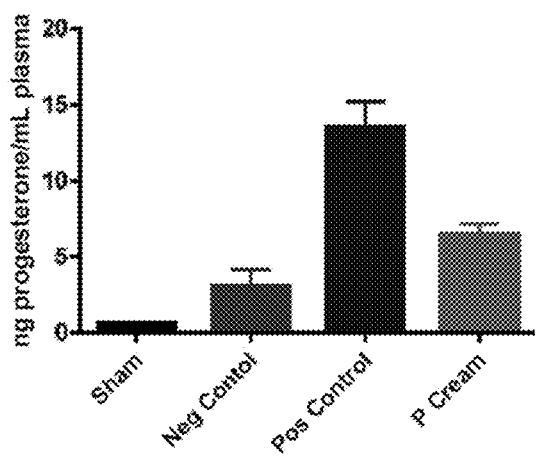
FIG. 11A shows progesterone levels observed in the plasma of ovariectomized rats treated with estradiol/topical progesterone, compared to rats treated with estradiol/subcutaneous progesterone and control groups.
Figure 11B:
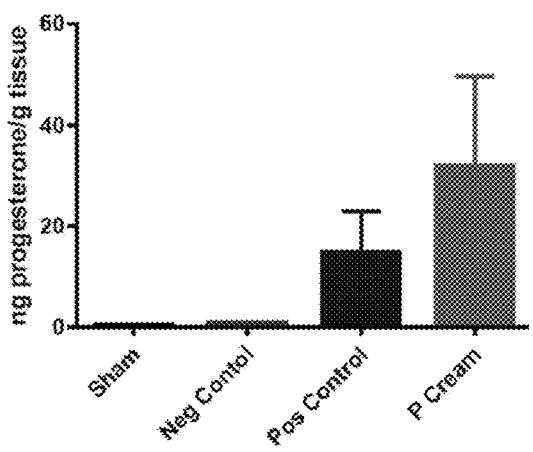
FIG. 11B shows progesterone levels observed in the salivary gland of ovariectomized rats treated with estradiol/topical progesterone, compared to rats treated with estradiol/subcutaneous progesterone and control groups.
Figure 11C:
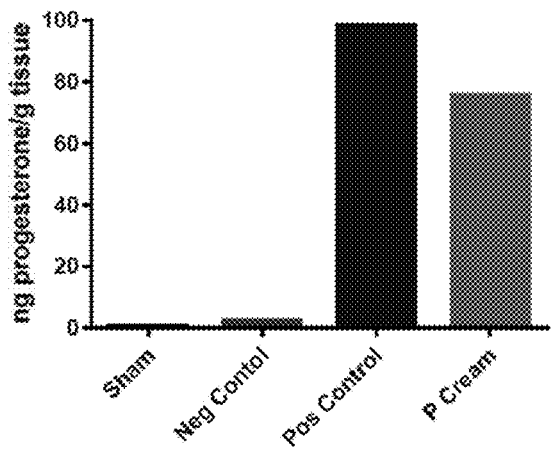
FIG. 11C shows progesterone levels observed in the uterus of ovariectomized rats treated with estradiol/topical progesterone, compared to rats treated with estradiol/subcutaneous progesterone and control groups. Geometric means are plotted for data in FIG. 11C.

Mean progesterone levels in the plasma following topical administration were 2.0 ng/mL/mg dose as compared to 5.4 ng/mL/mg dose when administered SC. Mean progesterone levels in the salivary gland and uterus following topical administration were 10 and 24 ng/mL/mg dose, respectively as compared to 5.9 and 39 ng/mL/mg dose, respectively, when administered SC. The ratio of progesterone levels in the uterus to plasma was 12 and 7.3 for the transdermal and SC routes, respectively. See, Table 24 and FIG. 11.

TABLE 24

Distribution of progesterone in rats treated with topical and subcutaneous formulations.

| | Description | Plasma (ng/mL) | Salivary (ng/g) | Salivary/ Plasma | Uterus* (ng/g) | Uterus/ Plasma |
|---|---|---|---|---|---|---|
| Group 1 | Sham | 0.63 | 0.36 | 0.57 | 0.66 | 1.05 |
| Group 2 | Placebo Cream | 3.05 | 0.80 | 0.26 | 2.37 | 0.78 |
| Group 3 | Progesterone SC | 13.5 | 14.7 | 1.09 | 98.3 | 7.28 |
| Group 4 | Progesterone cream | 6.24 | 32.0 | 5.12 | 75.4 | 12.1 |
| | Progesterone cream/SC | 0.46 | 2.18 | | 0.77 | |

*geometric mean

Although levels of ALLO in the plasma were similar with both routes of administration, the levels of ALLO-sulfate were ~12 times higher with SC administration compared to topical administration (7.6 and 0.61 ng/mL/mg dose, respectively). In all instances, the mean tissue levels of both ALLO and ALLO-sulfate were higher with SC administration compared to topical administration. Furthermore, the sum of the plasma levels of these metabolites was 2 times the plasma level of progesterone after SC dosing, as compared to equivalent plasma levels after topical dosing. See, Table 25 and Table 26.

TABLE 25

Distribution of allopregnanolone in rats treated with topical and subcutaneous formulations.

| ALLO | Description | Plasma (ng/mL) | Salivary (ng/g) | Salivary/Plasma | Uterus (ng/g) | Uterus/Plasma |
|---|---|---|---|---|---|---|
| Group 1 | Sham | 2.63 | BQL | NC | BQL | NC |
| Group 2 | Placebo Cream | 3.33 | BQL | NC | BQL | NC |
| Group 3 | Progesterone SC | 5.80 | 11.5 | 1.98 | 18.8 | 3.24 |
| Group 4 | Progesterone cream | 4.69 | 4.35 | 0.93 | 4.43 | 0.94 |
| | Progesterone cream/SC | 0.81 | 0.38 | | 0.24 | |

BQL = below quantification limit;
NC = not calculable

TABLE 26

Distribution of allopregnanolone-sulfate in rats treated with topical and subcutaneous progesterone.

| ALLO-sulfate | Description | Plasma (ng/mL) | Salivary (ng/g) | Salivary/Plasma | Uterus (ng/g) | Uterus/Plasma |
|---|---|---|---|---|---|---|
| Group 1 | Sham | 0.09 | BQL | NC | BQL | NC |
| Group 2 | Placebo cream | 0.04 | BQL | NC | BQL | NC |
| Group 3 | Progesterone SC | 19.4 | 1.50 | 0.08 | 2.61 | 0.13 |
| Group 4 | Progesterone cream | 1.87 | 0.08 | 0.04 | 0.06 | 0.03 |
| | Progesterone cream/SC | 0.10 | 0.05 | | 0.03 | |

BQL = below quantification limit;
NC = not calculable

Example 12. Progesterone Cream Formulations at Multiple Doses Demonstrates Dose-Responsive Plasma and Uterine Concentrations The plasma and uterine concentrations of progesterone was determined following the application of two 2.5% progesterone cream formulations, with and without d-limonene at a range of doses. The composition with d-limonene is set forth in Table 27. The composition without d-limonene is set forth in Table 28.

TABLE 27

2.5% Topical Progesterone Cream

| Ingredient | % w/w | Qty./Batch (g) |
|---|---|---|
| Progesterone Micronized USP | 2.50 | 62.5 |
| Medium Chain Triglycerides, NF (MIGLYOL 812) | 15.00 | 375 |
| d-Limonene (High Purity Terpenes, 99) | 5.00 | 125 |
| Diethylene Glycol Mono Ethyl Ether EP/NF (TRANSCUTOL P) | 3.00 | 75 |
| Propylene Glycol Monolaurate (Type II) EP/NF (LAUROGLYCOL 90) | 5.00 | 125 |
| Butylated Hydroxytoluene, Granular, NF | 0.10 | 2.5 |
| Mixture of Glycerol monostearate EP/NF and PEG-75 stearate NF/JPE (GELOT 64) | 7.00 | 175 |
| Mixture of Cetyl Alcohol EP/NF and Ethoxylated Fatty Alcohols (Ceteth-20, Steareth-20) EP/NF (EMULCIRE 61 WL 2659) | 3.50 | 87.5 |
| CARBOPOL 980 NF Polymer | 0.20 | 5 |
| Liquid Soy Lecithin | 3.00 | 75 |
| Propylene Glycol, USP | 4.00 | 100 |
| Methylparaben, NF | 0.20 | 5 |
| Propylparaben, NF, EP, BP | 0.02 | 0.5 |
| Citric Acid Monohydrate, Granular, USP | 0.47 | 11.75 |
| Dibasic Sodium Phosphate, Dried, USP | 0.82 | 20.5 |
| Purified Water, USP | 50.19 | 1254.75 |
| TOTAL | 100.00 | 2500 |

TABLE 28

2.5% Topical Progesterone Cream

| Ingredient | % w/w | Qty./Batch (g) |
|---|---|---|
| Progesterone Micronized USP | 2.50 | 62.5 |
| Medium Chain Triglycerides, NF (MIGLYOL 812) | 15.00 | 375 |
| Diethylene Glycol Mono Ethyl Ether EP/NF (TRANSCUTOL P) | 3.00 | 75 |
| Propylene Glycol Monolaurate (Type II) EP/NF (LAUROGLYCOL 90) | 5.00 | 125 |
| Butylated Hydroxytoluene, Granular, NF | 0.10 | 2.5 |
| Mixture of Glycerol monostearate EP/NF and PEG-75 stearate NF/JPE (GELOT 64) | 7.00 | 175 |
| Mixture of Cetyl Alcohol EP/NF and Ethoxylated Fatty Alcohols (Ceteth-20, Steareth-20) EP/NF (EMULCIRE 61 WL 2659) | 3.50 | 87.5 |
| CARBOPOL 980 NF Polymer | 0.20 | 5 |
| Liquid Soy Lecithin | 3.00 | 75 |
| Propylene Glycol, USP | 4.00 | 100 |
| Methylparaben, NF | 0.20 | 5 |
| Propylparaben, NF, EP, BP | 0.02 | 0.5 |
| Citric Acid Monohydrate, Granular, USP | 0.47 | 11.75 |
| Dibasic Sodium Phosphate, Dried, USP | 0.82 | 20.5 |
| Purified Water, USP | 55.19 | 1254.75 |
| TOTAL | 100.00 | 2500 |

Fifty-six 8-week-old, female, SDHla®(SD)CVF® rats underwent ovariectomy 2 weeks prior to study start. Rats were randomly assigned to 7 groups of 8 rats each. All of the groups received 3 μg/kg/day 17β-estradiol, subcutaneously (SC), for 8 days as well as one of the following: (a) placebo cream; (b) d-limonene-containing 2.5% progesterone cream at 0.3, 1, or 3 mg/kg/day progesterone; or (c) d-limonene-free 2.5% progesterone cream at 0.3, 1, or 3 mg/kg/day beginning on Day 4. See, Table 29. The different doses of progesterone were achieved by varying the amount of 2.5% progesterone cream applied to a proportional area of skin of the rat (~4.5 mg cream/cm$^2$ skin) Two hours after the final dose (Day 8), the rats were humanely euthanized and plasma and medial portions of the uterine horns were frozen for bioanalysis. Plasma and tissue homogenates were analyzed for progesterone by LC-MS/MS.

TABLE 29

Treatment schedule for in vivo study of progesterone

| Group | Treatment | Route | Treatment day | Dose Level | Dose Volume | Number of Animals |
|---|---|---|---|---|---|---|
| 1 | 17-β-Estradiol | SC | 1-8 | 3 μg/kg | 5 (mL/kg) | 8 |
|   | Placebo cream[a] | Dermal | 4-8 | 0 | 120 μL/day |   |
| 2 | 17-β-Estradiol | SC | 1-8 | 3 μg/kg | 5 (mL/kg) | 8 |
|   | Progesterone cream 1[b] | Dermal | 4-8 | 3 mg/rat | 120 μL/day |   |
| 3 | 17-β-Estradiol | SC | 1-8 | 3 μg/kg | 5 (mL/kg) | 8 |
|   | Progesterone cream 1[b] | Dermal | 4-8 | 1 mg/rat | 40 μL/day |   |
| 4 | 17-β-Estradiol | SC | 1-8 | 3 μg/kg | 5 (mL/kg) | 8 |
|   | Progesterone cream 1[b] | Dermal | 4-8 | 0.3 mg/rat | 12 μL/day |   |
| 5 | 17-β-Estradiol | SC | 1-8 | 3 μg/kg | 5 (mL/kg) | 8 |
|   | Progesterone cream 2[c] | Dermal | 4-8 | 3 mg/rat | 120 μL/day |   |
| 6 | 17-β-Estradiol | SC | 1-8 | 3 μg/kg | 5 (mL/kg) | 8 |
|   | Progesterone cream 2[c] | Dermal | 4-8 | 1 mg/rat | 40 μL/day |   |
| 7 | 17-β-Estradiol | SC | 1-8 | 3 μg/kg | 5 (mL/kg) | 8 |
|   | Progesterone cream 2[c] | Dermal | 4-8 | 0.3 mg/rat | 12 μL/day |   |

[a] contains d-limonene
[b] Table 27
[c] Table 28

Mean progesterone levels in the plasma were dependent on the dose of progesterone applied in the d-limonene-containing formulation (17.9, 11.4, and 4.07 ng/mL for 3.0, 1.0, and 0.3 mg/kg/day, respectively). Similarly, the formulation without d-limonene resulted in plasma levels that were generally dose-dependent (19.4, 9.15, and 7.45 ng/mL for 3.0, 1.0, and 0.3 mg/kg/day, respectively; Table 30). The concentrations of progesterone detected in the uteruses with both formulations were also generally dose responsive (with d-limonene: 33.6, 27.1, and 6.08 ng/g; without d-limonene: 36.4, 15.5, and 9.31 ng/g for 3.0, 1.0, and 0.3 mg/kg/day, respectively; Table 31).

TABLE 30

Plasma progesterone levels after repeated dosing.

| Plasma Levels | Mean ± SD (ng/mL plasma) | |
|---|---|---|
| Dose (mg/kg/day) | With d-limonene | Without d-limonene |
| 3.0 | 17.9 ± 4.64 | 19.4 ± 5.27 |
| 1.0 | 11.4 ± 4.67 | 9.15 ± 2.91 |
| 0.3 | 4.07 ± 3.16 | 7.45 ± 7.11 |

TABLE 31

Uterine progesterone levels after repeated dosing.

| Uterine Levels | Mean ± SD (ng/g tissue) | |
|---|---|---|
| Dose (mg/kg/day) | With d-limonene | Without d-limonene |
| 3.0 | 33.6 ± 1.57 | 36.4 ± 2.65 |
| 1.0 | 27.1 ± 5.78 | 15.5 ± 1.30 |
| 0.3 | 6.08 ± 0.461 | 9.31 ± 1.49 |

Example 13. Toxicity Study of Transdermal Progesterone in an Animal Model

Dermal safety and systemic exposure of 2.5% progesterone cream (see, Table 27) was assessed during and after 13 weeks of daily dermal administration to Göttingen Minipigs®. Twenty-one 4-month-old (juvenile), female, minipigs were randomly assigned to 3 groups (untreated, placebo control, and 2.5% progesterone cream) of 7 minipigs each. The placebo and active creams were applied to 10% body surface area once per day at the rate of the 4.5 mg formulation/cm$^2$ (approximately 4 mg progesterone/kg body weight). Parameters evaluated at 14 and 90 days included clinical signs, dermal irritation, body weight, ophthalmoscopy, electrocardiography, clinical pathology, toxicokinetics, gross pathology, organ weights and histopathology. Following 14 days of daily dosing, an interim sacrifice occurred with 1 animal/group. At terminal necropsy, 4 animals/group were sacrificed and the remaining 2 animals/group underwent a 14 day recovery period prior to sacrifice.

Plasma levels of progesterone were at or near the limit of quantification of the assay (0.05 ng/mL) prior to dosing on Day 1 for all animals. Following dosing on Day 1, the minipigs in the progesterone cream group showed maximum plasma levels of 0.20 to 0.77 ng/mL. On Day 14, predose levels ranged from 0.56 to 5.5 ng/mL, which is consistent with occurrence of accumulation of progesterone upon repeated administration. The maximum plasma concentrations were not significantly higher than predose levels suggesting that progesterone had achieved nearly steady-state levels. The study demonstrates that topically-applied progesterone successfully penetrates the skin of the minipig, a model of human skin penetration.

TABLE 32

Progesterone Plasma Concentrations in Minipig Model

| Group* | Composition | Progesterone Concentration in Minipig Plasma Day 1 | | | Progesterone Concentration in Minipig Plasma Day 14 | | |
|---|---|---|---|---|---|---|---|
| | | Time point (hr) | Average (ng/mL) | SD | Time point (hr) | Average (ng/mL) | SD |
| 1 | Untreated | 0 | 0.124 | 0.141 | 0 | 0.050 | $7.49 \times 10^{-18}$ |
| | | 1 | 0.204 | 0.353 | 1 | 0.071 | 0.024 |
| 2 | Placebo Cream | 0 | 0.145 | 0.126 | 0 | 0.059 | NC |
| | | 1 | 0.082 | 0.084 | 1 | 0.072 | 0.033 |
| 3 | 2.5% Progesterone Cream | 0 | 0.050 | 0.000 | 0 | 2.920 | 1.958 |
| | | 1 | 0.200 | 0.253 | 1 | 3.593 | 1.665 |
| | | 3 | 0.274 | 0.147 | 3 | 3.300 | 1.529 |
| | | 6 | 0.342 | 0.153 | 6 | 2.569 | 1.649 |
| | | 12 | 0.293 | 0.116 | 12 | 1.625 | 0.965 |
| | | 24 | 0.211 | 0.103 | 24 | 1.554 | 1.191 |

*n = 7
SD = standard deviation;
NC = not calculable

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A transdermal pharmaceutical composition comprising progesterone in an amount of about 2.5% (w/w);
   a medium-chain oil in an amount of about 15% (w/w), the medium-chain oil comprising medium-chain triglycerides, the medium-chain triglycerides substantially comprising caprylic triglyceride and capric triglyceride;
   d-limonene in an amount of about 5% (w/w);
   diethylene glycol monoethyl ether in an amount of about 3% (w/w);
   propylene glycol monolaurate in an amount of about 5% (w/w);
   a stearate mixture in an amount of about 7% (w/w), the stearate mixture comprising glycerol monostearate and PEG-75 stearate;
   a cetyl alcohol mixture in an amount of about 3.5% (w/w), the cetyl alcohol mixture comprising cetyl alcohol, ceteth-20, and steareth-20;
   a carbomer in an amount of about 0.2% (w/w);
   lecithin in an amount of about 3% (w/w);
   propylene glycol in an amount of about 4% (w/w);
   methyl paraben in an amount of about 0.2% (w/w);
   propyl paraben in an amount of about 0.02% (w/w);
   citric acid in an amount of about 0.5% (w/w);
   sodium phosphate in an amount of about 0.8% (w/w); and
   purified water;
   wherein the pharmaceutical composition is formulated as a cream for topical administration.

2. The transdermal pharmaceutical composition of claim 1, further comprising estradiol in an amount of about 0.005% (w/w).

3. The transdermal pharmaceutical of claim 1, further comprising butylated hydroxytoluene in an amount of about 0.1% (w/w).

4. The transdermal pharmaceutical composition of claim 3, further comprising estradiol in an amount of about 0.005% (w/w).

5. A transdermal pharmaceutical composition comprising progesterone in an amount of about 2.5% (w/w);
   a medium-chain oil in an amount of about 15% (w/w), the medium-chain oil comprising medium-chain triglycerides, the medium chain triglycerides substantially comprising caprylic triglyceride and capric triglyceride;
   diethylene glycol monoethyl ether in an amount of about 3% (w/w);
   propylene glycol monolaurate in an amount of about 5% (w/w);
   a stearate mixture in an amount of about 7% (w/w), the stearate mixture comprising glycerol monostearate and PEG-75 stearate;
   a cetyl alcohol mixture in an amount of about 3.5% (w/w), the cetyl alcohol mixture comprising cetyl alcohol, ceteth-20, and steareth-20;
   a carbomer in an amount of about 0.2% (w/w);
   lecithin in an amount of about 3% (w/w);
   propylene glycol in an amount of about 4% (w/w);
   methyl paraben in an amount of about 0.2% (w/w);
   propyl paraben in an amount of about 0.02% (w/w);
   citric acid in an amount of about 0.5% (w/w);
   sodium phosphate in an amount of about 0.8% (w/w); and
   purified water;
   wherein the pharmaceutical composition is formulated as a cream for topical administration.

6. The transdermal pharmaceutical composition of claim 5, further comprising estradiol in an amount of about 0.005% (w/w).

7. The transdermal pharmaceutical composition of claim 5, further comprising estradiol in an amount of about 0.05% (w/w).

8. The transdermal pharmaceutical composition of claim 5, further comprising butylated hydroxytoluene in an amount of about 0.1% (w/w).

9. The transdermal pharmaceutical composition of claim 8, further comprising estradiol in an amount of about 0.005% (w/w).

10. The transdermal pharmaceutical composition of claim 8, further comprising estradiol in an amount of about 0.05% (w/w).

* * * * *

UNITED STATES PATENT AND TRADEMARK OFFICE
CERTIFICATE OF CORRECTION

| | | |
|---|---|---|
| PATENT NO. | : 10,098,894 B2 | Page 1 of 1 |
| APPLICATION NO. | : 14/812179 | |
| DATED | : October 16, 2018 | |
| INVENTOR(S) | : Julia Amadio et al. | |

It is certified that error appears in the above-identified patent and that said Letters Patent is hereby corrected as shown below:

In the Claims

In Column 48, Claim 3, Line 9, please insert the word --composition-- so that Claim 3 reads:
--The transdermal pharmaceutical composition of claim 1, further comprising butylated hydroxytoluene in an amount of about 0.1% (w/w).--

Signed and Sealed this
First Day of January, 2019

Andrei Iancu
*Director of the United States Patent and Trademark Office*